(12) United States Patent
Panken et al.

(10) Patent No.: US 8,834,392 B2
(45) Date of Patent: Sep. 16, 2014

(54) POSTURE STATE CLASSIFICATION FOR A MEDICAL DEVICE

(71) Applicant: Medtronic, Inc., Minneapolis, MN (US)

(72) Inventors: Eric J. Panken, Edina, MN (US); Amanda D. Gaudreau, Loveland, CO (US)

(73) Assignee: Medtronic, Inc., Minneapolis, MN (US)

( * ) Notice: Subject to any disclaimer, the term of this patent is extended or adjusted under 35 U.S.C. 154(b) by 47 days.

(21) Appl. No.: 13/761,244

(22) Filed: Feb. 7, 2013

(65) Prior Publication Data

US 2014/0058289 A1    Feb. 27, 2014

Related U.S. Application Data

(63) Continuation of application No. 12/769,484, filed on Apr. 28, 2010, now Pat. No. 8,388,555.

(60) Provisional application No. 61/293,238, filed on Jan. 8, 2010.

(51) Int. Cl.
*A61B 5/00* (2006.01)
(52) U.S. Cl.
USPC ............................................. 600/595; 607/7
(58) Field of Classification Search
USPC .................... 600/509, 587, 595; 607/7, 11
See application file for complete search history.

(56) References Cited

U.S. PATENT DOCUMENTS 7,826,981 B2 * 11/2010 Goode et al. ............ 702/23
8,529,448 B2 * 9/2013 McNair ................... 600/301
8,649,862 B2 * 2/2014 Ludwig et al. ............ 607/7

FOREIGN PATENT DOCUMENTS

EP    1731097 A2    12/2006

* cited by examiner

*Primary Examiner* — Max Hindenburg
(74) *Attorney, Agent, or Firm* — Beth L. McMahon

(57) ABSTRACT

Techniques relate to operating a medical device in response to a detected posture state of a patient. A trigger event such as a request to modify how therapy is being delivered to the patient may cause a determination to be made as to whether the patient's posture state is stable. If the posture state is stable, an association is created between the posture state and one or more therapy parameter values. Over time, a library of such associations is created that may reflect any posture state in three dimensional space, wherein a posture state comprises at least one of a posture and an activity component. The library of associations may be used to automatically control therapy delivery. Similar ones of the associations may automatically be grouped into posture state regions to facilitate more efficient classification of the patient's posture state to control therapy delivery.

32 Claims, 26 Drawing Sheets

| Posture State ~160 | Estimated Vector ~162 | Estimated Method ~163 | Tolerance ~164 | Optimal Activity Parameter ~165 | Therapy Parameters ~166 |
|---|---|---|---|---|---|
| Upright | [$V_{up1}$, $V_{up2}$, $V_{up3}$] | Captured | Cone 1 | A1 | P1 |
| Lying Back | [$V_{Fu1}$, $V_{Fu2}$, $V_{Fu3}$] | Reference Vector | Cone 2 | • | • |
| Lying Front | -[$V_{Fu1}$, $V_{Fu2}$, $V_{Fu3}$] | Angular Relationship | Cone 3 | • | • |
| Lying Left | [$V_{L1}$, $V_{L2}$, $V_{L3}$] | Function of one or more vectors | Cone 4 | • | • |
| Lying Right | -[$V_{L1}$, $V_{L2}$, $V_{L3}$] | Angular Relationship | Cone 5 | • | • |
| • | • | • | • | • | • |
| Posture State X | Vector X | Relationship X | Tolerance X | Ax | Px |

FIG. 9

POSTURE STATE CLASSIFICATION FOR A MEDICAL DEVICE

RELATED APPLICATIONS

This application is a continuation of, and claims prior to, U.S. patent application Ser. No. 12/769,484 filed Apr. 28, 2010, which claims priority to provisionally-filed U.S. Patent Application Ser. No. 61/293,238 filed Jan. 8, 2010, both of which are incorporated herein by reference in their entirety.

TECHNICAL FIELD

The invention relates to posture detection techniques, and more particularly, to medical devices that detect posture states.

BACKGROUND

A variety of types of medical devices are used for chronic, e.g., long-term, provision of therapy to patients. As examples, pulse generators are used for provision of cardiac pacing and neurostimulation therapies, and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY

According to one aspect, techniques are provided for creating an association between a patient's posture state and at least one therapy parameter that may be used to control therapy delivery when the patient occupies that posture state. In one scenario, the indication of the patient's posture state is obtained from a posture state sensor, such as a three-axis accelerometer. Any other sensor that provides an indication of posture state may be used in the alternative. The indication describes at least one of a posture and an activity component. The indication may be, for instance, a vector in three-dimensional space.

In one embodiment, an association between a posture state and at least one therapy parameter is created in response to receipt of a trigger event. The trigger event may be a request to adjust the therapy that is being delivered to the patient, for instance. The trigger event may instead be expiration of a timer or some other event that prompts sampling of the posture state sensor.

When the trigger event occurs, in one scenario, a signal from the posture state sensor may be evaluated. This may involve obtaining multiple samples from the posture state sensor. Based on these samples, a determination may be made as to whether the patient's posture state is stable. If it is determined to be stable, the association between this posture state and one or more corresponding therapy parameter values may be created. Such an association may be stored in a memory, which may reside within an implantable medical device (IMD), a programmer, or some other device such as a server accessible to the IMD or programmer. Thereafter, the system may detect when the patient assumes a posture state that is sufficiently similar to a posture state reflected by the association. When such a condition is detected, therapy may be delivered to the patient according to the one or more therapy parameter values associated with this posture state.

Determining whether a detected posture state of a patient is sufficiently similar may involve, for instance, determining a distance between a parameter (e.g., a vector) indicative of a patient's current posture state and another parameter indicative of the posture state represented by the association. Such a distance may be determined as an angle, a straight-line distance, a city-block, a trigonometric function, or any other distance metric. The distance may be derived between two vectors, with one of the vectors describing a current posture state of the patient and the other vector describing the posture state represented by the association.

Many different techniques may be employed to determine whether a posture state of is stable. In one embodiment, a selectable (e.g., programmable) set of criteria may be used to make this determination. The criteria may be selected by a device manufacturer, an end-user (e.g., a clinician), or both. The criteria may, for instance, require that M of N successive samples of a signal obtained from the posture state sensor be within a predetermined threshold distance of a preceding sample. The distance may be determined using the example methods set forth above or using any other distance metric.

In one specific example, the M of N samples used to determine stability must be obtained during a search window of time that has a predetermined duration and follows occurrence of a trigger event, such as a request to adjust therapy. In an even more specific example, these samples must be obtained during a stability window that is shorter than, and at least partially overlaps, the search window. If a stability window of time can be located wherein M of N samples are within a predetermined distance of a preceding sample, the patient's posture state is determined to be stable such that an association between the posture state and at least one therapy parameter value can be created.

In another embodiment, stability criteria additionally or alternatively determine whether a posture shift or change may be underway within a latter portion of the stability window. This latter portion may include a predetermined number of samples that are obtained at the end of the stability window, for instance. If such samples indicate a shift may be occurring, the posture state may be determined to be unstable even if criteria associated with M of N samples, as discussed above, is satisfied. Any other stability criteria that determine stability of a posture state sensor may be used in the alternative to determine whether an association between a posture state and one or more therapy parameters may be created.

As discussed above, a set of stored associations between stable posture states and therapy parameters, also referred to as a library of associations, may be created over time. As each new posture state indication is received from the posture state sensor for a stable posture state, it may be determined whether that new posture state should be used to create another association. In one embodiment, this involves determining whether the newly-detected posture state is already represented by one of the stored associations. This may involve determining whether a vector indicative of the newly-detected posture state is sufficiently similar, or close, to a vector that represents the posture state of the stored association. This may involve determining whether theses two vectors are within some threshold distance of one another.

If a newly-detected posture state is indeed similar to a posture state of a stored association, the stored association may be updated. For instance, this association may be updated to represent a posture state that reflects not only the newly-detected posture state but the posture state previously associated with the association. As a specific example, a parameter value (e.g., a vector) that had previously been stored for the association may be averaged with another parameter value (e.g., a vector) for the detected posture state. The resulting parameter value may then be used to represent the new posture state for the updated association. Other functions may be used to obtain this type of representation of a posture state that reflects not only the detected posture state, but the posture state that had previously been represented by the association. In this manner, existing associations are adapted over time as the patient's set of frequently-occupied posture state changes in response to therapy delivery, changing health conditions, and so on.

Additionally, any therapy parameter values that were associated with the newly-detected posture state (e.g., as a result of a therapy modification request) may be used to update an existing association. Such therapy parameter values may simply replace the previous therapy parameter values for the association. Alternatively, some function may be used (e.g., an averaging function) to derive the one or more therapy parameter values from the newly-received therapy parameter values and values that had previously been associated with the posture state.

In some cases, a newly-detected posture state may not be sufficiently similar to any posture state that is already represented by the stored associations. In such cases, a new association between the newly-detected posture state and one or more therapy parameter values may be created. The therapy parameter values for this new association may be obtained based on those provided by a user (e.g., as the result of a patient request to modify therapy.) If therapy parameter values were not provided by the user when the posture state was detected, the therapy parameter values to be used for the association may be obtained in another way. For instance, a search of all existing associations may be performed to identify a posture state that is closest, or most similar, to the detected posture state. As discussed above, "closeness" or "similarity" may be determined using many different distance metrics, and may involve determining a distance between two vectors. In some cases, the two vectors are described in a coordinate system of the posture state sensor, rather than in terms of a body coordinate system, leading to enhanced processing efficiency.

Once the association for the posture state that is closest to the detected posture state is located, the therapy parameter value(s) from this located association may be used to create the new association.

Another way to determine the therapy parameter value(s) for the new association is to utilize those therapy parameter values most-recently used to provide therapy to the patient. This approach may be beneficial if a search of existing associations does not locate any associations for posture states that are sufficiently spatially similar, or close to, the detected posture state. In this case, applying a temporal, rather than a spatial, association may be preferred. Of course, other mechanisms may be used to determine the therapy parameter values to use to create a new association, and the foregoing are examples that are not to be considered limiting.

As described above, a threshold distance may be selected to determine whether to update an existing association or create a new association, with a new association being formed only if a detected posture state is not within some threshold distance of a posture state of an existing association. This threshold distance may, in one embodiment, be programmable. This distance may be dynamically selected based on available system resources, such as the storage space available within the system to store associations. The distance may alternatively or additionally be dynamically selected based on a time of day, a day of the week, a time since a medical procedure (e.g., time elapsed since implant), and so on. This may allow the manner in which associations are created to be programmably and dynamically controllable. For instance, it may be desirable to create more closely-spaced associations at certain times of a work day when a patient is known to occupy many similar yet distinct posture states. At other times, it may be desirable to create entries that are more spaced out, which may conserve power resources within the system.

In the foregoing manner, all of three-dimensional space may be populated over time with associations between posture states (e.g., as represented by vectors in one embodiment) and corresponding therapy parameter(s). In another embodiment, only some of three-dimensional space may be populated with such associations. For instance, in some cases, some predetermined posture state definitions may be created using a calibration mechanism when an IMD is first deployed. Such predetermined posture state definitions may represent posture states that are most likely to be occupied by a patient, such as the Upright and certain Lying posture states. Since such predetermined posture states definitions need not be collected over time in the same way required for the created associations, the predetermined posture states associated with the definitions are available to control therapy delivery within a relatively short period of time after implant. That is, whenever a patient's posture state falls within the bounds of one of these predetermined posture state definitions, therapy may be delivered according to parameters associated with the corresponding pre-established definition, even if enough time has not elapsed to create any associations between posture states a patient may occupy and therapy parameters.

In an embodiment wherein predetermined posture state definitions are available for use in the aforementioned manner, it may be desirable to only create dynamic associations over time for posture states that are not associated with (e.g., fall outside of) the predetermined posture state definitions. Thus, three-dimensional space may include space allocated to the pre-established posture state definitions that are calibrated relatively soon after device deployment, and the space outside of these definitions may remain available to be dynamically populated with posture state/therapy associations.

In an alternative embodiment, it may be desirable to have a predetermined set of posture states that are calibrated when an IMD is first deployed in the manner described above. Such posture state definitions may be used initially to control therapy delivery for the patient. However, over time, as trigger events occur, associations may be dynamically created between stable posture states and corresponding therapy parameters that take precedence over the initially-employed posture state definitions. According to this approach, the posture state definitions may be visualized as regions in three-dimensional space that are initially available for therapy control, but are "eroded away" over time, being replaced by the new dynamically-created associations between posture states and therapy parameters. In this manner, therapy may eventually be delivered to the patient according to the multiple dynamically-created associations and regardless of whether a posture state definition also exists for a given posture state. That is, eventually if a patient's detected posture state falls within the bounds of both a predetermined posture state definition and one of the dynamically-created associations, the association will be used to control therapy delivery instead of the posture state definition.

In some cases, once associations have been created for posture states, it may be desirable to create one or more posture state regions from the associations. Each such posture state region represents similar ones of the multiple associations. For instance, associations that are spatially similar (e.g., associated with vectors that occupy a similar region in three-dimensional space) may be grouped into a posture state region. The posture state regions may be formed to include those associations that are not only spatially similar, but that are also associated with similar therapy parameter values. As a simply example, a posture state region may be created that is a cone in three-dimensional space and that includes vectors that are each associated with therapy parameter values that are within some threshold distance of one another. The criteria used to determine spatial and parameter similarities for posture state region creation may be programmable. In one embodiment, the posture state regions are automatically created by applying clustering techniques to the associations, as is known in the art.

Each posture state region may be associated with one or more therapy parameter values. The therapy parameter values associated with a posture state region may be obtained based on the therapy parameter values of the associations used to form the region (e.g., as an average, weighted average, or some other function of these parameter values.) When a patient's posture state is detected, if the posture state falls within one of the posture state regions, therapy may be delivered according to the parameter values associated with that posture state region. This type of embodiment may allow therapy delivery to be performed more efficiently, since a search of the posture state regions may be completed more quickly than a search of all associations.

If desired, after posture state regions are created, the associations used to create these regions may be maintained in parallel with the posture state regions. In other words, as trigger events occur that may prompt detection of a new stable posture state, this posture state may be used to update an existing, or create a new, association. This allows the associations to remain current, representing a current set of frequently-occupied posture states. Periodically the posture state regions may be regenerated from the then-current set of associations. In an alternative embodiment, after creation of the posture state regions, any newly-detected posture states that would otherwise be used to create or update the associations are instead used to directly create or update the posture state regions, which reflect the most current set of posture states.

Additional aspects of the disclosure will become apparent to those skilled in the art from the following description and accompanying drawings.

BRIEF DESCRIPTION OF THE DRAWINGS

FIG. 9 is an example data structure illustrating associations between posture states and therapy parameter sets.

DETAILED DESCRIPTION

Figure 1:
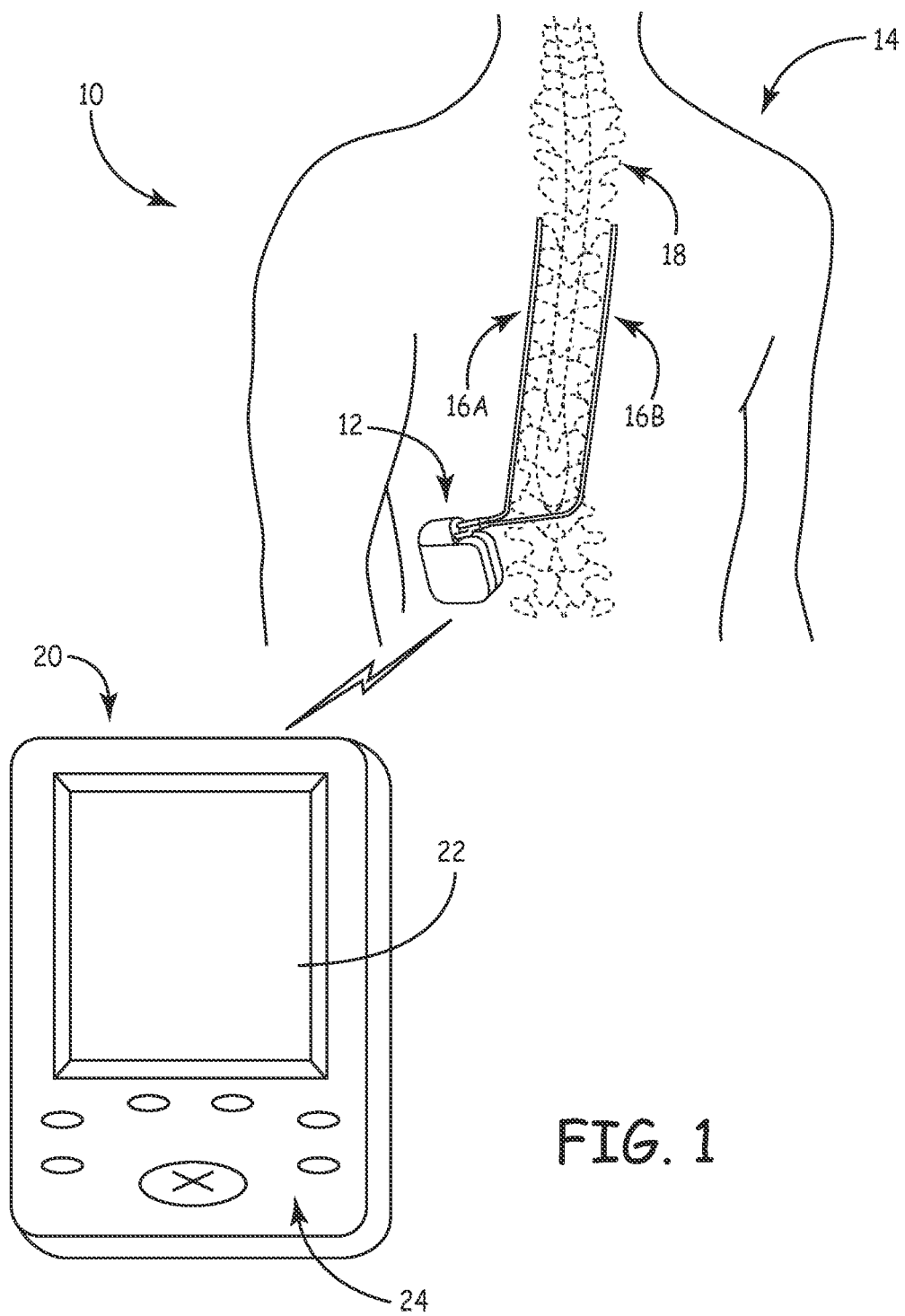
FIG. 1 is a conceptual diagram illustrating an example system that facilitates the definition and classification of posture states according to the disclosure.

Techniques described herein relate to classification of a patient's posture state. Such a posture state may involve at least one of a posture and an activity. Classification of a patient's posture state may then be used to initiate a response. For instance, such classification may be used to deliver therapy in a closed-loop manner.

Examples of therapies that may be delivered in a closed-loop manner using techniques presented in the current disclosure include electrical stimulation or the delivery of therapeutic agents. Electrical stimulation may be, for example, used to treat patients that suffer from chronic back pain, leg pain, or other pain that cannot be treated through other methods. As a patient changes posture state, which may involve changes in position and/or activity, the stimulation may need to be adjusted in order to maintain efficacy. Such changes in a patient's posture state may be detected, classified, and used to modify a therapy that is currently being delivered, or to select a new therapy for delivery to the patient. In another embodiment, the detected posture state transition may be used to prompt some notification, or to record some information.

According to some embodiments of the disclosure, a medical device, e.g., an implantable medical device (IMD), includes or is coupled to a sensor that senses a posture state. The sensor may be a three-axis accelerometer such as a piezoelectric and/or micro-electro-mechanical (MEMs) accelerometer. The sensed posture state may then be used to initiate some action, which may be an action to be taken in regards to the patient. This action may merely involve storing the sensed posture state. The action may additionally or alternatively involve a change in delivered therapy, providing a notification (e.g., providing a warning that the patient has taken a fall), and/or any other action that is usefully taken in regards to the sensed posture state.

The IMD may store a table or other data structure that contains records. Each such record may contain therapy information associated with a respective posture state. The IMD may automatically sense the current posture state of the patient and/or changes in the posture state of the patient. This sensed information may be employed to reference the table or other data structure that contains the therapy information. An appropriate therapy may thereby be selected that provides the most efficacious results for the patient's current posture state.

According to one aspect, one or more posture states are automatically defined, and then re-defined, for the patient as the patient goes about daily life. For instance, a set of posture states such as upright, Lying Forward (i.e., face down), Lying Backward (i.e., face up), Lying Right, and Lying Left may be used by the IMD to automatically initiate actions on behalf of the patient. As an example, if a patient is sensed as being in one of these posture states, the IMD may initiate delivery of a therapy that has previously been associated with that posture state.

According to one mechanism for initially defining a posture state, a patient is required to assume the posture state. While the posture state is maintained, the output of one or more sensors of the IMD is recorded and is associated with the posture state. As a specific example, a vector obtained from one or more accelerometers may be recorded. Thereafter, this recorded information may be used to recognize when the patient re-assumes the posture state. Based on this posture state recognition, appropriate actions may be taken, such as delivering therapy to the patient according to parameters that were previously associated with the posture state.

While the foregoing approach provides an accurate way to define a posture state, it may never-the-less be somewhat inconvenient for the patient. For instance, the patient may, during an initial post-operative visit to a clinic, be required to assume various posture states, including the Upright, Lying Forward, Lying Backward, Lying Right, and Lying Left, posture states. As the patient assumes each such pose, a clinician or other user may utilize an orientation feature to record one or more sensor outputs (e.g., a vector from one or more accelerometers) that are used to define the respective posture state. Such an orientation feature may be provided, for instance, on a clinician or patient programmer. Assuming each such pose may be tedious for the patient, and time-consuming for a clinician. A more stream-lined approach allows posture states to be initially defined in a more automatic manner, without the patient being required to assume each posture state.

According to another aspect, once posture states are initially defined in an automated manner, the posture states may thereafter be automatically refined as the patient goes about daily life. This is useful since the patient's physicality may change based on a patient's changing health conditions, on effects to received therapy, or based on other conditions. Moreover, the exact pose that a patient assumes during a visit to a clinic during an initial posture state definition process (e.g., when the patient is lying on her back on a clinic examining table) may not be the same posture the patient will naturally assume at home (e.g., when the patient is lying in a similar posture state on her own bed using a familiar pillow). In addition, an aspect associated with the sensor may change, causing posture state definitions to require refinement. For instance, the orientation of the IMD (and hence a sensor carried by the IMD) within the patient's body may change, either as a result of normal shifting, or because of patient interaction of the type that may occur because of Twiddler's Syndrome. Additionally, the sensor may experience some "drift", or small error over time, such that the sensor output that is provided in response to a given set of input conditions changes slowing over time. As a result of any of these types of conditions, sensor signals obtained during an initial definition process for a particular posture state may not be the same signals that correspond to that posture state at a later point in time.

For any of the foregoing, or other reasons, it may be beneficial to periodically update posture state definitions. As one example, a patient's standing (Upright) posture state may become more erect over time as a result of the positive effects of therapy. In this case, continuing to use an older definition of an upright posture state may lead to inaccurate recognition of the posture state. Instead, it is beneficial to automatically recognize that the patient now holds himself more erect when standing, and to therefore update the corresponding Upright posture state definition to reflect this change. This modification will allow for improved posture state detection. Moreover, allowing this change to occur automatically will eliminate any need for the patient to periodically undergo any manual procedure to update the posture state definitions.

FIG. 1 is a conceptual diagram illustrating an example system 10 that facilitates the definition and classification of posture states according to the disclosure. In the illustrated example, system 10 includes an IMD 12, which is implanted within a patient 14, and delivers neurostimulation therapy to patient 14.

IMD 12 delivers neurostimulation therapy to patient 14 via therapy connections 16A and 16B ("therapy connections 16"), which may be leads carrying electrodes, for instance. In this type of application, the electrodes (not shown) may be, e.g., electrode pads on a paddle lead, circular (e.g., ring) electrodes surrounding the body of leads, conformable electrodes, cuff electrodes, segmented electrodes, or any other type of electrodes capable of forming unipolar, bipolar, omnipoloar or multipolar electrode configurations for therapy. In some applications, such as SCS to treat chronic pain, the adjacent therapy connections 16 may have longitudinal axes that are substantially parallel to one another, and one therapy connection need not have the same number of electrodes as another therapy connection.

More than two, or only one, of the therapy connections 16 may be provided by the system. In one case, three therapy connections 16 may be provided, each carrying electrodes to form a so-called 4-8-4 or 4-16-4 lead configuration, whereby the numbers indicate the number of electrodes in a particular column, which can be defined by a single lead. Other lead configurations, such as 8-16-8, 8-4-8, 16-8-16, 16-4-16, are also possible. External programmer 20 may be initially told the number and configuration of leads 16 in order to appropriately program stimulation therapy.

Therapy connections 16 may, as shown in FIG. 1, be implanted proximate to the spinal cord 18 of patient 14, and IMD 12 may deliver SCS therapy to patient 14 in order to, for example, reduce pain experienced by patient 14. However, the disclosure is not limited to the configuration of therapy connections 16 shown in FIG. 1 or the delivery of SCS therapy. For example, one or more therapy connections 16 may extend from IMD 12 to the brain (not shown) of patient 14, and IMD 12 may deliver deep brain stimulation (DBS) therapy to patient 14 to, for example, treat tremor, Parkinson's disease, epilepsy, obsessive compulsive disorders, depression, or other ailments.

As further examples, one or more therapy connections 16 may be implanted proximate to the pelvic nerves, stomach, or other organs (not shown) and IMD 12 may deliver neurostimulation therapy to treat incontinence, gastroparesis, sexual dysfunction or other disorders. Additionally, this disclosure is not limited to implantable devices. Any external medical device may classify posture states for use in delivering therapy according to the techniques of the disclosure. For instance, the techniques described herein may be employed by an externally-worn trialing device that is used to determine whether a patient is a good candidate for long-term therapy.

Further, as discussed above, the disclosure is not limited to embodiments in which IMD 12 delivers stimulation therapy. For example, in some embodiments, IMD 12 may additionally or alternatively be coupled to one or more catheters or other substance delivery devices to deliver one or more therapeutic substances to patient 14, e.g., one or more drugs.

Example therapeutic agents that IMD 12 may be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics. In this case, IMD 12 functions as a drug pump and communicates with external programmer 20 to initialize therapy or modify therapy during operation. In addition, IMD 12 may be refillable to allow chronic drug delivery.

When IMD 12 delivers a therapeutic substance to the patient, multiple therapy connections 16 such as catheters may be located to each deliver the substance to a predetermined anatomical location, tissue or organ. Each catheter may deliver therapy to a same location as the other catheters, or to different tissues within patient 14 for the purpose of treating multiple symptoms or conditions. In some embodiments, IMD 12 may be an external device which includes a percutaneous catheter that provides one of therapy connections 16 or that is coupled to therapy connections 16, e.g., via a fluid coupler. In other embodiments, IMD 12 may be coupled to therapy connections 16 that provide both electrical stimulation and drug delivery therapy.

Although the target therapy delivery site may be proximate to spinal cord 18 of patient 14, other applications are possible. For instance, the target delivery site in other applications of a drug delivery system may be located within patient 14 proximate to, e.g., sacral nerves (e.g., the S2, S3, or S4 sacral nerves) or any other suitable nerve, organ, muscle or muscle group in patient 14, which may be selected based on, for example, a patient condition. In one such application, drug delivery system may be used to deliver a therapeutic agent to tissue proximate to a pudendal nerve, a perineal nerve or other areas of the nervous system, in which cases, therapy connections 16 would be implanted and substantially fixed proximate to the respective nerve. Thus, many types of applications are possible.

Also, in some aspects, techniques for evaluating postures and posture states as described herein may be applied to IMDs that are generally dedicated to sensing or monitoring and do not include stimulation or other therapy components. For instance, the posture state classification mechanisms described herein may be used for diagnostic purposes, such as diagnosing a need for therapy, or determining how a patient is responding to existing therapy. Posture state classification may also be used to provide notifications, such as providing notification via a wireless link to a care giver that a patient has potentially experienced a fall. Thus, posture definition and classification according to the current disclosure may be used to initiate many types of actions, including storing the classification for later analysis, initiating a change in therapy, prompting a notification, and so on.

In exemplary embodiments, IMD 12 functions under the control of one or more programs. A program includes one or more parameters that define an aspect of posture classification and/or detection according to that program.

In exemplary embodiments, IMD 12 may initiate actions in response to information within a record. For instance, a plurality of records may be stored in a table or other data structure. Each such record may describe at least one posture state and an associated action that is to be taken in response to detection of this posture state. As discussed above, a posture state is determined based on at least one of a defined posture and an activity component (e.g., a parameter indicative of footfalls). When IMD 12 detects a posture state, IMD 12 may initiate the action that is indicated by the information in the record for that posture state. This action may involve delivery of therapy according to a particular program, group of programs and/or a set of parameters. This action may alternatively or additionally involve providing some notification and/or recording some information.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate wirelessly with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. In still another example, the user may interact with programming device via speech recognition functionality. The user may also interact with programming device 20 using peripheral pointing devices such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a clinician programmer used by a clinician to define one or more postures and posture states. According to the current disclosure, the clinician programmer may be used to define a reduced subset of all postures states in use within the system, with the remaining posture states being defined automatically based on that initially-defined reduced subset. All of the defined posture states may then be used to detect postures and posture states that are assumed by the patient during daily life. The detected postures may be used to determine a type of therapy to provide to the patient, to monitor general well-being of the patient, to prescribe new therapies for the patient, and to determine whether the patient has undergone a posture-specific event such as suffering a fall. As discussed above, posture state definitions may, after initial definition, undergo a refinement process whereby the definitions are automatically updated to match changing conditions, such as a changing condition associated with the patient's state. This refinement process may occur substantially continuously or periodically, as will be described below.

Figure 2:
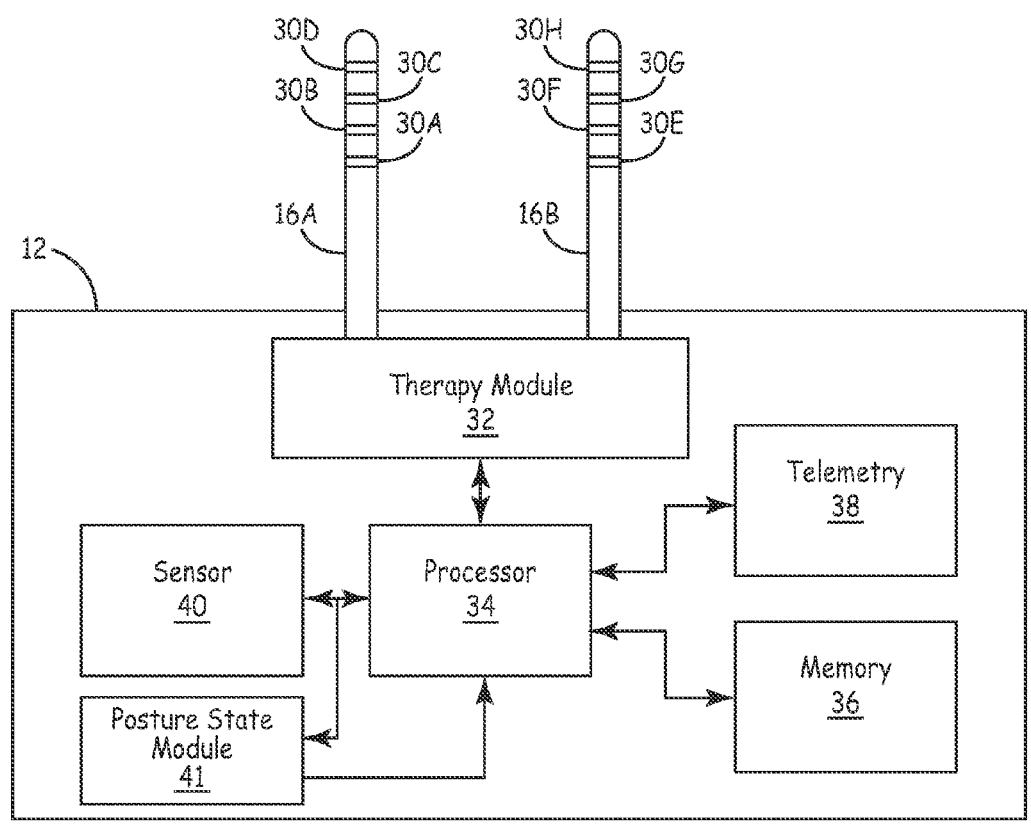
FIG. 2 is a block diagram illustrating one embodiment of an implantable medical device in greater detail.

FIG. 2 is a block diagram illustrating one embodiment of IMD 12 in greater detail. IMD 12 may deliver neurostimulation therapy via therapy connections 16A and 16B. As discussed above, these therapy connections may be leads having one or more electrodes 30A-H (collectively "electrodes 30") or some other therapy mechanism, such as one or more catheters for delivering a substance to a patient. IMD 12 may be coupled to any number of therapy connections.

Therapy connections 16A and 16B are coupled to IMD 12 via therapy module 32. This may be a stimulation pulse generator, for example. Such a pulse generator may be coupled to a power source such as a battery. Therapy module 32 may deliver electrical pulses to patient 14 and/or may deliver some type of substance, such as a drug.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with the amplitudes and widths, and at the rates specified by the program. Processor 34 may also control therapy module 32 to deliver such pulses via a selected subset of electrodes 30 with selected polarities, e.g., a selected electrode configuration, as specified by the program. Alternatively or additionally, processor 34 may control delivery of stimulation via a selected type of continuous waveform (e.g., a sinusoidal waveform, etc.).

Therapy module 32 is a type of module that may be referred to generally as a response module. In addition to, or instead of, therapy module 32, IMD 12 may include other response modules for initiating other types of responses. For instance, a notification module (not shown) may be provided to initiate the issuance of a notification to programmer 20, or to initiate some other type of communication, based on the defined posture or posture state. Alternatively, a module may be provided to initiate storing of patient-specific or system-related data based on the posture or posture state. Thus, IMD 12 may include other types of modules to initiate other types of responses in addition to, or instead of, therapy-based responses.

IMD 12 also includes a telemetry circuit 38 that allows processor 34 to communicate with programming device 20. For example, a clinician may select programs, parameters, posture definitions, posture state definitions, and associated therapies and actions that are to be transferred to memory 36 of IMD 12. Processor 34 may also communicate with programming device 20 to provide diagnostic information stored in memory 36 to a clinician via telemetry circuit 38. Processor 34 may also communicate with a patient programming device to receive from a user such as patient 14 therapy parameter adjustments or other therapy adjustments, as well as commands to initiate or terminate stimulation. Telemetry circuit 38 may correspond to any telemetry circuit known in the implantable medical device arts.

IMD 12 further includes one or more sensors (shown as sensor 40 in FIG. 2), at least one of which provides a signal indicative of a posture state of the patient. In exemplary embodiments, sensor 40 includes a three-axis accelerometer, such as a piezoelectric and/or MEMs accelerometer. In other embodiments, multiple single or multi-axis accelerometers may be employed in place of one three-axis accelerometer. In yet other examples, sensor 40 may include gyroscopes, pressure sensors, thermistors, electrodes to detect thoracic impedance, sensors to detect electrical characteristics (e.g., tissue resistance) and/or other sensors capable of sensing posture and/or activity levels. Thus, it will be understood that sensor 40 may comprise more than one sensor of more than one type.

In exemplary embodiments, sensor 40 is located within a housing (not shown) of IMD 12. However, the disclosure is not so limited. In some embodiments, sensor 40 is coupled to IMD 12 via additional therapy connections 16 (not shown). The sensor may be located anywhere within patient 14.

In alternative examples, first and second sensors may be located in different positions within patient 14 and relative to components of IMD 12. For example, one sensor may be an independent implantable sensor that is implanted adjacent to but physically disconnected from IMD 12. Another sensor may be, e.g., connected to an additional sensor lead positioned within patient 14 adjacent to therapy connections 16. Alternatively, the other sensor may be an independent implantable sensor that is implanted adjacent to but physically disconnected from therapy connections. In some examples, one posture sensor is arranged proximate a therapy delivery site within patient 14, while another sensor is arranged closer to IMD 12 than the first sensor.

In some embodiments, IMD 12 may be coupled to one or more accelerometers or other position sensors located at various positions on the external surface of patient 14. In yet other embodiments, these one or more sensors may communicate wirelessly with IMD 12 instead of requiring one or more leads to communicate with the IMD. For example, sensor 40 may be located external to patient 14 and may communicate wirelessly with processor 34, either directly or via programming device 20.

As previously mentioned, sensor 40 senses one or more parameters that are used to detect a posture state. A posture state is a state that is classified by at least one of a posture and an activity state, where the activity state may describe, for example, an overall activity level, an activity level in one or more selected directions, a vector associated with velocity or acceleration, and so on.

Example posture states that may be detected include an Upright posture state. This posture state may be defined as that occurring when the patient is in an upright posture without regard to an activity state. As another example, an Upright and Active posture state may be associated with an upright posture and an activity state that is associated with an activity level above some predetermined threshold level, for instance. Additional exemplary posture states such as "Running", "Sitting", "Bending Over", and so on, may be defined in terms of a posture and/or activity level and subsequently sensed by sensor 40.

In addition to a posture state sensor, sensor 40 may further include other sensors to sense one or more additional physiological parameters of the patient, including blood pressure, heart rate, a characteristic of the patient's blood (e.g., oxygen or $CO_2$ level, glucose level, etc.), or any other physiological parameter that may be determined by existing or future sensor technology.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as random access memory (RAM), read-only memory (ROM), non-volatile RAM (NVRAM), electrically-erasable programmable ROM (EEPROM), flash memory, and the like.

FIG. 2 further includes posture state module 41 that is provided in one embodiment to process the output of sensor 40. Posture state module 41 may include discrete components, a microprocessor, a controller, a digital signal processor (DSP), an application specific integrated circuit (ASIC), a field-programmable gate array (FPGA), and/or the like. Posture state module 41 may operate alone, or in conjunction with processor 34, to process the sensor output for use in detecting a posture state. As an example, posture state module 41 may process the raw signals provided by sensor 40 to determine activity counts indicative of activity level, velocity (as may be obtained by integrating a respective accelerometer signal), and so on, for use in detecting a posture state. This is discussed further below.

In other embodiments, posture state module 41 may additionally or alternatively be configured to sense one or more physiological parameters of patient 14. For example, physiological parameters may include heart rate, electromyography (EMG), an electroencephalogram (EEG), an electrocardiogram (ECG), temperature, respiration rate, or pH. These physiological parameters may be used by processor 34, in some embodiments, to confirm or reject changes in sensed posture state that may result from vibration, patient travel (e.g., in an aircraft, car or train), or some other false positive posture state detection by posture state module 41.

Figure 3:
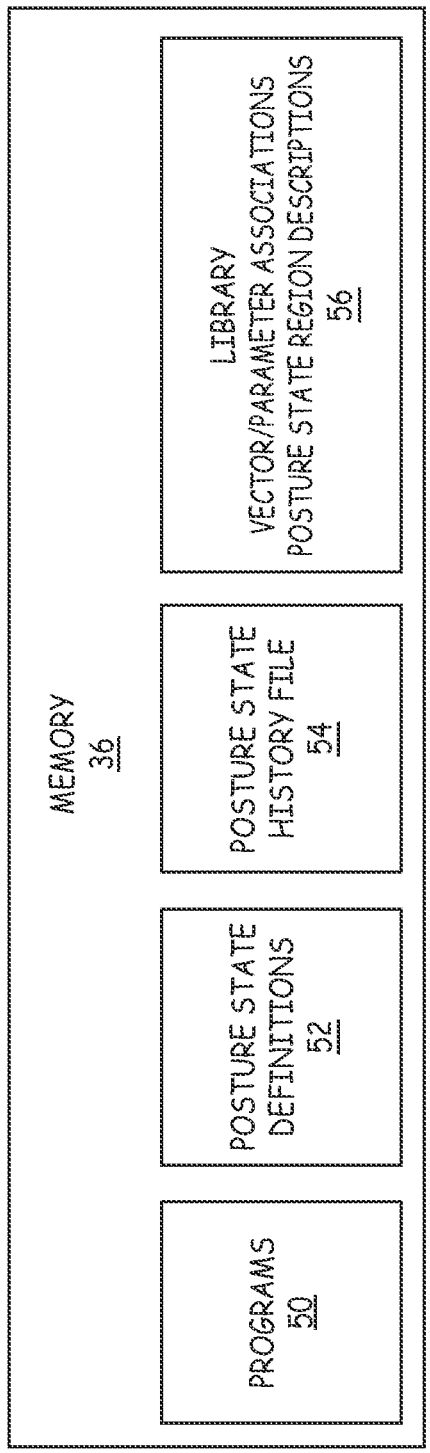
FIG. 3 is a block diagram illustrating an exemplary configuration of a memory of an implantable medical device according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to create posture state definitions 52. As discussed above, each posture state definition 52 is associated with at least one of a posture and an activity state.

A patient's posture state may be recorded in a posture state history file 54. This file may record, for instance, the patient's current posture information, including current posture and activity states as well as previous posture and activity states assumed by the patient over some period of time.

Memory 36 may also store a library 56 that contains vector/parameter associations and posture state region descriptions. This data structure is used to classify posture states of the patient in some embodiments, as will be discussed below.

In some cases, posture state information may be communicated to an external device such as an external monitor which is used to track a patient's condition. Alerts may also be transmitted in this manner. For example, a warning may be transmitted indicating that the patient has potentially taken a fall.

As discussed above, the signals of sensor 40 are used to detect a posture state. For purposes of this discussion, it will be assumed sensor 40 is a three-axis accelerometer, although sensor 40 could comprise multiple single-axis accelerometers instead, or be another type of sensor such as a gyroscope. Sensor 40 provides a respective signal describing acceleration along each of the x, y, and z axis. These axes will be assumed to be orthogonal.

Each of the x-, y-, and z-axis signals provided by sensor 40 has both a DC component and an AC component. The DC components describe the gravitational force exerted upon the sensor, and can thereby be used to determine orientation of the sensor within the gravitational field of the earth. According to the current disclosure, the orientation of the sensor remains relatively fixed with respect to the patient such that the DC components of the x, y and z signals may be utilized to determine the patient's orientation within the gravitational field, and to thereby determine the posture of the patient.

Prior art mechanisms generally utilize a patient's body coordinate system when determining posture. A body coordinate system may include the superior-inferior (S-I) body axis (extending toe to head), the anterior-posterior (A-P) body axis (extending back to front), and the lateral-medial (L-M) body axis (extending right to left). Postures may be readily defined in terms of these body coordinate axes.

In a simple scenario, a sensor 40 may be positioned within, or otherwise disposed in relation to, a patient such that the x, y, and z axes of sensor 40 are aligned with the patient's body coordinate system. In one example, the y axis of sensor 40 may be aligned with the patient's superior-inferior (S-I) body axis, the z axis of sensor 40 may be aligned with the anterior-posterior (A-P) body axis, and the x axis of sensor 40 may be aligned with the lateral-medial (L-M) body axis. When such an alignment between the sensor coordinate system and body coordinate system can be achieved, the sensor signals may be readily used to detect a posture state that is defined in terms of the body coordinate system. However, such alignment may be difficult to achieve and maintain. For instance, sensor position may shift while it is being carried within, or on, the patient.

Another approach to posture classification involves using a correction factor that takes into account that sensor 40 may not be aligned with the body coordinate system. This correction factor, which is used to translate sensor output into the body coordinate system, may be expressed in several ways. For instance, the correction factor may be a transfer matrix that is applied to the sensor output. Alternatively, the correction factor may include pitch, roll and yaw angles that are applied to the sensor signals to perform this transformation. Other mechanisms are possible for expressing the correction factor. According to this approach, the sensor signals may only be used to detect posture after the correction factor is applied and the signals have been expressed in terms of the patient's body coordinate system.

Mechanisms for applying correction factors are provided, for example, in commonly-assigned U.S. Pat. No. 6,044,297 entitled "Posture and Device Orientation and Calibration for Implantable Medical Devices". A further discussion of use of correction factors is provided in U.S. patent application Ser. No. 12/433,004 filed Apr. 30, 2009 referenced above. This application of the correction factor to a sensor output may be processing intensive.

Moreover, the correction factors must be initially determined. In an IMD that will perform posture classification on a regular basis, it may be desirable to eliminate these steps to conserve power and allow posture state classification to be performed more quickly.

Techniques described in the current disclosure define postures in the coordinate system of the sensor rather than in the patient's body coordinate system. Therefore, there is no correction factor that need be applied to the output of sensor 40. Moreover, the correction factors do not need to be derived. This dramatically simplifies the process of performing posture detection, and thereby saves a significant amount of power and processing time. This is particularly important for devices such as IMDs that have a limited power supply (e.g., rechargeable or non-rechargeable batteries).

To define postures in the coordinate system of the sensor, sensor 40 is positioned on, or in, patient 14 in any orientation in a substantially fixed manner. For instance, the sensor may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensor relative to the patient is substantially unchanging, at least over some period of time during which posture classification will occur.

Once the sensor is disposed in relation to the patient's body, the patient may be asked to temporarily assume a posture. Outputs from sensor 40 are obtained while the patient is in the assumed posture. In the case of a three-axis accelerometer, these outputs define a vector in three-dimensional space that may, in one embodiment, be expressed in terms of the coordinate system of sensor 40 without regard to the coordinate system of the patient's body. This vector that is defined by the output of sensor 40 may be any vector in three-dimensional space.

Next, the vector, which may be referred to as a defined posture vector, is associated with the posture state that the patient has been asked to assume. This association may occur by storing the defined posture vector or some representation thereof with a designation that identifies the posture state. Such an association may be stored within a table or some other aggregation of data shown as posture state definition 52 of FIG. 3.

The patient may be asked to assume any number of posture states in the foregoing manner. As each posture state is assumed, signals are obtained from sensor 40 that are indicative of a defined posture vector that is, in one embodiment, expressed in the coordinate system of sensor 40 without regard to the coordinate system of the patient. The defined posture vector or a representation thereof is associated with the posture state under definition.

After a defined posture vector is associated with a posture state, a tolerance may be selected. This tolerance defines a relationship to the defined posture vector. This relationship may describe a cone, a toroid, or some other region that surrounds or is otherwise disposed in relation to the posture vector, as will be described further below. Like the defined posture vector, this selected tolerance is associated with the posture state. Together, the defined posture vector and the tolerance will be used to determine whether a patient has assumed the associated posture state.

A patient may use a programming device such as clinician programming device 20 to define a posture state. For instance, a user may issue a command via programming device 20 to IMD 12 when a patient has assumed a desired position. This command causes IMD 12 to obtain signal values from sensor 40, which are optionally processed by posture state module 41 of IMD and stored in memory 36. These sensor signals may also be uplinked via telemetry circuitry 38 to an external device such as programming device 20 to undergo some of the processing steps. The captured sensor signals may be associated with an indication (e.g., an alpha-numeric tag, a binary tag, etc.) identifying a posture state as specified by a user employing programming device 20. Such an indication may be provided using display 22, keypad 24, a touch screen, a peripheral pointing device, and/or other types of user interface mechanisms, as described above. A user interface such as a graphical user interface may be employed during this process. A tolerance may likewise be specified by the user for association with this posture state definition. The association may be stored in memory of programming device 20, in memory 36 of IMD 12, or in some other storage facility. Techniques for defining a posture vector and creating the above-described associations are described in patent application Ser. No. 12/432,993 filed Apr. 30, 2009 entitled "Posture State Classification for a Medical Device" referenced above and incorporated herein by reference in its entirety.

In the foregoing manner, one or more posture states may be defined. Each such posture state is associated with a vector and a tolerance. These defined posture states may then be used to classify a patient's positions and movements. As a patient changes activity level and/or assumes a new position, outputs from sensor 40 are employed to obtain a currently-detected vector that describes the patient's current posture state. In one embodiment, this detected posture vector, like the defined posture vector, is expressed in terms of the sensor coordinate system without regard to the patient coordinate system. For this reason, the detected posture vector may be compared directly to one or more of the defined posture vectors without the need to apply a correction factor to the detected posture vector. This comparison indicates whether the detected posture vector has a relationship to any of the defined posture vectors that is specified by an associated tolerance.

As an example, assume a tolerance describes a cone surrounding a defined posture vector and indicates that the detected posture vector must lie within the cone to satisfy the requirements of the definition. The comparison step will determine whether the detected posture vector lies within the cone. If so, the patient may be classified as occupying the associated posture state.

As previously mentioned, if the detected posture vector and the defined posture vectors are expressed in terms of the sensor coordinate system without regard to the patient coordinate system, this classification step does not involve applying any correction factor to the detected posture vector. A direct comparison may be performed between the detected and the defined posture vectors because both vectors are described in terms of the sensor coordinate system. This comparison may be completed in a manner that is not processing intensive and does not require a large expenditure of system resources.

Figure 4:
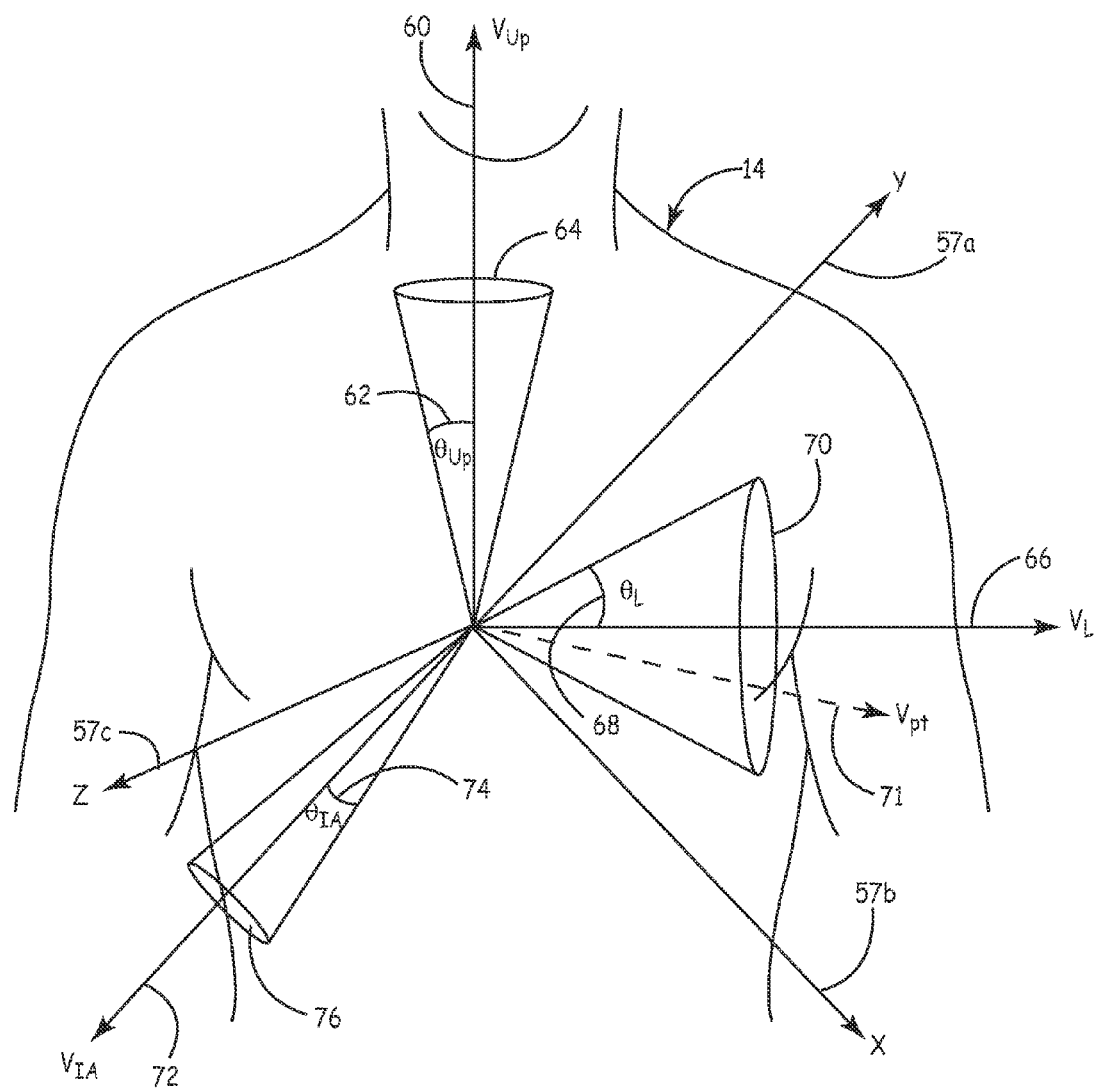
FIG. 4 is a graph illustrating one example method of posture definition.

FIG. 4 is a three dimensional graph illustrating one method of defining posture states using sensor 40. Sensor 40 (not shown) is disposed in a substantially fixed manner relative to patient 14. The coordinate system of sensor 40 includes y axis 57a, x axis 57b, and z axis 57c. As described previously, in one embodiment, this sensor coordinate system need not be orientated in any particular manner relative to patient 14 or the patient's body coordinate system 58.

When it is known that patient 14 is in an upright position, sensor 40 will provide outputs that can be processed to obtain a vector $[V_1, V_2, V_3]$ which is shown as $V_{Up}$ 60. For purposes of this disclosure, this vector and similar vectors are described using a notation wherein the first vector component (e.g., $V_1$) may correspond to an x-axis component of the vector, the second vector component (e.g., $V_2$) may correspond to a y-axis component of the vector, and the third vector component (e.g., $V_3$) may correspond to a z-axis component of the vector.

Vector $[V_1, V_2, V_3]$ may be associated with an Upright posture, as by storing some indication of this posture along with one or more values identifying the vector. A tolerance may then be selected for this posture that describes a relationship to vector $V_{Up}$. In the current example, the tolerance relates to a cone 64 defined by an angle $\theta_{Up}$ 62. For purposes of this posture definition, the cone identifies a maximum distance from vector $V_{Up}$. So long as a patient's detected posture vector lies within this cone, the patient will be considered to be in the Upright posture. Thus, the patient may be leaning slightly forward, backward, or sideways from the vector $V_{Up}$, but may never-the-less be categorized as standing so long as the detected posture vector lies within cone 64.

Posture vector $V_{Up}$ 60, the predetermined angle $\theta_{Up}$ 62, and some description of the relationship to be identified by the tolerance (e.g., "within the cone") may be associated with the Upright posture for use in later classifying a patient's posture.

This may involve storing this information as one of posture state definitions 52 (FIG. 3) in memory 36.

In a similar manner, other posture vectors may be defined. For instance, a vector $V_L$ 66 may be defined that will be used to determine a Lying Left posture state in which the patient 14 will be classified when he is lying on his left side. In a manner similar to that described above, a tolerance is defined for this vector that may involve a cone 70 having a size indicated by angle 68. As with the Upright posture state, this cone indicates a maximum distance from $V_L$ 66. When a detected posture vector lies within this posture cone 70, the patient 14 will be classified as lying on his left side. This will be the case for detected posture vector $V_{pt}$ 71, which is shown to be within cone 70.

Any other one or more posture states may be defined in a similar manner. As one example, a vector $V_{LA}$ 72 may be associated with a posture state that a patient may assume when lying face down with his head somewhat below his feet. A tolerance may be selected for this posture state that involves a cone 76 defined by angle $\theta_{LA}$ 74. If a detected posture vector lies within this cone, the patient will be classified as occupying this posture.

Some space may not be included within any posture state definition. For instance, in this illustration, space outside of cones 64, 70 and 76 is excluded from a posture state definition. This space represents an unclassified posture state. In one embodiment, if a detected posture vector falls within this space, the patient is categorized as being in an Unclassified posture state. In one example embodiment, when this classification is made, no actions are initiated. For instance, the therapy that was delivered to the patient before the patient was categorized in the Unclassified posture state will continue to be delivered to the patient after this classification.

In another similar embodiment, when a detected posture vector falls within the space that represents an unclassified (or previously undefined) posture state, the patient's posture state may remain classified as it was prior to the time the patient's detected posture vector entered this space. For instance, if the patient was previously classified as being in the Upright posture state, the patient may remain classified in the Upright posture state after the detected posture vector transitions into the space that is not associated with a defined posture state. As a practical matter, this embodiment is substantially the same as that described in the foregoing parameter, since in either case, operation of the IMD 12 continues as it was prior to the transition. In this example, therapy parameters associated with the Upright posture state may continue to be used to deliver therapy to the patient.

In either of the foregoing embodiments, the space outside of that which is associated with a defined posture state may be referred to as "hysteresis space" since it adds hysteresis to the system. The size of this space will vary depending on the number of posture state definitions in use within the system, as well as the size of the tolerance associated with each posture state definition.

In yet another example embodiment, the hysteresis space may be associated with one or more actions. For instance, a therapy may be associated with the spatial region outside of any defined posture state. When the patient enters this hysteresis space, therapy delivery may be modified so that the patient receives therapy according to parameters associated with the hysteresis space. In one case, this therapy may be chosen to be "benign", such as a therapy that delivers stimulation having a relatively low amplitude, for instance. Any other one or more therapy parameters or other actions (e.g., storing of data, notification generation, communication initiation, etc.) may be associated with hysteresis space such that the associated action is initiated when the patient is not classified in any of the previously-defined posture states.

According to other scenarios, the posture state definitions may not be mutually exclusive. For instance, although none of the areas of cones 64, 70 and 76 overlap in FIG. 4, overlap of areas associated with different posture state definitions is possible in another embodiment. If such overlap exists, it is possible for a patient to be classified as being in more than one posture state at once. In such embodiments, it may be necessary to determine which posture state takes precedence when determining the parameters that will be used to control therapy delivery or another aspect of operation of IMD 12.

In the foregoing manner, any vector may be selected for use in defining a posture state. Each defined posture state vector need not be in any particular plane or have any predetermined relationship to any other defined posture vector. As another example, a vector of an Upright posture state need not be orthogonal to a vector for a Lying Left or a Lying Right posture state. Moreover, vectors associated with posture states associated with a patient's reclining positions (e.g., Lying Right, Lying Left, Lying Forward, Lying Back, etc.) need not be co-planar. As still another illustration, a Lying Right posture state defined to describe a patient lying on his right side need have no particular relationship to the Lying Left posture state associated with the patient lying on his left side.

Using the techniques described above, posture definitions may be created that are specific to a particular patient's activities and/or profession. For instance, a bank teller may spend a significant portion of his working day leaning forward at a particular angle. Therefore, sensor 40 may be used to obtain a defined posture vector that is specific to this Leaning posture state. Similarly, a tolerance may be selected for this posture state definition that is specific to the particular patient. Thereafter, classification of the patient's position in this Leaning posture state may be used to trigger delivery of therapy, recordation of patient information and/or some other type of action. As previously discussed, in one embodiment, all defined posture vectors may be defined in the coordinate system of sensor 40 and without regard to a patient's body coordinate system to provide for efficient posture state classification.

All of the above examples of posture state definitions describe a cone. The size of a cone may be described by an angle of the cone. For instance, the size of cone 64 is described by angle $\theta_{Up}$ 62. While the angles may be selected to be of any size, in one embodiment, angles may be generally between approximately 1° and approximately 70°. In other examples, cone angles may be between approximately 10° and approximately 30°. In some examples shown in FIG. 4, the cone angles are approximately 20°.

Another way to specify a cone is by selecting a radius of a base of a cone relative to a center vector or axis. This radius may, but need not, be symmetrical about the associated defined posture vector. In the example shown in FIG. 4, cones 64, 70, and 76 each has rotational symmetry about the respective center axis 60, 66, and 72. Thus, FIG. 4 illustrates cones in which center lines 60, 66, and 72 pass perpendicularly through the centers of the respective base. In other examples, center lines 60, 66, 72 need not pass perpendicularly through the centers of the respective base. Thus, in the case of tolerances that describe cones, the cones may be any one of multiple possible configurations.

When posture state definitions reference cones, a definition may indicate that the patient will be classified as occupying the posture state when the patient's detected posture vector is within the cone (i.e., the detected posture vector is no more than the maximum distance described by the cone from the defined posture vector). However, this need not be the case, and the patient may instead be classified as occupying an associated posture if a sensor reading is outside of (rather than inside of) a cone as described in reference to FIG. 4.

Figure 5:
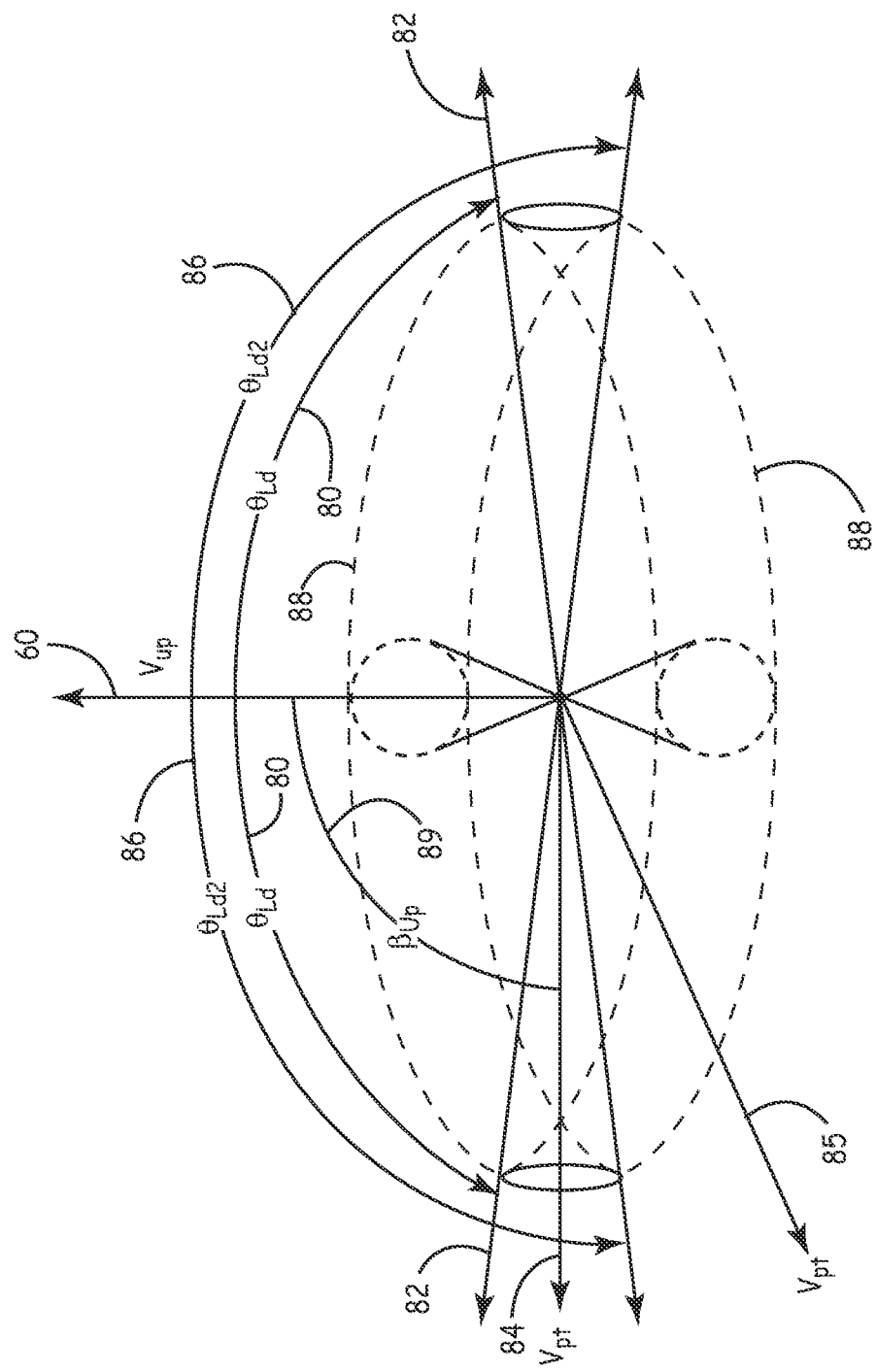
FIG. 5 is a graph illustrating another method of posture definition.

FIG. 5 is a graph illustrating another example relationship that may be used to create posture state definitions. A posture state may be defined using vector $V_{Up}$ 60 and an angle $\theta_{Ld}$ 80 that defines a minimum (rather than a maximum) distance from vector $V_{Up}$ 60. A patient may be classified as occupying this posture if the detected posture vector is farther away from the defined posture vector $V_{Up}$ 60 than the angle $\theta_{Ld}$ 80 (i.e., lies outside of a cone 82). This type of definition may be used to define a Lying Down posture, for instance. According to this example, both of detected posture vectors $V_{pt}$ 84 and $V_{pt}$ 85 will be classified as being in this Lying Down posture since both vectors are outside of cone 82 that surrounds $V_{Up}$ 60.

In yet another example of a posture state definition, two angles, $\theta_{Ld}$ 80 and $\theta_{Ld2}$ 86, may be used in conjunction with the defined posture vector $V_{Up}$ 60 to express a tolerance. For example, these two angles may be selected to describe a toroid 88 (shown dashed) that surrounds the posture vector $V_{Up}$. A patient may be classified as occupying the defined posture state if the detected posture vector lies within this toroid. In this case, a patient associated with detected posture vector $V_{pt}$ 84 is classified as being in the Lying Down posture state since this posture vector lies within toroid 88. However, a patient associated with vector $V_{pt}$ 85 is not classified as being in the Lying Down posture state, since this detected posture vector is outside of toroid 88.

As yet another example, multiple vectors and multiple tolerances may be referenced in a single posture state definition. For instance, two defined posture vectors, each being associated with respective tolerances, may describe two cones in three-dimensional space. These cones may both be used to define a posture state. That is, a posture state definition may specify that the area within either one, or both, of the cones is included in the definition. This corresponds to an OR-type logic function (e.g., such as a Boolean Logic function). As another example, the definition may specify that only an area that resides in both of two overlapping cones in included in the definition. This corresponds to an AND-type logic function. Another illustration involves specifying that only the area in one, but not the other, of two overlapping cones is included in the definition. This type of operation utilizes both AND-and NOT-type logical functions.

According to another embodiment, a definition may reference one or more toroids and/or one or more cones. These regions may, or may not, overlap. A posture state definition may be created that references multiple ones of these regions, and that may further utilize logic functions (e.g., OR, AND, NOT, etc.) to indicate which portions of these regions are to be associated with a particular posture state definition. Thus, it will be understood multiple regions in space may be referenced by a single posture state definition. When multiple regions are involved, any logic function (e.g., of a Boolean type, etc.) known in the art may be used to define relationships indicating which portions of which regions are included in the posture state definitions. Techniques for creating posture state definitions using multiple regions in three-dimensional space are described in commonly-assigned patent application Ser. No. 12/432,993 filed Apr. 30, 2009 referenced above.

The foregoing focuses primarily on techniques for defining posture state definitions, as by using posture vectors and spatial regions defined relative to these vectors. After such a definition is created, classification occurs by determining whether a patient's currently-detected posture state meets the requirements of the definition. This may involve, for instance, determining whether a detected posture vector that describes the patient's current posture lies within a cone referenced by an existing posture state definition, as exemplified by FIG. 4. Such a determination may be made by determining an angle between the detected posture vector and the defined posture vector. If the posture state definition includes the space within a cone surrounding the defined posture vector, the patient may be classified as occupying the associated posture state if the angle between the detected posture vector and the defined posture vector is less than the angle defining the cone. Another way to make this determination that is far less processing intensive because it does not involve derivations of angles involves comparing a sine or a cosine of the angle between the patient's detected posture vector and the defined posture vector. Other mechanisms are available for classifying a patient's posture state using previously-defined posture state definitions, as described in the U.S. patent applications having Ser. Nos. 12/432,993 and 12/433,004 referenced above.

As may be appreciated, during classification of a patient's posture state, it is important that sensor 40 be maintained in substantially the same position relative to the patient that existed when the posture state definitions were originally obtained. This will allow the same sensor coordinate system that was used when defining the posture states to likewise be used when classifying a patient's positions.

If the sensor orientation relative to the patient changes, as may occur if an IMD 12 rotates with respect to patient 14, the posture state definitions must be recalibrated. This may be performed manually by again obtaining and re-recording vectors that are each associated with each defined posture state. Such vectors are described in the coordinate system of sensor 40. Techniques for recalibrating posture vectors manually are described in commonly-assigned patent application Ser. No. 12/433,623 filed Apr. 30, 2009 and incorporated herein by reference.

The foregoing describes mechanisms for initially defining posture states that include a reference to a posture vector, and further mentions the need for subsequent re-calibration of posture vectors. In both cases, the selection of a posture vector that is associated with a given posture state definition may be performed in a completely manual way. That is, the patient may be asked to assume any number of posture states contained within a predetermined set of posture states (e.g., standing upright, lying on a right side, lying on a left side, lying on his back, lying face down, reclining backwards in a lounge chair, etc.) As each posture state is assumed, signals are obtained from sensor 40 that are indicative of a defined posture vector. That vector, which is indicative of the associated posture state, may then be associated with a posture state definition. A more automated mechanism for obtaining the posture vectors for use in creating posture state definitions is described below.

Figures 6A, 6B:
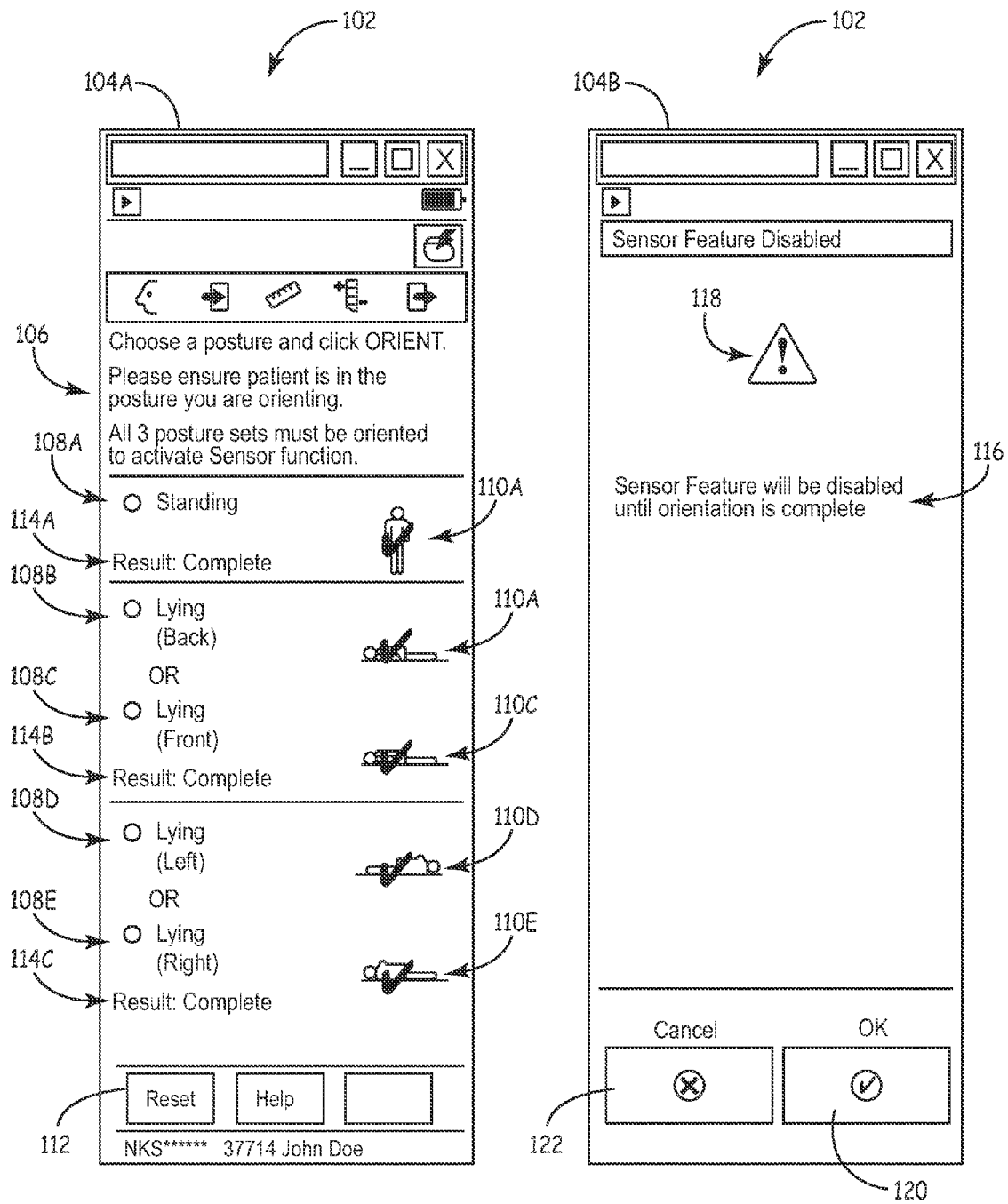
FIGS. 6A and 6B are conceptual diagrams illustrating example screens that may be displayed by a user interface to allow a user to redefine one or more posture cones of a patient.

FIGS. 6A and 6B are conceptual diagrams illustrating example screens that may be displayed by a user interface to allow a user to define or redefine one or more predetermined posture states that are supported by the system. Such a user interface may be provided on programmer 20, which may be a clinician programmer or some other programmer.

Screen 104A of FIG. 6A may be presented to a user to define each of five predetermined posture states. This screen may be presented after the user has communicated to clinician programmer 20 a desire to perform posture state definition or recalibration e.g., by selecting a posture state definition icon from a drop down menu or an icon contained on another screen. Alternatively, screen 104A may be presented automatically by programmer 20 if it is determined, e.g., by IMD 12 or programmer 20, that the posture state sensor of IMD 12 has become disoriented. If it has been determined that sensor 40 has likely become disoriented, IMD 12 may automatically suspend the delivery of therapy according to detected posture states. In such an example, patient 14 may be required to navigate through screens 104A-104B to perform re-calibration before IMD 12 resumes the delivery of stimulation or other therapy in a manner that is responsive to the detected posture states of patient 14.

Screen 104A includes instructions text 106 which may display one or more instructions or information to a user with respect to the definition or recalibration process. In this example, instructions text 106 instructs the user how to carry out the definition process. In particular, instructions text 106 instructs a user to "Choose a posture and click ORIENT". Further, instructions text 106 conveys to the user that patient 14 should be in the posture that is being oriented, i.e., defined, according to the posture sensor data generated by the posture state sensor at that time.

Furthermore, in the embodiment of FIGS. 6A and 6B, instructions text 106 conveys to the user that all three posture sets must be oriented to activate the posture state sensor function. In this example, "Sensor function" may refer to the automatic delivery of therapy by IMD 12 based on the detected posture state of patient 14 using the respective posture cones. In this embodiment, IMD 12 is configured to prompt the user for a "Standing", a "Lying (Back)", a "Lying (Front)", a "Lying (Left), and a "Lying (Right)" posture state definition. Accordingly, user interface 104A indicates instructions consistent with this configuration to the user via instructions text 106.

Screen 104A further includes posture selection items 108A-108E (collectively "posture selection items 108"), which correspond to the posture states of "Standing," "Lying (Back)," "Lying (Front)," "Lying (Left)," and "Lying (Right)," respectively. A user such as a clinician may use posture selection items 108A-108E to select the posture state that patient is occupying or will be occupying such that the vector for that posture state may be initially defined or subsequently redefined. For example, a user may instruct patient 14 to lie on his or her back. Once patient 14 is lying on his or her back, the user may communicate that they would like to define the "Lying (Back)" posture vector by selecting posture selection item 108B, e.g., by clicking next to the posture description with a stylus or other input media.

Screen 104A further includes posture state status indicators 114A-114C to indicate to the user the status of required posture states or group of posture states with respect to the definition process. For example, posture state status indicator 114B corresponds to the two posture cones defining the "Lying (Back)" and "Lying (Front)" posture states, the definition of which is indicated as being "Complete." This means that the posture vectors have been defined for each posture state in this group.

Screen 104A also includes posture state status icons 110A-110E. Each respective icon has a graphical component illustrating the posture state to which a respective posture icon is related. For instance, icon 110A includes a graphical component illustrating a human in a standing posture state. Icons 110A-110E correspond to the five predetermined posture states previously described. Icons 110A-110E indicate whether a posture vector is defined and active for each posture state, not just for each posture group, as with indicators 114A-114C. In this case, user interface 102 indicates to the user that a posture vector is defined for a respective posture state by superimposing a "check-mark" over each posture state illustration. As shown in FIG. 6A, posture state indicators 110A-110E indicate that all defined posture vectors have been determined for all five example posture states.

Screen 104A also includes Reset button 112. To redefine the existing posture vectors, a user may select this Reset button 112, which causes user to navigate from screen 104A to screen 104B. Screen 104B allows programmer 20 to confirm that the user desires to proceed with the posture redefinition process for the posture state selected in screen 104A. Screen 104B includes text section 116 and warning icon 118. Text section 116 includes textual information informing the user that the proposed action will suspend the delivery of therapy based on the detected posture state of patient by IMD 12. Warning icon 118 alerts the user to the relative importance of the action about to be undertaken. If the user wishes to continue with the redefinition process, the "OK" button 120 on screen 104B may be selected. At that point, programmer 20 will suspend the delivery of stimulation by IMD 12 to patient 14 based on the detected posture state. Conversely, if the user elects to abort the redefinition process, the user may select "Cancel" button 122 on screen 104B. At that point, programmer 20 may return to a default screen or indicate to the user that the redefinition process was aborted and that IMD 12 will continue to deliver posture-responsive therapy based on the posture state detected using the existing posture vectors. Use of the Reset button 112 may be employed when it is known that the existing posture vectors are to be manually recalibrated, as may occur because IMD 12 has shifted position within patient 14, because the patient's postures are changing, or for some other reason.

In the examples of FIGS. 6A and 6B, the user interface is described in terms of selection of posture vectors only, without illustrating a mechanism for entering a tolerance (e.g., a cone size.) In a simplistic system, each tolerance may be predetermined for each posture state. For instance, each posture state may be defined in terms of a selected vector and a cone surrounding that vector, wherein the cone is of a predetermined size. That size may be the same as, or different from, a size of another cone for another posture state definition.

In another embodiment, a user is allowed to select the tolerance. For instance, a clinician may graphically indicate the boundaries of a tolerance (e.g., a cone) directly on a user interface of programmer 20. For example, the clinician could draw a spatial region such as a cone with a stylus or other pointing or drawing tool in conjunction with a touch screen on programmer 20. The clinician could draw the cone or simply draw a ray to represent a central reference vector of the cone. In this case, programmer 20 could automatically apply a tolerance angle to the reference vector to define the cone. In some cases, the clinician could identify the tolerance angle.

Upon creating the posture state definition, the clinician could view the result, either as a final result or a preliminary result that requires patient confirmation for execution. In particular, programmer 20 may be configured to present an illustration of the cone to the user.

In some examples, a clinician may be permitted to copy and paste an existing cone or other spatial region to create a new region, or drag and drop an existing region into a different region. Also, programmer 20 may be configured to permit the patient to resize existing regions such as cones by redefining angles or by manipulating one or more handles or other control points on an existing region or new region to expand or shrink that space or a corresponding tolerance angle. As an example, a cone may have control points associated with rays defining the outer surface of the cone, as a function of cone angle.

By dragging the control points with a stylus or other pointing device in a given direction, a clinician may increase or reduce the cone tolerance angle. In some cases, a clinician may manipulate a control point on one side of the cone to expand or shrink the cone angle in a symmetrical manner about the reference vector. Dragging and dropping, copying and pasting, expanding and shrinking, rotating, tilting, and other graphical utility operations may be used to create new cones, or resize new or existing cones. As an illustration, a clinician could "click" on an upright cone and specify a copy operation, and drag a copy of the cone to a desired location, possibly rotating the cone to a desired position.

As another example, programmer 20 may provide a drop down menu that provides numerous graphical operations that can be chosen by the clinician, such as cone shrinking, cone enlarging, or other operations. In some cases, a drop-down menu may permit a clinician to select different cone or cone angle sizes, such as small, medium or large. A variety of graphical utilities may be provided to the clinician via programmer 20 to permit the clinician to flexibly and conveniently customize posture state definitions by modifying existing cones or adding new cones of desired sizes and positions. Although cones are described for purposes of illustration, other types of spatial regions may be suitable for graphical manipulation and definition, as discussed above.

Alternatively or additionally, the user may be allowed to enter via a text box a description of a tolerance, as by entering some type of equation that describes a spatial relationship with the selected posture vector. Thus, many input mechanisms are possible for defining a spatial relationship relative to a selected posture vector for use in defining a posture state definition. It will be understood that the user interface of FIGS. 6A and 6B, which is described in terms of selection of posture vectors only, is for illustration, and is not to be considered limiting.

Figure 7:
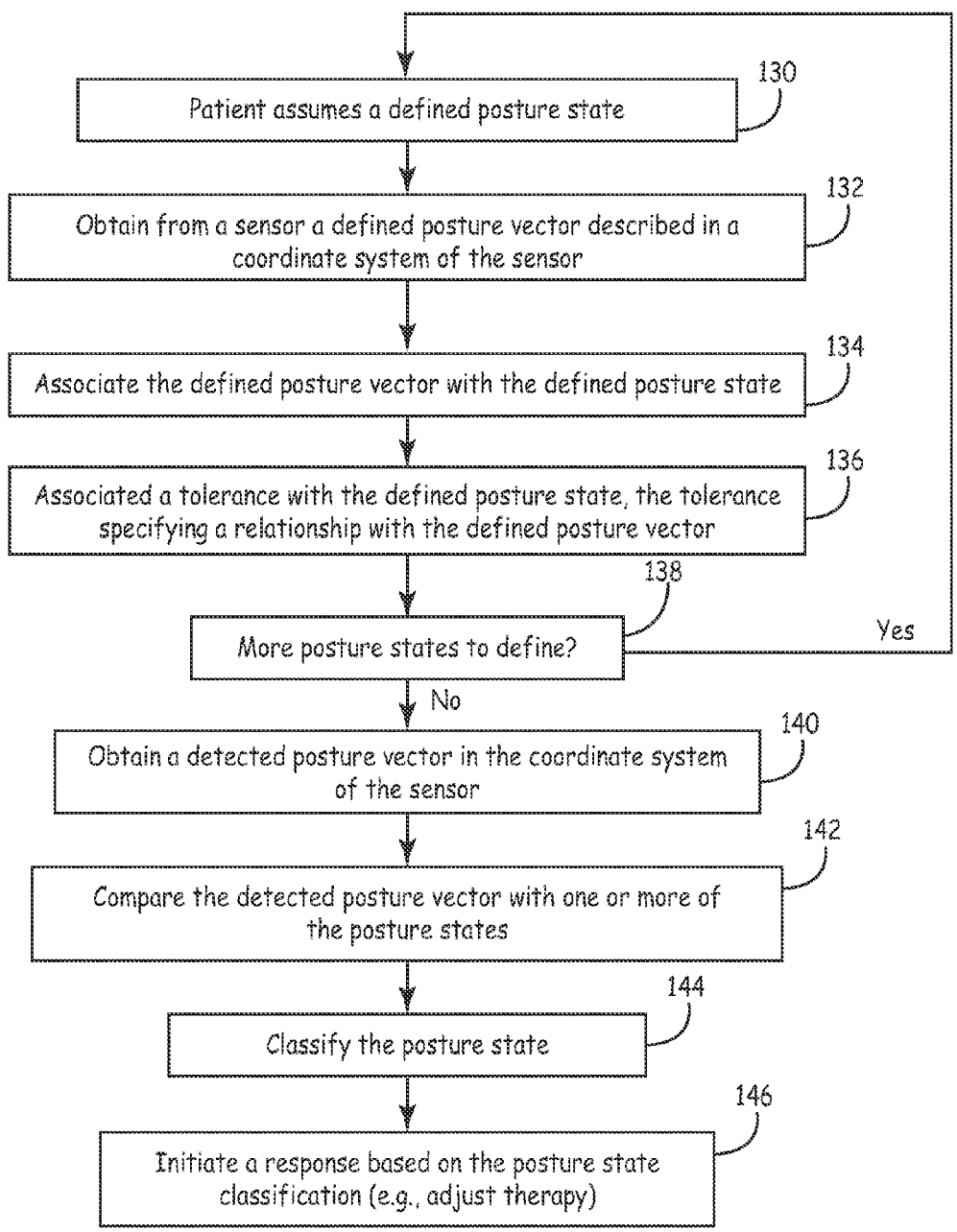
FIG. 7 is a flow diagram describing one method of creating and using posture definitions according to the current disclosure.

FIG. 7 is a flow diagram describing one method of defining posture state definitions and using these definitions to classify a patient's posture state according to one embodiment of the current disclosure. As discussed above, a posture state involves at least one of a posture and/or an activity level. However, for purposes of the discussion concerning FIG. 7, it is assumed that the posture state will involve a posture.

First, a patient is directed to assume a posture state (130). This may be any posture state whatsoever. While the patient assumes the posture state, a defined posture vector is obtained from sensor 40. As discussed above, in one embodiment the defined posture vector is described in a coordinate system of the sensor rather than in terms of a patient's body coordinate system (132). The defined posture vector is associated with the defined posture state (134). This may be accomplished by storing an indication of the defined posture state along with an indication of the defined posture vector, for example.

A tolerance is also associated with the defined posture state (136). This tolerance specifies a relationship with the defined posture vector. This relationship may be expressed in terms of one or more regions in space (e.g., cone(s), toroid(s), etc.) positioned relative to a defined posture vector. The regions may be described in multiple ways, as discussed above. Mechanisms for describing these regions may include use of angles, a straight-line distance, a city-block distance, a mathematical relationship such as one that involves trigonometric functions or inner products, and so on. The relationship may further involve a minimum (e.g., "falls within"), a maximum (e.g., "falls outside of"), and/or some type of logic function (e.g., Boolean logic). The association of the tolerance may be accomplished by storing the tolerance and the defined posture vector with an indication of the posture state. If any more posture states are to be defined (138), the definition process is repeated by returning to step 130.

After one or more posture states are defined in the foregoing manner, processing continues to step 140, where a detected posture vector describing a current posture state of a patient is obtained. This detected posture vector is obtained from sensor 40 in the coordinate system of the sensor according to this embodiment. The detected posture vector is compare with one or more of the posture state definitions to determine whether this detected posture vector has a specified relationship with a defined posture vector as set forth by any of the posture state definitions (142). The patient's posture state is then classified based on this determination (144). Some response may be initiated based on this posture state classification, such as to adjust therapy, provide a notification, or to take some other action (146). In one particular embodiment, one or more therapy parameters (e.g., stimulation current or voltage amplitude, pulse width, electrode combination(s), electrode polarities, duty cycle, stimulation waveform shape, programs, program groups, substantial bolus amounts, etc.) are associated with the posture state definition, and classification of the patient in a posture state results in delivery of therapy to the patient according to the therapy parameters associated with the posture state.

It is possible that the detected posture vector does not have a specified relationship with any of the defined posture states in step 142. In this case, the patient's posture state may be classified as Unclassified and the desired actions associated with the Unclassified posture state classification may be initiated (e.g., a therapy associated with the Unclassified posture state may be delivered to the patient.) In another embodiment, when this occurs, the posture state classification in which the patient was last classified and which is associated with a defined posture state is retained. As an example of this latter embodiment, if a patient who was most recently in the Upright posture state assumes a pose that is not associated with a defined posture state, the patient may remain classified as Upright and therapy and other operational parameters associated with the Upright posture state may remain in use.

In the above discussion, including the description of the method of FIG. 7, posture states are defined, and may thereafter be recalibrated, by having the patient assume a posture state. An output of sensor 40 may be captured, stored, and associated with a posture state definition. Having the patient assume each posture state in this manner may be tedious for the patient, and may consume a clinician's valuable time. To streamline this process, at least a portion of the initial definition and any required re-calibration may be performed completely automatically. This automatic definition and re-calibration process will be described in the following paragraphs using a sensor 40 which is a three-axis accelerometer. This sensor 40 will be illustrated as being housed within IMD 12. However, it will be understood that the described mechanisms may be adapted for use with any of the alternative embodiments described herein, including external devices that may be worn by the patient, and sensors that are other than three-axis accelerometers.

According to one embodiment, IMD 12 is assumed to have at least one major surface. When IMD 12 is implanted within patient 14, this major surface will generally be positioned in a substantially parallel fashion to an exterior surface of patient 14. For illustration, assume IMD 12 has a shape somewhat akin to a coin, such as a fifty-cent piece. The IMD 12 will have two major surfaces (i.e., "heads" and "tails" surfaces of the coin). When implanted, both of these surfaces may generally be positioned substantially parallel to a body surface of the patient, such as the cutaneous boundary of the patient's torso. It will be assumed that the IMD 12 will not typically intentionally be positioned so that the major surfaces are facing the sides of the patient.

It will further be assumed that IMD 12 has a major surface that is intended to be positioned closest to the cutaneous boundary when the device is implanted within patient 14. This major surface may be referred to as the reference surface, or face, of the IMD 12. This surface may be indicated by a "This Side Up" directive stamped on that face of the IMD 12, or otherwise indicated in association with the device. For instance, this will be the side that is visible to the clinician after the device is inserted within the surgical pocket and before the pocket is closed. This reference face of the IMD 12 will be assumed to be roughly parallel to the cutaneous boundary of the patient's torso, as discussed above.

Figure 8A:
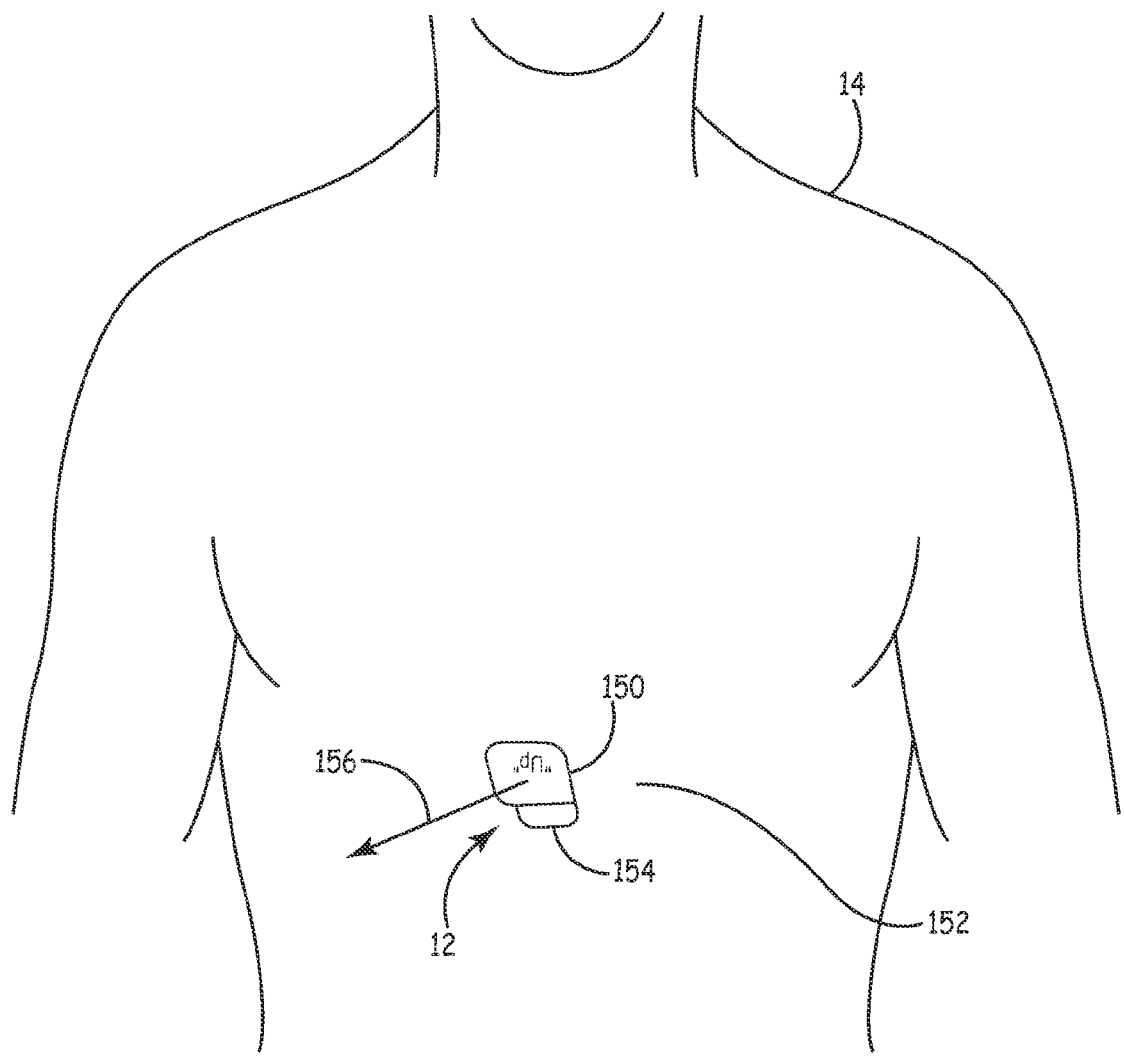
FIG. 8A is a conceptual diagram of an implantable medical device implanted within a patient.

FIG. 8A is a conceptual diagram of IMD 12 implanted within patient 14. Reference face 150 is visible, indicating that this side is closest to the cutaneous boundary of torso 152 of patient 14. It will be appreciated that while reference face 150 is substantially parallel to cutaneous boundary of torso 152, other aspects of the orientation need not be determined. For instance, IMD 12 may be rotated in any manner within pocket, as shown by FIG. 8A, which illustrates connector block 154 facing downward away from the head of patient 14 in what may be considered an "up-side-down" orientation. This is further indicated by the "up-side-down" orientation of the "Up" directive which is printed on the reference face 150 of IMD 12. In another embodiment, the connector block 154 may be turned towards the patient's left or right side, or in some other skewed manner. Thus, no further assumptions are made concerning the orientation of IMD 12 other than that reference face is positioned towards the patient's cutaneous boundary and remains substantially parallel with that boundary of the torso during posture state calibration, which will occur sometime relatively soon after implantation of the device. This is generally a reasonable assumption, since clinicians are accustomed to placing the devices in this manner, and since it is natural for an IMD 12 to be retained within the pocket so that the reference face is substantially parallel to the cutaneous boundary of the patient, at least initially.

A reference vector 156 may be correlated with the reference face 150, as shown in FIG. 8A. In one embodiment, reference vector 156 is a vector that is perpendicular to reference face 150 and that extends outward from the patient's body when IMD 12 is implanted within patient 14 in the manner shown in FIG. 8A. This reference vector can be readily determined prior to implantation of IMD 12 by positioning IMD 12 on a level surface with reference face 150 facing upward so that it is visible. The resulting vector obtained from sensor 40 may be captured as the reference vector. This reference vector may be stored within a storage device of IMD 12 such as within memory 36, or may otherwise be recorded and/or stored by some other means for use during posture state calibration. When IMD 12 is implanted within patient 14 as shown in FIG. 8A, reference vector 156 will correspond roughly to a Lying Back posture vector, which is a vector that is obtained when the patient lies face up on his back.

Sometime after implantation of IMD 12 within patient 14, patient 14 will generally consult with a clinician during a programming session. Such a session will choose therapy parameters for delivery of therapy to the patient. Such a session may result in definition of, and/or selection of, programs for use in delivering therapy to the patient. For instance, IMD 12 may generate and deliver stimulation therapy according to one or more programs. A program defines values for one or more parameters that control an aspect of therapy delivery. For example, a program that controls delivery of stimulation by IMD 12 in the form of pulses may define a voltage or current pulse amplitude, a pulse width, and/or a pulse rate, for stimulation pulses delivered by IMD 12 according to that program.

Multiple programs may be selected for delivering therapy to a patient in a time-interleaved or a time-overlapped manner. For instance, IMD 12 may rotate through multiple selected programs when delivering stimulation such that numerous conditions of patient 14 are treated. Such a rotation may employ a program directed to leg pain, a program directed to lower back pain, and a program directed to abdomen pain, for example. In this manner, IMD 12 may treat different symptoms substantially simultaneously.

Other aspects of IMD 12 operation may be initialized during an initial programming session following the implantation procedure. In an embodiment wherein posture states are defined manually in the manner shown in FIG. 7, such a programming session may require the patient to assume a predetermined set of posture states that will be used to control therapy delivery and that may initiate other actions (e.g., generation of notifications, storing of data, etc.). As used herein, the predetermined set of posture states are posture states that are each associated with definitions requiring at least some degree of calibration before they are used to estimate a vector and/or tolerance value. That is, these posture state definitions are not created "on the fly" as the patient goes about daily life, but may require some type of calibration procedure to be performed. As previously discussed, requiring a patient to assume each one of the predetermined posture states within the system may be a time-consuming task that may be tedious and uncomfortable for the patient, especially if the patient is still recovering from surgery. Moreover, this consumes valuable time of the clinician.

According to the current disclosure, the process of requiring a patient to assume multiple inconvenient posture states is largely, if not completely, eliminated. Sometime during the programming session when the clinician observes that the patient is occupying something that approximates the Upright posture, the clinician may activate a calibration routine that will capture outputs of sensor 40. The captured vector will be associated with the Upright posture state. This calibration may be performed, for instance, by choosing selection item 108A on the user interface of FIG. 6A, and then activating the ORIENT button. In another streamlined approach, selection of the ORIENT button without making any other selections will cause the captured vector to be, by default, associated with the Upright posture vector.

If desired, the calibration process may be entirely transparent to the patient, who is not aware that the clinician is performing this calibration procedure. That is, the clinician may perform the process when it is observed that the patient is in a generally upright position. If the IMD 12 is implanted within the patient's torso, the calibration procedure may even be performed when the patient is seated in a substantially upright position, since the patient's torso will be in a relatively upright posture that is similar to that in which it would otherwise be positioned if the patient were standing. In yet another scenario, the clinician may give the patient warning, as by asking the patient to "sit up straight", or by requesting that the patient assume a typical upright pose prior to performing the calibration. In any event, the capturing of this estimated vector may be completed relatively quickly, and without the patient being required to assume any lying postures.

The vector that is captured during the foregoing streamlined calibration process may be referred to generally as a captured estimated vector, since it estimates or approximates the vector that corresponds to the patient's actual Upright posture state. Moreover, as discussed above, reference vector 156 may, in one embodiment, correspond roughly to a patient's lying back posture vector. Therefore, reference vector 156 may automatically be associated with the Lying Back posture state for use as the patient's estimated lying back vector. This estimated lying back vector correlates generally with a vector that would be obtained if the patient were lying on his or her back in the face up position.

By employing these estimated vectors, approximations of the other three vectors represented by the user interface of FIG. 6A may be derived. In particular, an estimated lying front posture vector may be obtained as a vector that is "opposite of" (that is, 180° away from) the estimated lying back vector. An estimated lying left vector is obtained as the cross-product of the estimated upright vector and the estimated lying front vector, with the direction of the estimated lying left vector being determined by the right-hand rule. An estimated lying right vector may be determined as a vector that is 180° away from the estimated lying left vector.

While the cross-product function and relationships such as "opposite of" may be used to derive estimated posture vectors, the disclosure is not so limited. Other relationships, such as an angular relationship, may be used to derive posture vectors, if desired. For instance, the estimated lying front posture vector may be derived as a vector that is co-planar with both the estimated upright and lying back vectors, having a first predetermined angle of less than 180° from the estimated lying back posture, and a second predetermined angle of less than 180° from the estimated upright vector. As a specific example, the lying front vector may be defined as being 70° from the estimated upright vector and 110° from the lying back vector, with all three vectors being co-planar.

As another example, an estimated lying right posture vector may be selected to be some predetermined angle that is less than 180° from the lying left posture vector, co-planar with the lying left and lying front posture vectors, and being closer to the lying front posture than the lying back posture. Many alternatives are possible within the scope of the current disclosure.

According to the above-described mechanism, estimated vectors may be determined for use in estimating a patient's Upright, Lying Front, Lying Back, Lying Left, and Lying Right, posture states. In this embodiment, each vector is automatically associated with the corresponding posture state definition by the system, and no intervention is needed to make these associations other than for the clinician to select the ORIENT feature once to capture the estimated upright vector when the patient is observed to be in relatively upright position. The derivation of all other vectors and association of vectors with the corresponding posture state may be performed entirely by a processor of programmer 20, entirely by processor 34 of IMD, or by some combination thereof.

While the Upright and the four Lying postures are discussed above as examples, other estimated posture vectors may be automatically derived for other posture states that a patient typically assumes. For instance, an estimated reclining posture vector may be derived that lies in a same plane as, and is halfway between, the estimated upright and lying back postures. Such a reclining posture vector may estimate the pose assumed by a patient when he is reclining in a lounge chair, for instance. An estimated leaning forward vector could be derived in a similar manner from the estimated upright and lying front vectors, for instance. Such a vector may describe the manner in which a bank teller may lean forward during daily tasks. Thus, more than the estimated posture vectors discussed above may be derived according to the current methods, and those discussed herein are examples only.

While the foregoing discusses capturing an estimated vector for the Upright posture state, the captured vector may be associated with a different posture state. As one example, a patient confined to a wheel chair may typically occupy a posture state wherein his torso is leaning backwards at a predetermined known angle. A clinician may, without participation on the part of the patient, capture a posture vector while the patient is in the wheelchair reclining at the known angle. During this process, the clinician may specify the angle of incline in relation to some other posture state of the patient (e.g., relative to what would be an Upright posture state for the patient, or relative to a posture state the patient would assume when lying on his back.)

The angle specified by the clinician may, in one scenario, be used to derive other estimated posture vectors for other posture states. For instance, an estimated upright vector may be calculated based on the specified angle between the reclining vector and the upright vector, based further on an approximated angle between a reference lying back vector and the upright vector (e.g., 90°), and further based on the fact that the estimated upright vector will reside in substantially a same plane as the reclining vector and the reference vector. These relationships may be used to derive a unique estimated upright vector for the Upright posture state. Once this estimated upright vector is derived, an estimated vector may be derived for the Lying Left posture state using a cross-product of the estimated upright vector and the reference vector, for instance. An estimated vector for the Lying Right posture state may also be derived as the opposite of the estimated lying left vector.

In a similar manner, the captured estimated vector may be one that is obtained while the patient is reclining backwards in bed at a known angle. The vector may be captured without the patient's participation using the ORIENT function of a programmer, as discussed above. A clinician may specify an angle of incline during this process such that techniques similar to those set forth above may be used to derive other estimated vectors from this captured vector. Thus, while an estimated upright vector may be the vector that is captured during an ORIENT procedure, this need not be the case, and a different vector may be captured instead.

Still other estimated vectors may be captured by the clinician during the calibration process, if desired. For instance, if a standard post-operative checkup procedure always requires that the patient assume a pose on his left side for some period of time (e.g., so that the clinician may listen to a heart beat while in this pose), it may be beneficial to capture an estimated posture vector for that patient while in this position, rather than in the upright position. In this alternative embodiment, the estimated upright posture vector could then be obtained via the cross-product of the estimated vectors for the Lying Left and Lying Front postures. Thus, a captured vector may be obtained to estimate the defined vector for virtually any desired pose, with that captured vector then being used to derive other vectors for other posture states.

In one embodiment, the system allows a user to customize a user interface during the calibration procedure to include representations of posture states the patient frequently occupies. In particular, one or more additional posture states such as a reclining posture state described above may be added to the set of posture states that is depicted by a user interface of a programmer. For instance, while an estimated vector is being captured, the clinician may manipulate an avatar provided by a programmer user interface to match the posture state frequently occupied by the patient (e.g., a reclining posture state). After the avatar has been positioned to approximate the desired posture state for the patient, a snapshot of the avatar may be acquired and associated with the vector captured for this posture state. This avatar representation may be added to a user interface display that represents posture states available within the system to control therapy delivery.

Figure 8B:
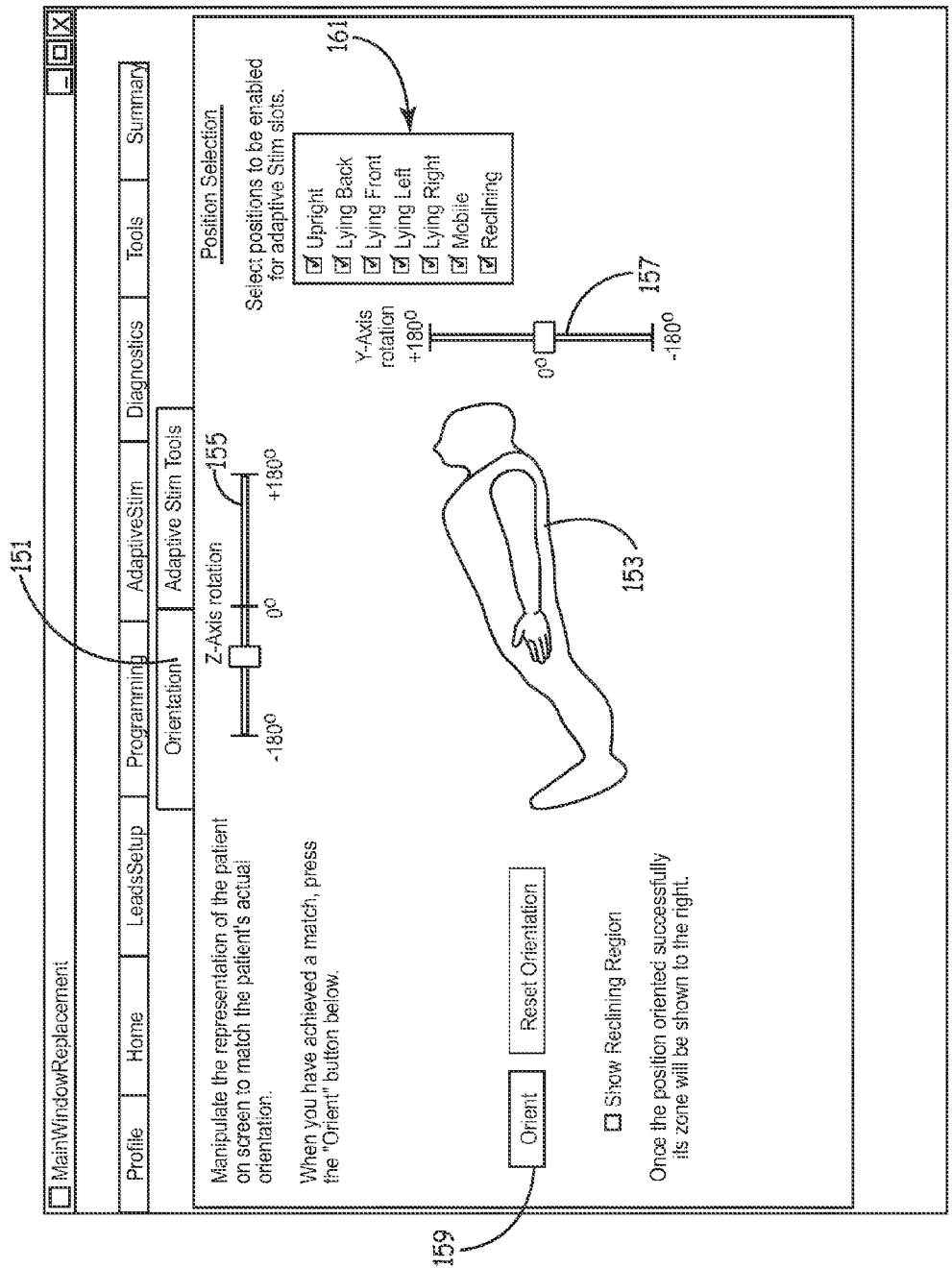
FIGS. 8B and 8C are screen shots illustrating positioning of an avatar during the capture of an estimated posture vector.
Figure 8C:
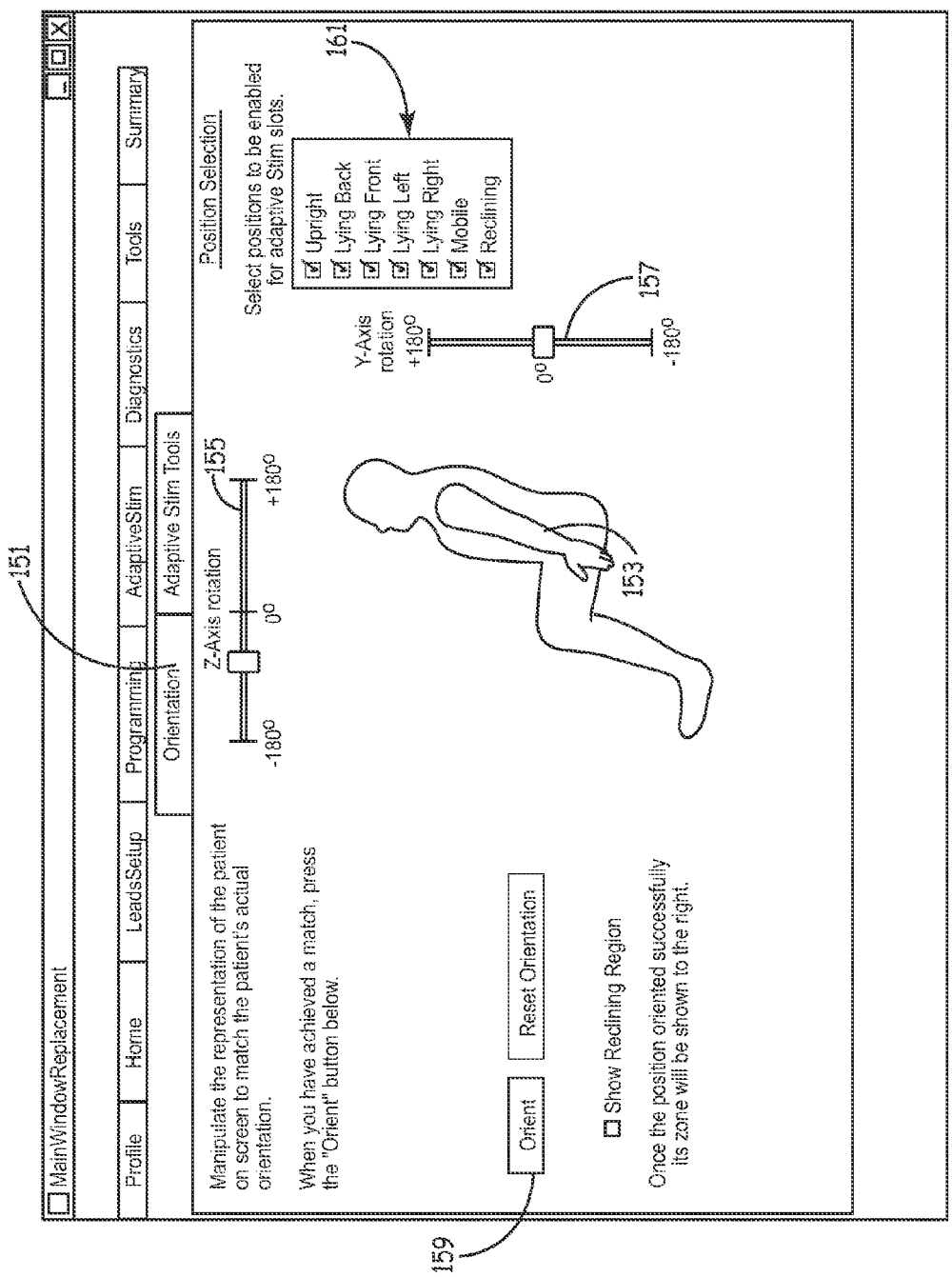

FIGS. 8B and 8C are screen shots illustrating positioning of an avatar during the posture state calibration process. Such screen shots may be provided by a user interface of clinician or patient programmer, for instance. A user may navigate to the screen by selecting an Orientation tab 151 in preparation to perform posture state orientation. The user may then manipulate a position of avatar 153 to match a desired posture state, which may be any position the patient occupies, and need not be limited to an Upright or Lying posture state. For instance, in FIG. 8B, the patient is assumed to be lying in a reclining position as when lying on an inclining bed or sitting in a reclining chair. In FIG. 8C, the patient is in a position that represents being seated in a wheel chair.

In the examples of FIGS. 8B and 8C, manipulation of the avatar may be accomplished using a cursor and drag-and-drop or other object manipulation functions known in the art. In one scenario, the programmer includes touch-screen capabilities that allow a clinician to re-position the avatar by moving a pointing device or a finger across the screen to "drag" or otherwise re-position portions of the avatar until the avatar represents the patient's actual posture state. In one example, re-positioning of the avatar may be accomplished using one or more slider bars. For instance, slider bar 155 is used to select the Z-axis rotation of the torso of the avatar, which may be selected to match the known angle at which the patient's torso is reclining, for instance. In FIGS. 8B and 8C, an angle of other than 0° has been selected for Z-axis rotation. Another slider bar 157 may be provided to select Y-axis rotation for the avatar, which will cause the avatar to be re-positioned in a manner that represents the patient rolling from side-to-side. In FIGS. 8B and 8C, slider bar 157 remains set to 0° to correspond to a patient reclining substantially lying flat on his back.

Once the avatar position matches that of the patient, the clinician may activate the ORIENT function 159. In one embodiment, this captures the estimated vector from sensor 40, and also associates the captured vector with the avatar position. The snapshot of the avatar captured at the time the ORIENT function 159 is activated may then be used to dynamically populate a display that includes frequently-used posture states for this patient. Such a display may be used to associate therapy parameters with the posture states in one example. If desired, the user may be queried to provide a name for the posture state, such as "Reclining". In this manner, a representation of almost any posture state frequented by the patient may be added to the set of posture state definitions for which a vector is estimated, and may further be represented on the user interface. A resulting list of posture states 161 is shown in FIGS. 8B and 8C.

The angles provided using slider bars 155 and 157 may be used to derive other estimated posture vectors as discussed herein. For instance, the Z-axis angle may be used in conjunction with the captured reclining posture vector and a reference vector to estimate an upright vector, which in turn may be used to estimate lying left and lying right vectors for the patient.

It will be understood that the user interface capabilities illustrated in FIGS. 8B and 8C need not be limited to use when capturing estimated vectors. Indeed, these techniques may be applied to obtaining a representation for any of the posture states in use within the system, including those associated with estimated vectors that are derived or associated with the reference vector. Moreover, this mechanism can be used in a system that does not utilize estimated vectors at all, but rather requires the patient to occupy each position to perform calibration. Additionally, while the techniques may be used to define a posture state that will dynamically update of list of postures represented by a user interface, this need not be the case. That is, these mechanisms may be used to generate a representation for a posture state that is one of a predetermined set of posture states allowed within the system. Thus, the way in which the techniques illustrated in FIGS. 8B and 8C may be implemented and used are many and varied.

While the foregoing assumes the use of a single captured vector such as an upright or reclining vector, the system is not so limited. For instance, the use of the reference vector could be eliminated in favor of using two captured vectors. Returning to the example of the foregoing paragraph, the clinician may capture an estimated vector while the patient is lying on his left side during an exam. A second estimated posture vector may be captured when the clinician observes that the patient's torso is substantially upright. Using these two estimated vectors and various relationships such as those discussed above, estimated posture vectors may be derived for the remaining posture states. In this alternative embodiment that captures two estimated posture vectors, there is no need to assume that a reference face of IMD 12 is in any particular orientation relative to patient 14.

According to another example embodiment, the clinician need not prompt the storing of any estimated posture vector (e.g., as by activating an ORIENT function). Instead, an activity level may be used to automatically trigger the capturing of an estimated posture vector that corresponds to an Upright posture state. For example, IMD 12 may monitor both AC and DC components of sensor 40 over time to determine which posture vector (as determined by DC components of sensor 40) is most prevalent when an activity level associated with walking (as indicated by the AC component) is detected. This posture vector may be used as the estimated upright posture vector, since it may be reasonably concluded that a patient approximates an upright pose when walking Once the estimated upright vector is determined, other estimated vectors may be derived in any of the aforementioned ways. This approach may require a longer time period for initialization of the posture-responsive therapy feature, since a monitoring period is required prior to determining the estimated posture vectors. However, this mechanism may be used to entirely automate the process of obtaining the estimated posture vectors, requiring no interaction whatsoever on the part of the clinician or patient.

Trigger events other than an activity level may be used to automate capturing of an estimated posture vector. For instance, if it is known that a patient is always upright or in a same lying posture at a particular time of day/night, a scheduling function may be used to prompt the capture of an estimated posture vector for the known pose at the corresponding time. That captured vector may then be used along with the reference vector to derive the various estimated posture vectors in a manner similar to that described above.

As yet another example of an automated trigger event, one or more sensors other than a posture state sensor may be provided to monitor physiological signals such as heart rate, EEG, ECG, oxygen levels within blood, respiration rate, and any other physiological signal. One or more such signals may be used as an automated trigger event. For instance, assume it is known that a patient always sleeps on her right side. One or more physiological signals such as heart rate, ventilation rate, and EEG signals may be used to detect when the patient is likely sleeping and trigger the capture of a vector for use with the Lying Right posture state definition. As another illustration, one or more such signals, such as a signal indicative of an elevated heart rate, may be used either alone, or in combination with the AC component of a posture state signal, to determine when a patient is engaged in physical activity. A vector associated with the DC signal component may be associated with the Upright posture state.

The foregoing describes obtaining estimated vectors for use in automatically generating posture state definitions. Next, the selection of tolerances for these automatically-generated definitions is considered. In one embodiment, each such posture state definition may be automatically associated with a tolerance by the system (e.g., a cone that surrounds the estimated posture vector.) Each such tolerance may be predetermined by the device manufacturer, for example. The tolerances may, but need not, be the same for each posture state definition. For instance, a cone of the same size may, but need not, be used as the tolerance for all definitions. In one scenario, the system may automatically associate a larger cone with the estimated upright vector than is associated with any of the estimated lying posture vectors, or vice versa. In one embodiment, each of the estimated lying vectors may be automatically associated with a same-sized cone so that each lying posture occupies the same size area in three-dimensional space. Alternatively, one or more of the lying posture states may be associated with larger cones. In still another embodiment, some posture states may be associated with areas that are of a shape other than a cone, such as a toroid. Any type and/or size of tolerance may be automatically associated with a given posture state definition.

In another embodiment that is more flexible and allows for more user interaction, a clinician may be provided with the opportunity to select a tolerance for each posture state definition that involves an estimated posture vector. As previously stated, each such tolerance describes a size and shape of the area disposed in relation to the associated vector.

As an example of the selection of tolerances by a user, the user interface may prompt a user to select whether cones surrounding the estimated posture vectors are to be "small", "medium", or "large". The angle associated with a selection (e.g., the angle associated with a "small" cone) may be determined by the device manufacturer, for instance. In one example, a user may be prompted once, and the user's selection is used to determine cone sizes for all posture state definitions. Alternatively, the user may be polled to enter a cone size for each posture state definition individually.

In a system allowing for even more flexibility, the clinician may be polled to select the desired angle to define one or more of the cone sizes, rather than being polled for a description (e.g., "small") that specifies the angle. Alternatively, a user may be allowed to provide a tolerance in some other manner, such as by providing an equation, or by using a touch screen to "draw" a spatial region relative to an estimated posture vector on a three-dimensional plot, for instance. Example mechanisms for providing tolerances are discussed above.

As may be appreciated, the mechanism used to support selection of the tolerances may be largely a matter of design choice. If simplicity and time-savings are most critical to the calibration procedure, predetermined tolerances chosen by the device manufacturer (e.g., based on historical data obtained during trials, etc.) may be used for initially creating the posture state definitions. In some case, updates to the tolerances may be made thereafter by the patient or clinician.

Once posture state definitions are automatically created in the aforementioned manner, therapy parameters may be associated with each posture state definition. This may be accomplished in one of several ways. A clinician may correlate therapy parameters with each posture state based on historical data obtained from the patient himself or data gathered from other patients having a similar indication and/or a similar prescribed therapy regimen as the current patient. Additionally or alternatively, parameters may be selected based on testing performed during the programming session or during a "trialing" period using an externally-worn device, or by some other means.

In one embodiment, one or more of the posture states need not be associated with therapy parameters during the initial programming session. In such a case, therapy associations may be created for the posture states as the patient goes about daily life. For instance, when the patient makes a therapy adjustment prior to, or while, assuming a particular pose, as by using a patient programmer to change one or more therapy parameters, the outputs from sensor 40 may be obtained and used to classify the patient's posture state based on the existing posture state definitions. If the patient is classified as being in one of the defined posture states (or in some embodiments, even it the patient is determined to be in an "unclassified" posture state), the therapy parameter set resulting from the patient's requested therapy modification is associated with the identified posture state. In this manner, associations between posture states and therapy parameters may be created for one or more posture states based on a patient's therapy modifications after the patient leaves the clinician's office.

In a manner similar to the foregoing, in one embodiment, each time a patient is in a posture state and makes a therapy adjustment, the therapy parameters associated with the posture state are updated to reflect the adjustment. This allows therapy delivery to change over time as the patient's condition, preferences, response to therapy, and/or other aspects of the therapy regimen evolve over time.

If desired, one or more posture states may be determined to be affiliated with one another such that a therapy adjustment that has already been associated with a first posture state is automatically associated with the affiliated posture state. As an example, the first time the patient makes a therapy adjustment while occupying any of the lying down postures, the resulting therapy parameters associated with the adjustment may be automatically associated with each of the lying down postures. This allows each of the posture states to be more quickly associated with therapy parameters than would otherwise occur if the patient were required to be in the posture state prior to the creation of such an association. Thereafter, the parameters that are specific to a given lying down posture state (e.g., Lying Back) may be updated to those selected by the patient as the patient actually assumes that specific posture state during daily life. Those skilled in the art will recognize that many permutations and possibilities exist to form associations between therapy parameters and posture states, and those mechanisms mentioned herein are merely exemplary.

FIG. 9 is an example table illustrating associations between posture states having estimated posture vectors and therapy parameter sets. Such a data structure may be stored as posture state definitions 52 (FIG. 3) within memory 36 of IMD 12. Alternatively or additionally, some of all of the definitions may be retained within memory of programmer 20 or within a storage device removably-coupled to programmer. Such definitions may be communicated periodically to IMD 12, as by telemetry downlink communication sessions. Column 160 lists illustrative posture states, including Upright, Lying Left, Lying Right, Lying Back, and Lying Front. More or fewer posture states (e.g., Reclining, Leaning Forward, etc.) may be defined in other embodiments.

As discussed above, a posture state is defined in terms of at least one of a posture and an activity component. The posture may be indicated by a posture vector and a tolerance, which are represented by columns 162 and 164, respectively, in the table of FIG. 9. The activity component is represented by activity parameters listed in column 165. For purposes of this discussion, each of the posture state definitions is assumed to include a posture defined by a vector. However, it will be appreciated that the definitions may also include an activity component, which may be an activity count obtained from an AC component of the output of sensor 40, for example. For instance, the Upright posture state may include an activity component A1 that is used to identify when the patient is Upright but inactive. Another posture state (not shown in the table of FIG. 9) that may be referred to as Upright and Active may include a different activity component to identify when the patient is both standing upright and is engaging in a higher level of activity, and so on. Moreover, some posture states may be described in terms of an activity component without reference to a vector, although such posture states are not the focus of the current discussion. As yet another example, the activity component may be associated with a vector indicating direction of acceleration, direction of velocity, and so on.

As previously discussed, each defined posture state that is associated with a posture may include not only a vector, but a tolerance. A tolerance will define some region in three-dimensional space that is disposed in relation to the vector. Such a tolerance is shown recorded in column 164 of the table of FIG. 9 as "Cone 1" for the Upright posture state, although this is an example only, and other types of tolerances may be selected for use with a posture state definition.

In the current example, it will be assumed that the posture vectors of columns 162 are initially obtained by estimation in the aforementioned manner. That is, these vectors are not measured while the patient consciously assumes a corresponding posture, since this may require too much time and effort on the part of both the patient and an attending clinician. While one or more vectors may be measured while the patient assumes the posture state for another reason, no additional patient effort is required to perform the vector calibration process.

Many methods are available for obtaining these estimated vectors, examples of which are illustrated by column 163. For instance, an estimated posture vector may be assigned the same vector as a reference vector, as is illustrated for the Lying Back posture state. Alternatively, an estimated posture vector may be captured when the patient is in a position that approximates the corresponding posture state (e.g., as by storing the outputs of sensor 40.) In another example, an estimated posture vector may be obtained as a function (e.g., a cross-product) of one or more of the other estimated posture vectors. In yet another example, a vector may have an angular relationship to one or more other estimated posture vectors (e.g., 180° from another predetermined estimated posture vector.) This is as shown for the Lying Right and Lying Front posture states, for instance. Many other such relationships exist, as will be described below.

Each defined posture state may be associated with therapy parameters, as indicated by column 166. As previously discussed, such parameters may include those associated with electrical stimulation therapy such as current or voltage amplitude, pulse width, electrode combination(s), electrode polarities, stimulation duty cycle, stimulation waveform shape, identification of one or more programs, and so on. Such parameters may additionally or alternatively include those associated with drug delivery, such as a substance identification, a bolus amount, an increment of time associated with bolus delivery, and so on. A parameter associated with any other type of therapy may be associated with a posture state in the alternative. Each posture state may be associated with additional actions (e.g., initiation of notifications, storing of data, etc.) which are largely beyond the scope of this disclosure.

Figure 10:
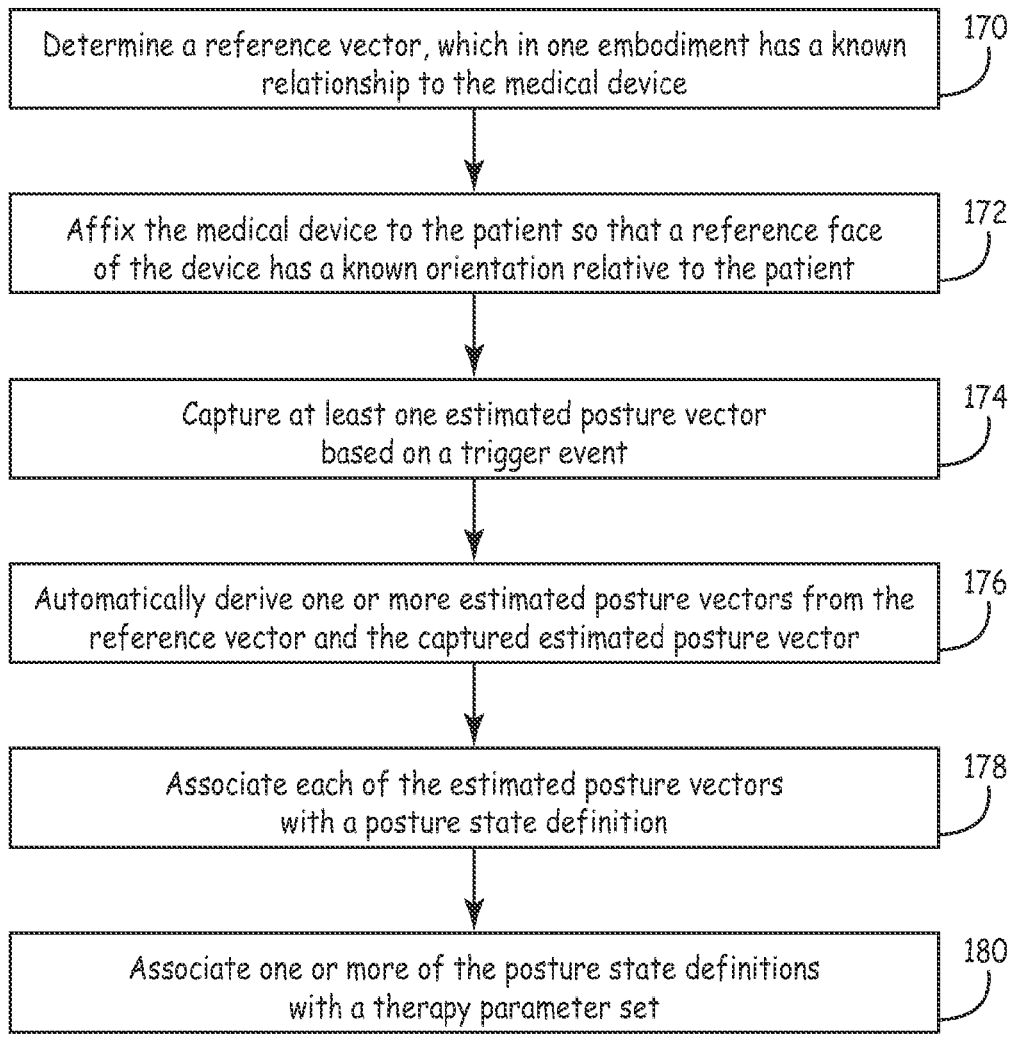
FIG. 10 is a flow diagram of an initialization method according to the current disclosure.

FIG. 10 is a flow diagram of an initialization method according to one embodiment of the current disclosure. According to this example, a processor obtains a reference vector having a predetermined relationship to a housing of the medical device. The processor then automatically estimates from the reference vector a parameter value for at least one of the posture state definitions. As described herein the parameter value is a vector. However, the parameter value could, in another embodiment, be some other indication of direction that is used to create a posture state definition.

The flow diagram commences by determining a reference vector (170). In one embodiment, this reference vector has a known relationship to the medical device (e.g., a known relationship to the housing of the device). For instance, it may be a vector obtained when the medical device is placed with a reference side up (e.g., "face up") on a level surface. Other reference vectors may be used in the alternative, such as a reference vector associated with a particular edge of the device.

Next, the medical device is affixed to a patient so that a reference face of the device has a known orientation relative to the patient (172). This may be performed during an implant procedure. In the case of an externally-worn device, this may involve otherwise affixing the device to the patient. In one embodiment, the reference face is a predominant surface of the device that will be substantially parallel with, and closest to, a cutaneous boundary of the patient's torso. In a different embodiment, a reference face may be some other surface or portion of the device that will have a known relationship (perpendicular with, parallel to, etc.) to a vector used to approximate a posture state vector for a patient.

At least one estimated posture vector may next be captured, as by obtaining outputs of sensor 40 (174). This capturing of sensor signals may be prompted based on a trigger event. According to one embodiment, the captured estimated posture vector is a vector captured when an "ORIENT" feature of a programmer is activated. For instance, a clinician may selectively activate such a feature when he or she observes that a patient's torso is in a posture state that substantially approximates the position it would be in if the patient were standing upright. Such an approximation may be obtained when the patient is sitting erect in a chair, or is standing. Alternatively, the clinician may activate the feature while the patient occupies a typical pose, such as reclining backwards slightly in a wheelchair or lying backwards in an elevated bed. The capturing of the vector may be performed by a clinician in a manner that is entirely transparent to the patient. Alternatively, if desired, the vector may be captured after the patient is given some instruction (e.g., "please sit up straight").

In a different embodiment, the trigger event may involve detecting a signal from sensor 40 that indicates the patient is engaged in a predetermined activity level. In particular, a predetermined number of samples from sensor 40 may be acquired that have an AC component that indicates a predetermined level of activity, such as an activity level that may be associated with the patient being upright and walking Once such samples are detected using the AC signal component, the DC signal component of these samples may be used to derive a position vector that estimates an upright vector. In one case, this estimated vector may be a mean, median, or some other value derived from the multiple samples.

In another embodiment, the trigger event may be based on a schedule, such as a time of day when it is known the patient will be in a particular posture state. Use of other trigger events is possible, and the foregoing are only examples. Thus, the degree of patient and clinician involvement in this step may vary based on patient and clinician practices, preferences, the amount of time considered acceptable for obtaining the estimated vectors, and so on. In some cases, neither the patient nor the physician need have any involvement in the process.

After one or more estimated posture vectors are captured in the foregoing manner, one or more additional estimated posture vectors may be derived from the reference vector and the captured estimated posture vector (176). In one embodiment, an estimated lying back posture vector may be associated with the reference vector, and the estimated upright vector may be identified with the captured vector. An estimated lying left vector may be obtained from a cross-product of the estimated upright and lying back posture vectors, and the estimated lying front and lying right posture vectors may be determined using angular relationships with the estimated lying back and lying left posture vectors, respectively. Such derivation may occur entirely automatically and without aid of the clinician or patient.

Once the estimated posture vectors are so determined, each such vector may be associated with a posture state definition (178). This step may further include associating a tolerance with a posture state definition. As discussed above, the tolerance describes a relationship with a respective estimated posture vector, and thereby defines a geographic region that is defined relative to the vector (e.g., a cone surrounding the vector.) In one embodiment, a predetermined tolerance may be automatically associated with each of the posture state definitions so that the clinician need not be involved in making this association. Thus, the association of an estimated posture vector and a tolerance with a corresponding posture state definition may occur entirely automatically, and without aid of a clinician or patient in one embodiment.

Each posture state definition may be associated with a therapy parameter set (180). This is as shown in FIG. 9. Such an association may be made by a physician in any of the ways discussed above. Alternatively, creation of an association with a given posture state may be deferred until the patient makes a therapy adjustment when occupying the posture state, at which time the updated therapy parameter set resulting from the adjustment may be associated with the posture state. Thereafter, if desired, the associated therapy parameter set for the posture state may be updated based on future therapy modifications made when the patient is in that posture state. If desired, one or more actions may be associated with each posture state in addition to, or instead of, a therapy parameter set. Such actions may include the initiation of a notification, storing of data, initiation of a communication session, or any other action associated with the system.

Many alternative embodiments of the method of FIG. 10 are possible within the scope of the disclosure. As previously-discussed, steps 170 and 172 of FIG. 10, which involve determination of a reference vector, may be eliminated in one embodiment. In such an embodiment, step 174 may involve the capture of more than one estimated posture vector. For instance, a clinician may prompt the capture of an estimated upright posture vector and an estimated lying back posture vector when the patient assumes such poses for other reasons during an examination and/or programming session. In one embodiment, the capture of such estimated posture vectors may be entirely automated, as may be accomplished using trigger events such as times of day, days of the week, activity levels, or signals from other sensors (e.g., a heart rate sensor to detect sleep, etc.). The multiple captured vectors may then be employed to derive other estimated posture vectors in step 176. In some cases, steps may be performed in a different order, and some steps may be eliminated entirely. Thus, it will be understood that the techniques exemplified in FIG. 10 lend themselves to many variations and combinations, and the illustrative method is not to be considered limiting.

As may be appreciated from the foregoing, when the posture state definitions are first created according to methods described herein, the posture state definitions are estimations only. In other words, the vectors associated with those definitions are not necessarily accurate representations of posture states that the patient will assume as he or she goes about daily life since, in general, the estimated vectors are derivations and/or approximations rather than measurements obtained as the patient occupies a particular posture state during daily life. Moreover, even postures that are captured based on poses assumed in a clinic setting may not accurately represent those postures a patient will actually assume when in the comfort of his or her home (as when sleeping with one's own pillow.)

According to one aspect of the disclosure, the estimated posture vectors are periodically updated so that they become a closer representation of postures that the patient actually occupies during daily life. One method for triggering such updates involves detecting when a patient makes a therapy modification, as may be accomplished by the patient using a programmer 20 to change an aspect of delivered therapy (e.g., a stimulation amplitude) or another type of therapy such as drug delivery. When such a therapy modification is requested by the patient, the output of sensor 40 may be captured and used to classify the patient's posture state. That is, the vector that is obtained from the sensor output, and which represents a currently-detected posture of the patient, is compared to the existing posture state definitions. Based on this comparison, it is determined whether the detected posture vector indicates the patient resides within one of the posture states as defined by the originally-generated estimations. This could be accomplished in one embodiment by determining whether the currently-detected posture vector lies within a cone associated with any of the posture state definitions. Described more generally, this involves determining whether the detected posture vector lies within the geographic region oriented relative to an associated estimated posture vector as specified by the tolerance.

In one embodiment, if the detected posture vector lies within a geographic region in three-dimensional space that has been associated with a posture state, the detected posture vector is used to update, or revise, the estimated posture vector for that posture state. This may be accomplished by "blending" the detected posture vector $V_{pt}$ that describes the patient's current posture with the defined posture vector $V_{def}$ obtained from the posture state definition. The revised vector $V_{rev}$ is then used as the new defined posture vector. The blending may utilize a weighting factor $\alpha$ as follows:

$$V_{rev} = (1-\alpha)V_{pt} + \alpha V_{def} \qquad \text{(Equation 1)}$$

As an example, if $\alpha$ is selected to be 0.5, the defined posture vector obtained from the definition (which may initially be an estimated value) and the detected posture vector from sensor 40 that represents the patient's current posture are averaged to obtain the newly-revised posture vector, $V_{rev}$. In other words, an average is taken for each of the x, y, and z components to obtain the new vector. If $\alpha$ is instead selected to be something less than 0.5, the detected posture vector $V_{pt}$ is accorded more weight than the defined posture vector $V_{def}$. Conversely, if $\alpha$ is something greater than 0.5, the detected posture vector is accorded less weight than the defined posture vector. In this manner, the selection of the value for $\alpha$ will determine how fast an estimated posture vector is modified. The value for the weighting factor $\alpha$ may be programmable, and may be selected by a user such as a clinician. Alternatively, this value may be predetermined by the device manufacturer such that it cannot be changed.

The value of $\alpha$ may be selected to be specific to a particular posture state. For instance, it may be known that the estimated posture vector for the Upright posture state is generally relatively accurate, while the estimated posture vectors for the lying posture states are not as accurate. Thus, the values for $\alpha$ may be selected to be smaller for the lying posture states to allow those posture states to be updated more quickly following the vector calibration procedure. In contrast, it may be advantageous to use a larger $\alpha$ value for the estimated Upright posture vector, thereby introducing more stability into the system for this vector, and preventing large changes based on any one detected vector for this posture state.

Other factors may influence the selection of $\alpha$ instead of, or in addition to, the posture state. For instance, $\alpha$ may be increased or decreased based on a scheduling function (e.g., during a particular time of day and/or day of the week when it is known that the patient typically occupies a posture state). As an example, assume that a posture state of Leaning Forward has been defined for a bank teller. The teller occupies this posture state on a regular basis between the hours of 9 am-12 pm, and 1 pm-5 pm on weekdays. Therefore, during these times/days, the value for $\alpha$ may be automatically decreased to accord more weight to detected posture vectors classified as falling within this posture state. This will allow adaption of the Leaning Forward posture state to occur more quickly during these times. Conversely, the value for $\alpha$ may be increased for this posture state during other times, since any detected vectors occurring at other times may be less likely to truly represent the Leaning Forward posture that the patient has defined for use at work, and may instead represent some other posture state or posture-related transition (e.g., a transition to a Face Down posture, for example.)

As another example, $\alpha$ may be modified for one or more of the posture state definitions based on a measured patient parameter indicative of the patient's state. Such parameters may include, but are not limited to, a patient's heart rate, blood pressure, a blood chemistry value such as glucose level, an activity level (as may be determined by an AC component of the signal of sensor 40), or any other parameter that may be measured by a sensor operatively-or communicatively-coupled to IMD 12 and/or programmer 20. For instance, it may be advantageous to modify $\alpha$ for one or more posture states when it is determined the patient is likely engaged in exercise, when the patient is thought to be sleeping, when the patient is not sleeping but is relatively still, and so on.

Returning to the discussion of Equation 1, after derivation of the revised vector $V_{rev}$, this revised vector value may be used to replace the previously-defined posture vector. For example, in an embodiment that utilizes a data structure such as that shown in FIG. 9, the revised vector may be stored within column 162 of the table within the entry associated with the corresponding posture state, thereby overwriting the previous posture vector, which may be the estimated posture vector. This new vector is thereby available to determine whether the patient occupies that posture state in the future.

In another embodiment, the current revision of the posture vector $V_{rev}$ may be retained along with some predetermined number of previous revisions of this posture vector. This revision history may be retained within a data structure such as that shown in FIG. 9, or may instead be retained as some other type of history data (e.g., posture state history file 54 of FIG. 3, for example.) The revision history may be stored within memory 36 of IMD, within a memory of programmer 20, and/or in some other storage device associated with the system. This history data may be used by clinicians or other device professionals to analyze how a particular vector underwent adaption so that the method of performing the adaption may be improved, for example. For instance, this type of analysis may be used to re-select values for $\alpha$. This data may also be analyzed to determine patient well-being, such as patient response to therapy or progression of a disease state.

In the embodiments described above, if a patient is classified as being in a posture state based on the currently-detected posture vector $V_{pt}$, $V_{pt}$ is considered to be eligible to update the corresponding posture state definition. In other embodiments, some other filter criterion is used to determine when the detected posture vector $V_{pt}$ is eligible to update a posture state definition. This filter criterion may be more restrictive than the posture definition itself.

As an example of the above-described alternative embodiment, after a patient has been classified as being in a particular posture state, a filter for that posture state may be retrieved. This filter may require the detected posture vector $V_{pt}$ to be no more than a predetermined distance from the defined posture vector $V_{def}$. This distance may be described in terms of an angle, a Euclidean distance, a straight-line distance, a city-block distance, a Minkowski distance, a trigonometric function, or some other measure of the separation between $V_{pt}$ and $V_{def}$. Only if $V_{pt}$ lies within the required distance of $V_{def}$ will $V_{pt}$ be used to update the defined posture vector. As an example, the filter may specify a cone that resides inside a larger cone that describes the spatial region for the posture state definition. If $V_{pt}$ lies within this smaller inner cone, $V_{pt}$ will be used to update $V_{def}$. Otherwise, the update will not be made, and the currently-defined posture vector $V_{def}$ remains unchanged for this posture state definition, even though $V_{pt}$ lies within the geographic region associated with the posture state. Thus, a filter may be used to further restrict how much a defined posture vector can change at any given time, since the filter may require a detected vector that is "close to" the defined posture vector before an update will be allowed.

In another embodiment, the filter may be described as some percentage of the tolerance for a given posture state definition. For instance, assume a posture state definition includes a tolerance described in terms of a cone surrounding the defined posture vector. The apex of the cone has an angle of 40°. A 25% filter may be used with this definition, thereby describing a cone surrounding the defined posture vector having an apex with an angle of 10°. Only if the detected posture vector is within this smaller inner cone will it be used to update the posture state definition.

In another embodiment, a filter may specify that a detected posture vector is to be ignored (that is, not employed to update the defined posture vector) if it is within some predetermined "edge" of a spatial region that defines the tolerance. As an example, the filter may indicate that if the detected posture vector $V_{pt}$ is within a predetermined distance of an outer edge of the cone surrounding $V_{def}$, the vector will not be employed to calculate $V_{rev}$, but rather will be discarded. As discussed above, this distance may be expressed as an angle, a percentage of the apex of a posture cone, a Euclidean distance, a straight-line distance, a city-block distance, a Minkowski distance, using a trigonometric function, or using any other mechanism that may be employed to specify the separation between an outer edge of the spatial region and $V_{pt}$.

While a filter describing a region in three-dimensional space will generally be defined to be co-extensive with, or a sub-set of, the tolerance for a posture state, this need not be the case. That is, the filter could describe one or more regions in space not associated with the posture state. As a simple example, the filter could describe a cone that is larger than a cone representing the posture state definition. Such an embodiment allows detected posture vectors that are not classified as being within a posture state definition to change the vector for that posture state definition. For instance, a detected posture vector that is outside of the region associated with the posture state definition, but still within some maximum distance of that region, may never-the-less be used to update a defined vector for the posture state definition. Such an embodiment may allow relatively large changes to be made to a defined posture vector in one processing step, which may be undesirable. In such embodiments, it is generally desirable to define the filters of the various posture state definitions so that no ambiguity exists about which posture state definitions a detected posture vector may modify. For instance, it is generally desirable to avoid a scenario wherein a given detected posture vector could potentially be used to update more than one defined posture vector.

In yet another embodiment, the filter may define a time period during which the patient must remain classified in a given posture state after a therapy parameter modification was requested before the vector is updated. This will ensure that a patient's posture state classification is stable before the defined posture vector is updated. For instance, assume a patient requests a change in therapy that prompts classification of the patient in a particular posture state. Following such a request, the system may require that the patient remains classified in this same posture state for a time duration T before the detected posture vector will be used to update the defined posture vector. If the patient's posture state does not remain classified within the posture state during the requisite time duration, a change to the defined posture vector is not made. The time period T, which may be referred to as a stability window, may be used in this embodiment to prevent posture states that are only temporarily assumed from resulting in a change made to a defined posture vector.

In an embodiment wherein a stability window is employed, the detected posture vector $V_{pt}$ that may potentially be used to update $V_{def}$ may be determined in any number of ways. $V_{pt}$ may be determined as the first vector that resulted in the patient's classification in the given posture state at the start of the stability window T. Alternatively, it may be a vector that is sampled sometime during the stability window T (e.g., midway through time T). It may instead be the vector that is obtained at the end of stability window T. In still another example, it may be an average, median, or some other vector obtained from the multiple samples of the patient's detected posture vector obtained during time T. For instance, samples may be taken at regular time intervals during the stability window T to obtain an average that is employed as $V_{pt}$. This vector $V_{pt}$ is then used to update $V_{def}$ if the patient remains classified in the posture state.

As was the case when selecting a value for α, the time duration T employed for a stability window may be specific to a posture state. For instance, a longer time duration T may be required for some posture states that are know to take the patient a long "settling time" to assume. Other posture states that may be assumed relatively easily may instead be associated with a smaller stability window. Moreover, the stability window may be modified for one or more of the posture state definitions based on a time of day, day of week, or based on some other measured physiological parameter, including but not limited to the parameters described above. For instance, it may be advantageous to modify time T for one or more postures when it is determined the patient is likely exercising, or when the patient is thought to be sleeping, as determined based on heart rate, activity level, and so on.

If desired, a filter for one or more of the posture state definitions may be described in terms of both a spatial region (e.g., $V_{pt}$ is within a specified distance from $V_{def}$) and in terms of a stability window. For instance, the filter may require that the patient remain classified within the posture state for the duration of the selected stability window T, and further that $V_{pt}$ be no more than some predetermined distance (however calculated) from $V_{def}$. In such a scenario, if one or more of the filter requirements are not met, $V_{pt}$ is not used to update $V_{def}$.

Thus, many factors may be employed to determine when, and how quickly, a particular posture state definition is updated based on a detected posture vector. A same set of considerations may be selected for all posture state definitions, or one or more of the posture state definitions may be associated with a respectively-different set of considerations.

Figure 11A:
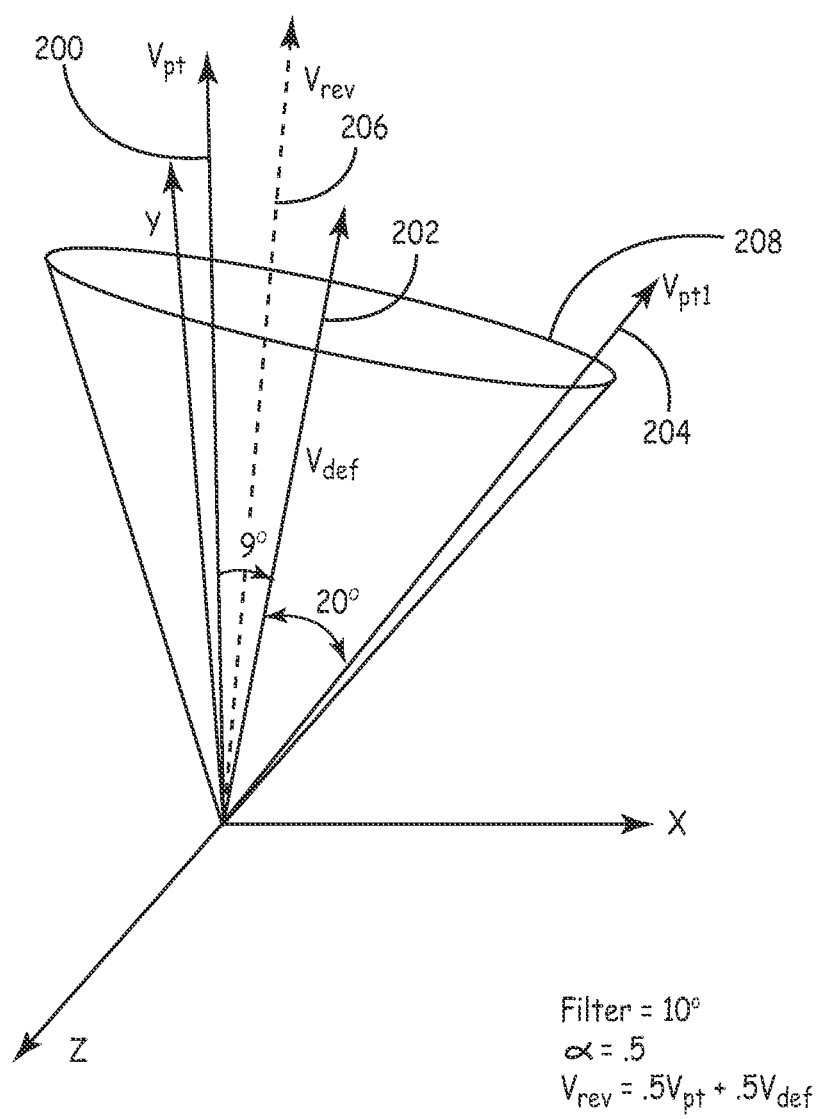
FIGS. 11A-11B illustrate the use of a detected posture vector and a filter to update an existing defined posture vector.

FIG. 11A illustrates use of a detected posture vector $V_{pt}$ 200 along with a spatial filter to update an existing defined posture vector, $V_{def}$ 202. In this example, $V_{def}$ 202 may correspond to an estimated posture vector for the patient's Upright posture state, as captured either automatically or with user intervention following a procedure that affixed the medical device to a patient (e.g., an implantation procedure.)

In this example, a filter is being used to determine whether $V_{pt}$ 200 will be employed to update $V_{def}$ 202. The filter of this example requires that $V_{pt}$ and $V_{def}$ be separated by no more than 10° for the update to occur. Since in this case, $V_{pt}$ 200 is only 9° from $V_{def}$ and therefore meets the requirements of the filter, $V_{pt}$ 200 will be used to update $V_{def}$ 202. Note that if $V_{pt}$ were instead at the location shown for vector $V_{pt1}$ 204, this would not be the case, since $V_{pt1}$ is 20° from $V_{def}$, and is outside of the requirements specified by the filter.

Since $V_{pt}$ 200 is within the requirements of the 10° filter, this detected vector is used to derive a revised vector $V_{rev}$. It will be assumed that a method according to Equation 1 above is used for this purpose, and that the weighting factor α is selected as 0.5. Therefore, the revised vector $V_{rev}$ will be calculated to lie in a same plane as both $V_{pt}$ and $V_{def}$, and will bisect that angle between $V_{pt}$ and $V_{def}$. This revised vector is shown in FIG. 11A as $V_{rev}$ 206 (shown dashed).

Once the revised vector is determined, the spatial region associated with this posture state, as was described by cone 208 that surrounded $V_{def}$ 202, shifts. That is, cone 208 will now surround $V_{rev}$, which will define the new spatial region that is used to classify the patient in this posture state.

The foregoing example illustrates use of a spatial filter to derive a new vector. As was previously discussed, use of a filter may be eliminated, and $V_{pt}$ may be used to update $V_{def}$ whenever the patient occupies the corresponding posture state. That is, so long as $V_{pt}$ lies within the spatial region associated with a given posture state, which in the current example is cone 208, $V_{pt}$ will be used to update the defined posture vector for this posture state. In such an embodiment, the tolerance itself, as defined by the posture state definition, may be considered the filter. In such an embodiment, detection of either $V_{pt}$ 200 or $V_{pt1}$ 204 via sensor 40 would prompt updating of $V_{def}$ 202, since both $V_{pt}$ 200 and $V_{pt1}$ 204 are within cone 208 associated with the posture state definition.

Figure 11B:
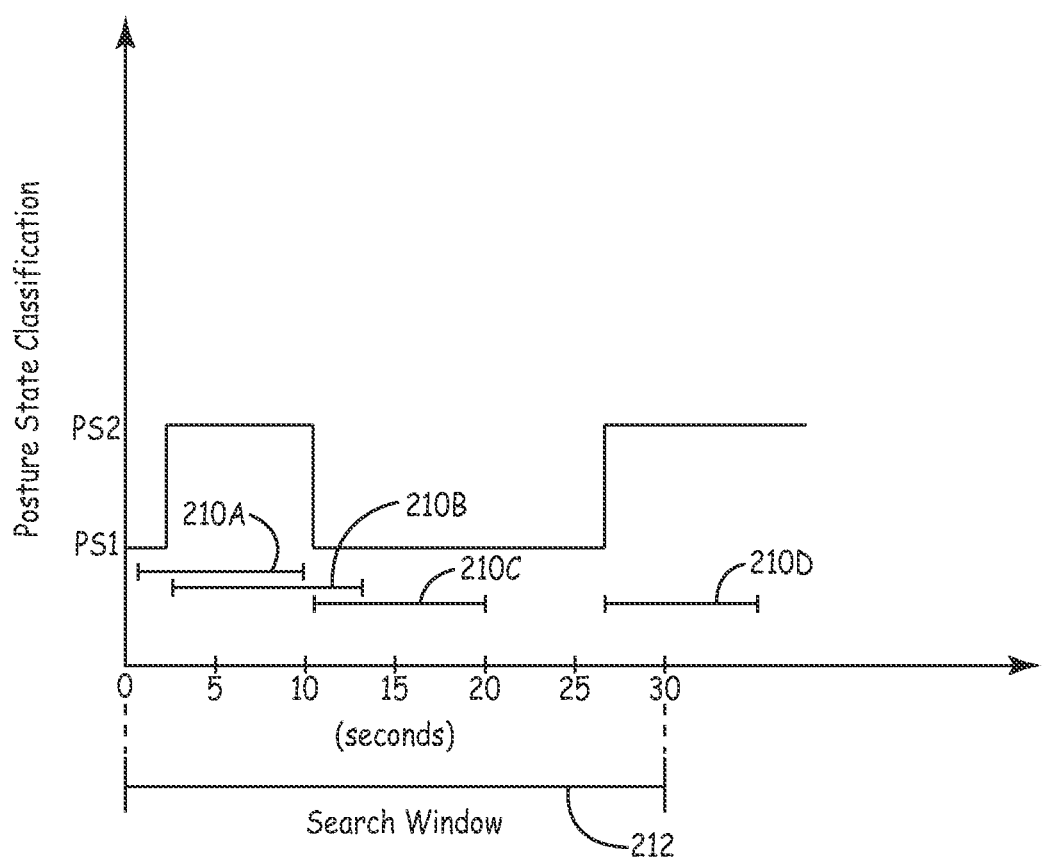

FIG. 11B is a conceptual diagram illustrating use of a time filter to control whether to use a detected posture vector $V_{pt}$ to update a defined posture vector. In this diagram, time (in seconds) is depicted on the x axis, while the posture state in which the patient is classified is described by the y axis. The filter will be described in terms of both a stability window as represented by lines 210A-210C, and by a search window as illustrated by line 212. In this case, the stability window has a duration of 10 seconds, while the search window has a duration of 30 seconds.

According to this embodiment, search window 212 starts when the patient makes a request to modify therapy, which serves as the trigger event. This request causes the patient's posture state to be classified. Upon such classification, a stability timer is started, as indicated by lines 210A. This stability timer will be used to determine whether the patient's posture state remains stable for the requisite time period, which is selected to be 10 seconds in this example. If the patient remains within the initially-classified posture state for the duration of the stability window represented by line 210A, the filter requirements are met, and one or more detected vectors measured during this stability window will be used to update the posture state definition.

In the instant example, the patient's posture state is not stable throughout the initial stability window, but instead changes after about 3 seconds such that the patient's posture state is re-classified to the new posture state PS2, as represented by the y axis. As a result of this re-classification of the patient's posture state, the stability timer is re-started, as represented by line 210B. Once again, the patient's posture state does not remain classified in posture state PS2 for a complete 10 seconds, but instead reverts back to posture state PS1 before expiration of the stability window represented by line 210B. This once again causes the stability timer to be restarted, as indicated by line 210C. This time, the stability timer expires at roughly a time of 20 seconds and while the patient remains in posture state PS1. Therefore, one or more samples of the patient's detected posture vector obtained during the time period coinciding with line 210C will be used to update the defined posture vector. This may include a first posture vector detected at roughly a time of 10 second, the posture vector detected midway through the time-period represented by line 210C (occurring at about 15 seconds), or the posture vector detected at the end of the stability window (occurring at about 20 seconds). The detected posture vector that is used to update the defined posture vector may instead be derived as some median, average, or other vector calculated using any other function based on any number of samples acquired during the time period represented by line 210C. For instance, samples may be obtained every second during this time period, averaged, and used as $V_{pt}$ to update the defined posture vector.

For further illustration, assume that the patient continued to move throughout the search window 212 so that a stable posture vector is not obtained (that is, there was no ten-second period of time wherein the patient remained classified in the same posture state). Further assume that the patient's posture state is re-classified at a time of 27 seconds such that the stability timer is restarted in a manner indicated by line 210D. While the stability timer is still running, the search window 212 expires at a time of 30 seconds. According to one embodiment, if the patient remains stable in that final posture state throughout expiration of this final stability window 210D, one or more posture state vectors will be used to update the defined posture vector. If the patient's posture state does not remain stable, however, the stability timer will not be restarted when the patient assumes yet another posture state, since that posture state will be assumed after expiration of search window 212. In this latter case, no updating of the defined posture vector will occur.

In another embodiment not shown in FIG. 11B, expiration of the search window may be used to terminate all on-going stability windows and prevent any vector updates from occurring outside of the search window. In other words, according to the alternative embodiment, if a stability window does not expire within the search window, no vector updates will occur.

The length of a stability window, as well as that of the search window, may be programmably selected. In one embodiment, the search window may be between 2 and 10 minutes and a stability window may be between 1 and 5 minutes. In one specific embodiment, the search window may be selected as being 7 minutes long while the stability window is 2 minutes long. In another embodiment wherein the search and stability window are a same length, both windows are set to 3 minutes.

The durations of the search window and stability window may be selected to be specific to a given posture state. That is, a stability window and/or search window may be used for the Upright posture state that is different than one or more time periods used for a Reclining posture state, or one of the Lying posture states. Moreover, such time periods may be specific to a time of day, a day of week, or even based on a parameter indicative of the patient state (e.g., blood pressure, heart rate, activity level, blood oxygen level, and so on.) In this manner, one or more factors may be used to select a filter that is based on at least one of a spatial relationship to a defined posture vector or a time relationship associated with an event such as a trigger event.

The foregoing describes how one or more samples of a patient's posture vector $V_{pt}$ may be used to update a defined posture vector $V_{def}$. In one embodiment, the output of sensor 40 may be sampled multiple times to obtain $V_{pt}$, as was described above with respect to use of stability window. Use of multiple samples in this manner may likewise be employed in embodiments that do not use time filters (e.g., stability windows and/or search windows). Use of multiple samples to derive $V_{pt}$ may be useful if the patient is in the habit of making a therapy adjustment before he or she is completely settled in a particular pose. In such embodiments, many variations are possible to determine which samples will be used to derive $V_{pt}$. For instance, one embodiment may use only those samples that are classified as being in a posture state to update the vector for that posture state. That is, if one or more of the samples obtained during a sampling period are outside of the spatial region associated with the posture state, those samples are discarded, and are not used to determine $V_{pt}$ to update that posture state.

Many processing techniques may be employed to derive $V_{pt}$ from multiple samples, including averaging, use of a most-frequently-occurring or median vector value, minimum or maximum values, and so on. One such technique uses a histogram approach to classify multiple samples to obtain $V_{pt}$. According to this method, each sample (referred to as $V_{pts}$) is first normalized. To normalize a sample, each of the x, y, and z components of this vector (shown as $V_{pts1}$, $V_{pts2}$, and $V_{pts3}$ below) are divided by the length $\|V_{pts}\|$ of the vector, as follows:

$$\text{Norm}(V_{pts}) = \frac{\lfloor V_{pts1}, V_{pts2}, V_{pts3} \rfloor}{\|V_{pts}\|} \quad \text{(Equation 2)}$$

$$\text{where } \|V_{pts}\| = \sqrt{V_{pts}^2 + V_{pts}^2 + V_{pts}^2}$$

Figure 12A:
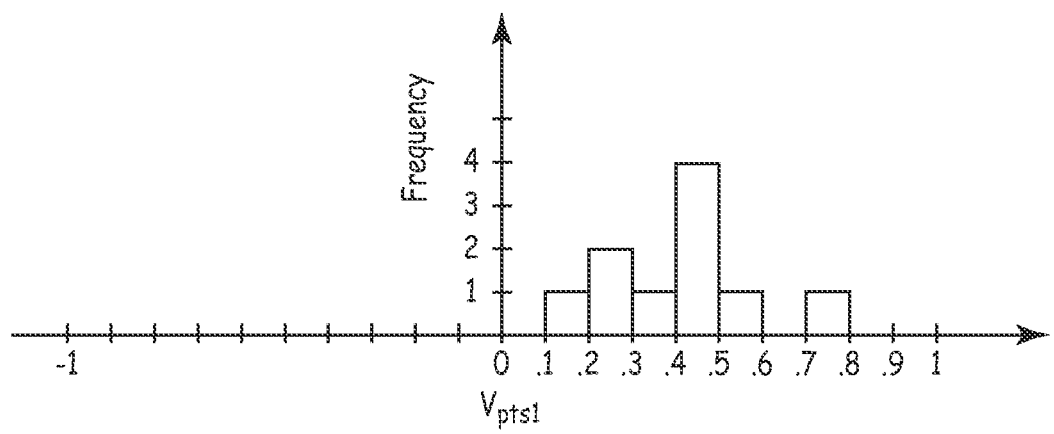
FIGS. 12A-12C depict use of histograms to derive a detected posture vector from multiple vector samples.
Figure 12B:
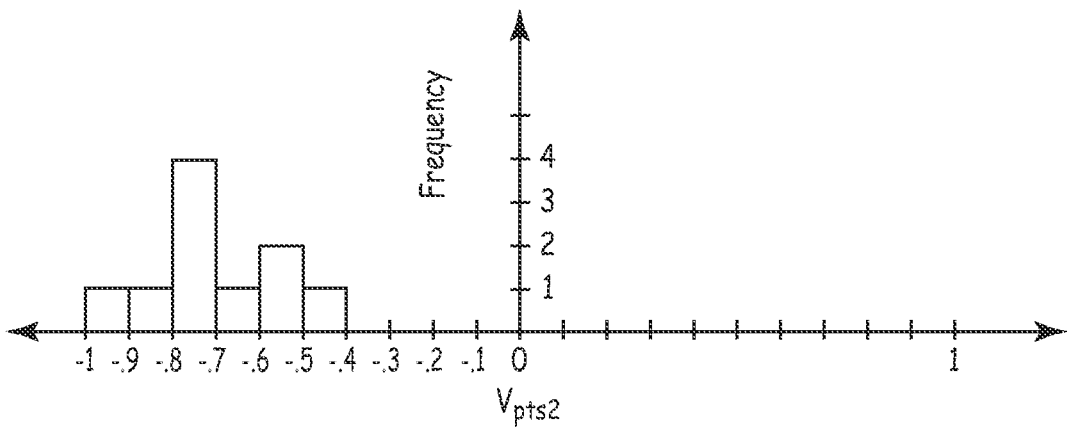
Figure 12C:
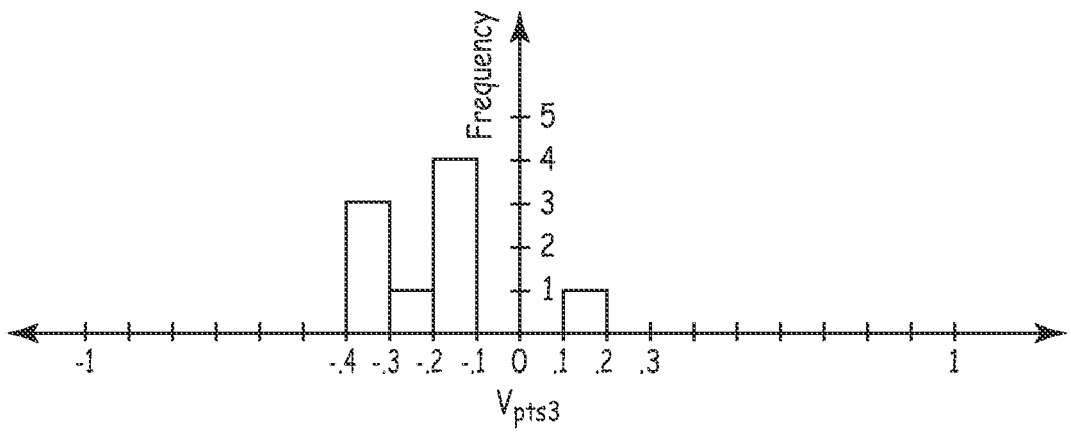

After normalization, each of the constituent components ($V_{pts1}$, $V_{pts2}$, and $V_{pts3}$) for each of the vector sample may then be used to create a respective histogram. For instance, FIG. 12A shows a histogram for $V_{pts1}$ resulting from ten samples. A respective histogram will likewise be obtained for each of $V_{pts2}$ and $V_{pts3}$, as shown in FIGS. 12B and 12C, respectively. The histograms may then be used to determine $V_{pt}$ based on most frequently-occurring values, median values, or using some other calculations. For instance, based on most-frequently occurring values illustrated in FIGS. 12A-12C, the detected posture vector $V_{pt}$ may be set to [0.4, −0.7, −0.1] or [0.5, −0.8, −0.2].

The samples $V_{pts}$ that are selected for use when determining $V_{pt}$ may additionally or alternatively be selected by some other condition associated with a patient. For instance, the samples selected to determine $V_{pt}$ may be those having an AC signal component having a particular direction or indicating a predetermined activity level (high activity level based on activity counts, for instance.)

The method of Equation 1 may be generalized to include the possibility of using multiple posture state samples $V_{pts}$ to derive the revised defined posture vector, as follows:

$$V_{rev} = (1-\alpha)f(V_{pts}, PTS \epsilon T) + \alpha V_{def} \quad \text{(Equation 3)}$$

In Equation 3, "f" represents some function applied to one or more samples $V_{pts}$ of the patient's currently-detected posture state vector $V_{pt}$. As set forth above, the function may utilize an average, a median, a minimum, a maximum, a most-frequently-occurring value, or any other function. The samples to which the function is applied include some subset T of the acquired one or more samples, wherein T may be determined by a filter specifying spatial requirements, time-related requirements, a state of a patient, and so on. If the set of samples that fulfill any such requirements is empty, then $V_{pts}$ is not generated and $V_{def}$ is not revised. In another embodiment, if the set does not include at least some minimum number of samples that fulfills all requirements, then $V_{pts}$ is not generated and $V_{def}$ is not revised.

In some embodiments, a very large number of samples may be used to derive $V_{pt}$. In such an embodiment, the vector obtained for $V_{pt}$ may be considered such a good representative of the posture state that this vector may be used to replace, rather than modify, the existing defined posture vector $V_{def}$. That is, $\alpha$ in Equation 3 above may be set to zero so that no weighting is accorded to $V_{def}$ in such instances.

The foregoing discusses the updating of $V_{def}$ for a given posture state as being triggered by a patient making a therapy adjustment. At this time, the therapy parameter set resulting from the therapy adjustment may also be updated for the posture state. This may be performed by simply storing the therapy parameter set resulting from the adjustment in a data structure such as that shown in FIG. 9 Alternatively, some adaptive algorithm that is similar to that used to update the defined posture vector may be used to update the therapy parameter set associated with the posture state. Such an algorithm may assign at least some weight to one or more parameters of a previous parameter value rather than merely overwriting the older value. Weighting factors may be parameter-specific in one embodiment.

While revision of a posture state definition may be prompted by a request from a patient to modify delivery of therapy, other mechanisms may be used to prompt the potential updating of a posture state definition. For instance, updates of posture state definitions may be performed systematically at predetermined times of the day and/or days of the week. The time/day selected to update one posture state need not be the same time/day selected to update a different posture state. If desired, the times/days selected for this purpose may be based on a patient's typical schedule. For instance, if it is known that a patient who is a bank teller will generally be in a leaning position corresponding to a Leaning posture state definition from 2:00 pm-3:00 pm on weekdays, it may be preferable to perform sampling during this time, with the goal of updating a posture vector (which may initially be an estimated posture vector) for a Leaning posture state definition based on the samples. Similarly, sampling may be performed periodically throughout the nighttime to update posture state definitions for the patient's Lying posture states.

Processing for potentially updating posture state definitions may occur at time intervals that may be varied, if desired. For instance, the frequency at which posture states are updated may be relatively high after implantation when the posture vectors still represent estimated values rather than those representing actual posture states of the patient. Some period of time after implantation, the frequency at which updating is initiated may be diminished to conserve power within IMD 12. As another example, updating may occur more frequently during some times/days than others. For instance, updating may be set to occur more frequently during week days so that work posture states (e.g., Leading Forward) can be adapted very readily, whereas updating may be performed less frequently during weekends.

Still other triggers may be used to prompt processing for updating of one or more posture state definitions. For instance, the detection of an AC component of the output of sensor 40 that has a substantially predetermined direction may prompt the updating of one or more posture state definition. More particularly, a patient's tapping on the reference face of IMD 12 will, in one embodiment, generate an AC activity component of a signal detected by sensor 40. Such an AC component may be extracted using commonly-known hardware and/or software signal filtering techniques. The AC component generated by the patient's tapping will, in one embodiment, have a direction that roughly corresponds to the patient's lying back posture vector. Detection of such a signal may trigger the sampling of the patient's current posture vector for use in potentially updating the defined posture vector. This mechanism allows a patient to settle into any posture state and thereafter provide, via tapping on the device, an indication of the desire to update the corresponding posture state definition for that posture state. This operation may be beneficially performed without the use of programmer 20, which the patient does not have to have handy in order to trigger the updating of the definition.

As another example, if an AC component of sensor signal is detected having a vector that is within some predetermined distance of the defined posture vector for the Upright posture state, and further if the AC component is indicative of a predetermined activity level (e.g., as by using activity counts) as may occur if the patient is walking, for instance, processing to update the Upright posture state may be triggered. Any one or more predetermined activity levels and vectors in predetermined directions may, in this manner, be used to trigger the updating of one or more associated posture states.

Potential updating of a posture state may additionally or alternatively be triggered by some other parameter indicative of a patient's state, activity level, direction of activity, type of activity, an indication of sleep or sleep onset, and so on. Such a parameter may be measured by one or more of sensors 40 and/or other sensors affixed to or carried by patient, and may include any physiological parameter measurable by existing or future sensor technology as described herein. This may include, but is not limited to, heart rate, blood pressure, a characteristic of blood such as glucose level, EMG or EEG signals, etc. As one example, when it is determined that the patient is likely asleep based on heart rate, activity level, and/or one or more other signals, processing to potentially update the Lying posture states may be triggered.

In one embodiment, the type of trigger mechanism that is used to prompt potential updating of a posture state may also be used to affect how updating may be performed. For instance, in cases wherein a patient is requesting a therapy modification, the patient may not always be completely settled into the target posture state at the time of the request. On the other hand, when "tapping" is utilized to trigger posture state modification, the patient may generally be more settled into position at the time of the trigger. Thus, the value selected for a in Equation 1 above may be smaller when the trigger is "tapping" versus a therapy modification request, thereby according more weight to the currently-detected posture vector when tapping is utilized.

In the foregoing manner, estimated posture vectors may be modified into vectors that more accurately represent the patient's actual posture states. Moreover, as the patient's condition changes in response to a changing health condition, the delivery of therapy, or for some other reason, the defined posture vectors will continue to adapt so that accurate posture classification may continue to occur irrespective of such changes. The updating of the defined posture vectors may take into account many factors, including the distance between $V_{pt}$ and $V_{def}$ (as determined using distance measurement techniques described herein or any other such known techniques), stability of $V_{pt}$ (as determined using time filters), a day/time indication, and other conditions associated with a patient's conditions or actions. Such other conditions may include the patient's activity level, a direction of detected activity (e.g., "tapping", walking, etc.), and/or measured physiological parameters as measured by one or more sensors 40 other than a posture state sensor. As discussed above, physiological parameters may include any that may be sensed by current or future sensor technology.

Some of the approaches described herein may also be used to automatically detect and correct for a "device flip" of the type that may occur when IMD 12 changes orientation within the pocket (e.g., rotates, flips, etc.), as may be the result of a patient with "Twiddler's Syndrome". Such a device flip may cause at least one vector to point in a direction that is roughly 180° from the direction in which the vector was originally pointing. For instance, patient 14 may rotate IMD 12 such that the reference face of the device is oriented towards the core of the patient's body rather than toward the cutaneous boundary. As a result, an upward posture vector referenced by an Upright posture state definition may now erroneously point towards the patient's feet. The patient will therefore no longer be accurately classified in an upright posture state.

Several mechanisms are available to detect a scenario similar to the foregoing. As one example method, when a patient's detected posture vector does not fall within any classified posture state, special flip detection processing may be initiated. Flip detection processing may determine whether the detected posture vector is within some predetermined distance of a vector that is "opposite of" (i.e., 180° from) a defined posture vector. If so, this determination may be retained for future reference, as by saving some indication in memory 36 of IMD 12. For instance, if the detected posture vector is within 10° of a vector that is opposite of the defined posture vector for the Upright posture state, an indication that the Upright posture vector may have "flipped" may be saved in memory 36. If such a determination is noted a predetermined number of times (e.g., M times within N samples), a device-flip warning may be generated.

In one embodiment, the likelihood of a device flip may be further confirmed by the use of AC components of the output of sensor 40, particularly in reference to an Upright posture vector. For instance, a DC posture signal may be sampled from sensor 40 while the AC components of the sensor signal indicate that the patient is engaged in a relatively high activity level (and thus is likely upright and active). It may be determined whether the detected posture samples obtained during this period of higher activity have a direction that roughly correspond to the detected posture vectors flagged for possible flip detection. If so, this may be considered a confirmation that a flip has occurred such that the upright vector is now pointing downward.

If it is concluded that flip detection has likely occurred, a notification may be generated. This may involve a tactile notification generated via IMD 12, such as a vibration or delivery of a discernable electrical stimulation pattern. This may additionally or alternatively involve an audible notice generated via the IMD or programmer 20, a text message or other alert communicated by programmer 20, or some other discernable indication. Such a notification may identify the posture state definitions to be recalibration (e.g., "Recalibrate all Posture State", "Recalibrate Upright Posture State", etc.). Such re-calibration may be accomplished via a user interface similar to that shown in FIGS. 6A and 6B, by tapping the device or requesting therapy adjustment when in a potentially-affected posture state in any of the ways discussed above, or by using some other re-orientation method. According to one aspect, this may involve re-deriving the posture vectors according to techniques described above, and with minimal effort on the part of the patient. For instance, in one embodiment, the patient may be prompted to recalibrate Upright and Lying Back posture states only (e.g., by activating an "ORIENT" function or use a tapping mechanism) while roughly assuming these posture states. In an alternative embodiment, the recalibration operation may instead automatically update a posture state definition to reference a vector that is 180° from the previously-referenced vector, thereby even further minimizing participation on the part of the patient.

Thus, in accordance with techniques described herein, vectors for posture state definitions may be automatically updated as the patient goes about daily life. This may even include updating vectors automatically upon detection of a potential device flip condition. As vectors are updated, it will be understood that the tolerances associated with those vectors are shifted in space. For instance, the cone that had previously surrounded the "old" vector will now be shifted in three-dimensional space to surround the revised ("new") vector. This will occur automatically by virtue of the change made to the vector.

In one embodiment, the size and/or shape of the tolerance may be updated automatically in much the same way the vector is automatically updated. As an example, IMD 12 may track the set of the recorded posture vectors that falls within a defined posture state over a predetermined period of time. If the identified set of the recorded posture vectors predominantly fall within a portion of the defined posture state, as automatically determined by IMD 12, IMD 12 may shrink the posture state definition such that its boundaries more closely match the portion in which the posture vectors predominantly fall, e.g., automatically or upon confirmation for a user. Returning to the example of FIG. 11A, a posture state definition for the Upright posture state may initially be described using cone 208, as may be described by a cone angle. However, based on recorded posture vectors over a period of time, IMD 12 may redefine the posture state definition so that the cone is enlarged or reduced. For instance, it may be determined that many detected posture vector samples are falling just outside of an outer edge of the spatial region associated with the posture state such that it is advantageous to increase that spatial region.

As another example, the spatial region associated with a posture vector may be automatically revised such that at least a specified percentage, e.g., 80-100%, of the recorded posture vectors for that posture state cone fall within the revised area. In such an embodiment, it may be beneficial to retain the various detected posture vector samples, $V_{pts}$, rather than disgarding samples after generation of a revised posture vector. For instance, such samples may be stored in a posture state history file 54 or in some other storage facility of IMD 12, transferred as by telemetry communication to programmer 20 or to another device (e.g., a server) for storage, or retained in another storage medium associated with the system. In this manner, revising a posture state definition may more generally comprise redefining a posture state vector and/or a tolerance, (e.g., a cone angle.)

As previously discussed, posture states include at least one of a posture and an activity component. The posture may be described using a vector. This vector is obtained by extracting a DC portion of the signal obtained from outputs of sensor 40 using low-pass filtering techniques. A high-pass filter may be employed to extract the AC portion of the signal, which describes a patient's activity. The AC portion may be used to derive an activity level, and may further be processed to obtain one or more vectors indicating a direction of motion, direction of velocity, a direction of acceleration, and so on. Processing of signals of sensor 40 to obtain a posture description and/or an activity component are described in U.S. patent application Ser. No. 12/433,029 filed Apr. 30, 2009 referenced above.

In view of the foregoing, it will be understood that a posture state definition may reference a vector that describes a posture state, and/or at least one other vector that describes an activity undertaken by the patient. While the various methods and systems described herein for adapting vectors are described in terms of postures assumed by a patient (e.g., Upright, Leaning Forward, etc.), these same mechanisms may be used to revise vectors for activities. For instance, a posture state definition used to detect when a patient is swimming may be associated with a predetermined activity level and velocity vector. Adaption of the activity vector over time may occur by obtaining one or more samples of sensor 40 while the patient is classified as being swimming, and using AC components of the samples to update the activity vector. If desired the DC component of the samples may be used to update the posture vector for the patient's swimming posture. Thus, any of the techniques described herein may be applied to updating posture and/or activity vectors associated with posture state definitions.

Figure 13:
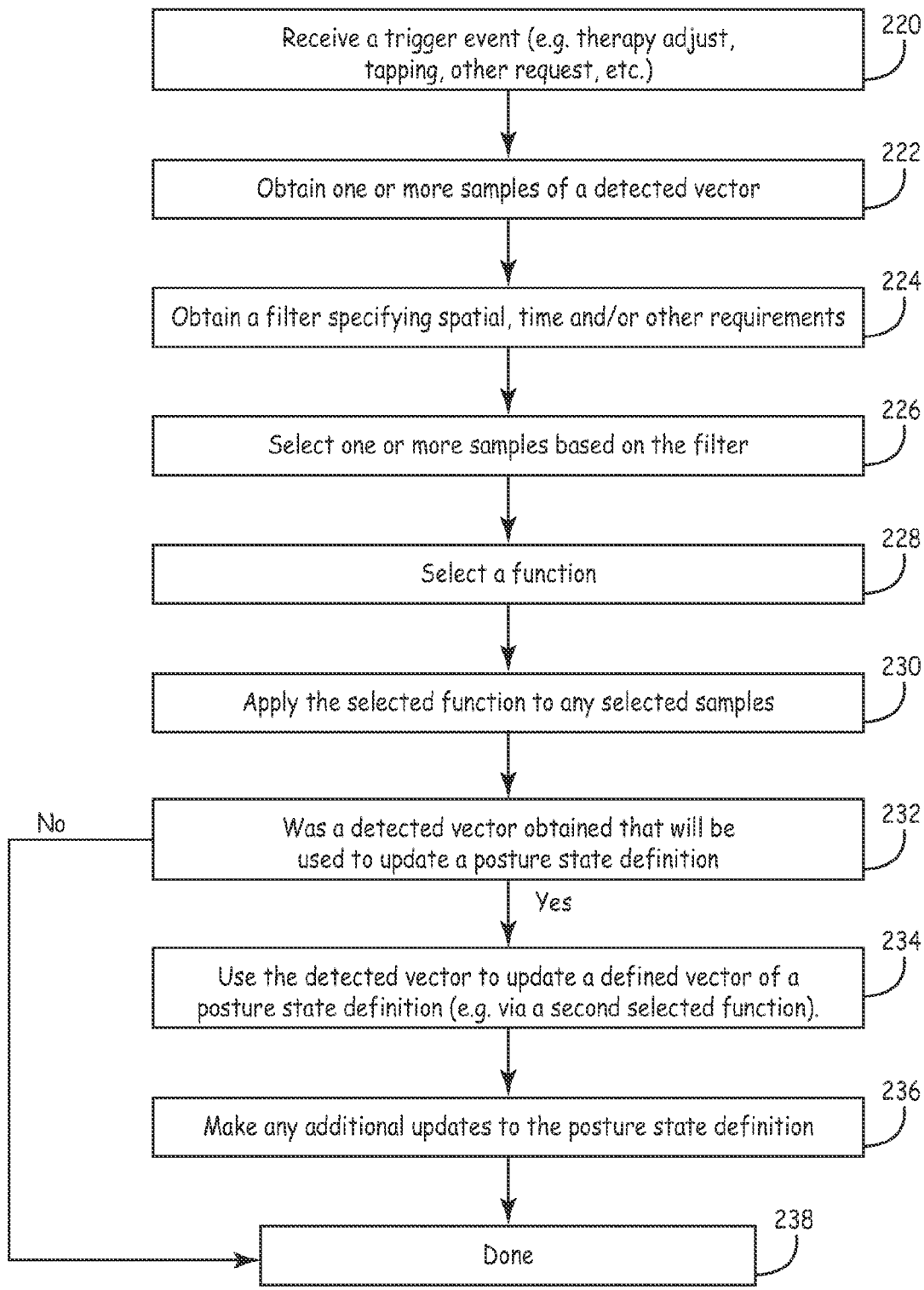
FIG. 13 is a flow diagram of one method of revising a posture state vector.

FIG. 13 is a flow diagram of one method of revising posture state vectors (that is, either posture vectors or activity vectors) according to the disclosure. A trigger event is obtained (220). The trigger may be, for instance, a request to adjust therapy that is being delivered to the patient. This trigger may instead be a time of day and/or day of the week, a sensed activity component (e.g., resulting from tapping, walking, etc.), some other parameter sensed by one of sensors 40 that is other than a posture state sensor (e.g., heart rate, EEG, EMG, glucose level, etc) and/or any other trigger.

Upon receiving a trigger, one or more vector samples are obtained (222). If desired, a filter may be obtained for use in filtering these acquired samples (224). The filter may be specific to a particular posture state, or may be selected based on some other consideration (e.g., time of day, day of week, time since implant, another patient parameter, etc.) The filter may specify spatial, time, or other requirements. The filter may be used to select one or more of the samples that fulfill the filter requirements (226). In some cases, the filter may indicate that none of the one or more sampled vectors are to be used.

Next, a function may be selected (228). This function may be applied to the selected samples, if any (230). Such a function may select one of the one or more selected samples or may instead obtain an average, median, most-frequently-occurring, maximum, minimum, or some other value.

It may next be determined whether application of the selected filter function resulted in a detected vector that will be used to update a posture state definition (232). Recall that in some cases, none of the one or more obtained vector samples meets the requirements of the filter, in which case, no updating of the posture state vector occurs. Therefore, processing is considered complete (238). However, if the application of the selected function to the selected samples does result in a vector to be used to update a posture state definition (232), this vector may be used to revise a defined vector of that definition (234). For instance, this may occur according to a weighting function that weights the defined vector and the detected vector. This is as exemplified in Equations 1 and 3 above, which employ a weighting factor α, which is selectable according to a posture state, a time and/or day, some parameter associated with the patient (e.g., an activity level and/or vector, a physiological parameter sensed by a sensor other than a posture state sensor, etc.), or some other consideration associated with the patient and/or system. Other changes may be made to the posture state definition (236), which may including adding or changing a therapy and/or other action to be associated with the definition, updating the tolerance associated with the updated vector, and so on.

In FIG. 13, updating of a defined vector occurs in multiple steps. The first step involves potentially obtaining a detected vector from one or more samples acquired as the result of occurrence of a trigger event, as shown in step 230. After such a detected vector is obtained, it may be used to update a defined vector of a posture state, as shown in step 234. A variation of this approach collapses the processing of the collected samples and subsequent updating of the defined vector into a single step. This alternative embodiment may utilize a history file that retains the detected vector samples acquired as a result of multiple trigger events. For instance, each time a therapy adjustment is made, vector samples obtained as the result of this adjustment may be stored in the history file along with vector samples stored as the result of previously-requested therapy adjustments. If desired, storing of new vector samples may cause the oldest samples to be discarded so that no more than a predetermined maximum number of samples are stored at a given time within the history file. If desired, only vectors meeting requirements of a filter are stored, with the filter being defined according to any of the approached described above.

Once new samples are acquired, a selected function may be applied to all of the vector samples in the history file. This function may involve use of averaging, determining a median or most-frequently occurring value, a minimum value, a maximum value, a weighted average, or any other function. In this manner, the processing exemplified by steps 230 and 234 of FIG. 13 are collapsed into a single set that receives as input the most recently-acquired vector samples and previously-acquired vector samples. Such an alternative approach may require more resources to complete, including more storage space to store the previously-acquired samples, as well as additional processing capabilities (which is associated with power consumption.). However, this processing of a larger number of samples may prevent any vector that is an anomaly from being accorded too much weight. It may be noted that a similar result may be achieved using the multi-step approach by selecting a larger weighting factor (e.g., larger value of α) so that more weight is accorded to the defined vector, which may be an average or some other value obtained from many previously-acquired samples.

Figure 14:
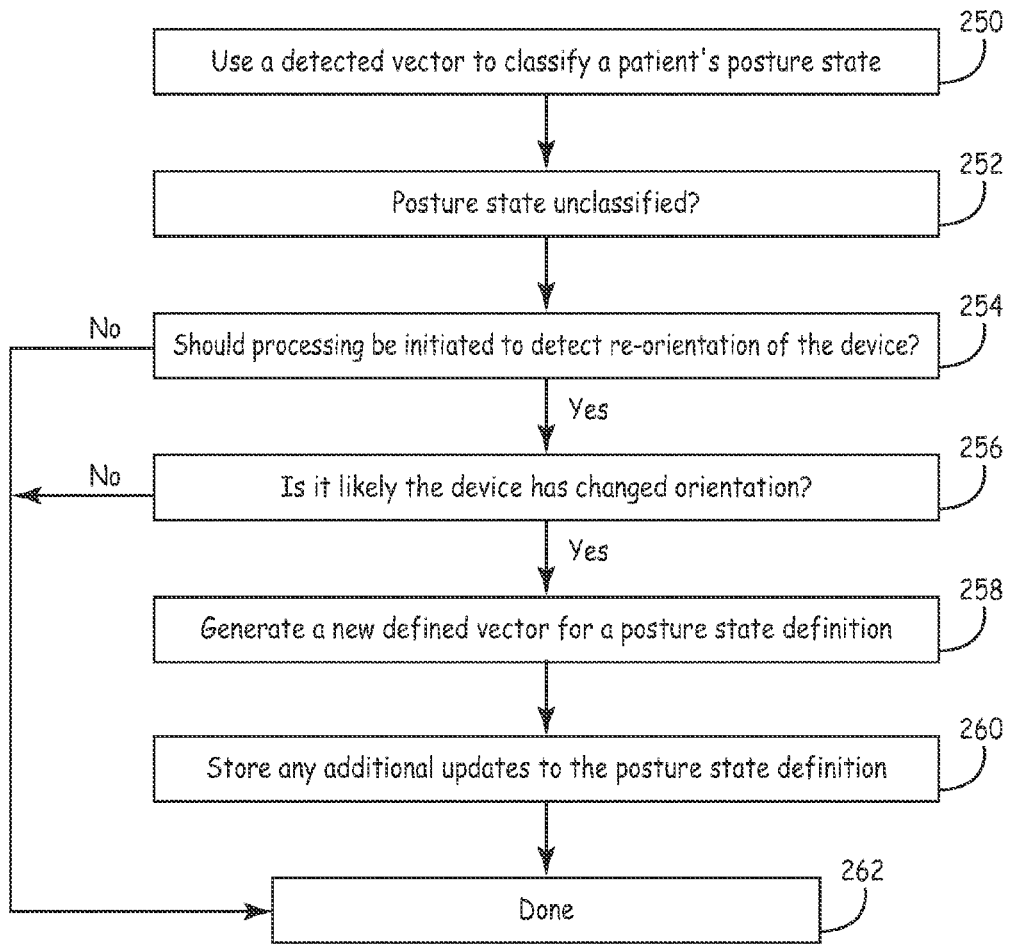
FIG. 14 is a flow diagram of one method of detecting and correcting for a change in orientation of a medical device.

FIG. 14 is a flow diagram illustrating one mechanism for detecting a device flip according to exemplary techniques described herein. A detected vector, as determined according to one or more of the steps shown in FIG. 13, may be used to classify a patient's posture state (250). If this processing results in the patient being in an Unclassified posture state (252), it may be determined whether flip-detection should be performed (254). If not, processing may be considered completed (262). Otherwise, if flip-detection is to be performed, it may be determined whether it is considered likely that the device has changed its orientation relative to the patient (e.g., as "flipped" or "rotated" in the pocket, 256). If so, the detected posture vector may be used to revise the defined posture vector for a posture state definition affected by the device flip (258). For instance, the detected posture vector may merely be substituted for the defined posture vector. Alternatively, the defined posture vector may be modified by 180°, or some other modification technique may be used. Any other updates that are needed may be made to the posture state definition (260), including revision of the tolerance, or association of the posture state definition with a different therapy.

Heretofore, the described techniques have been discussed within the context of a limited set of posture states that require at least some calibration before use, either by the system (e.g., according to automated techniques described herein) or by human intervention. These posture states, which are defined by a corresponding predetermined set of posture state definitions, may be named (e.g., Upright, Reclining, Lying Left, etc.). Such posture states may be associated with a representation such as an avatar on a user interface that further identifies that posture state. Example user interfaces are shown by FIGS. 6A, 6B, 8B, and 8C. Generally, the predetermined set of posture states that may be calibrated according to the foregoing techniques will include those most likely to be assumed by a patient.

As is appreciated, as the patient goes about daily life, the patient may assume a wide range of posture states. As such, it is conceivable that sensor 40 may provide a signal indicative of any vector in three-dimensional space. Only part of this three-dimensional space is allocated to the predetermined set of posture states that were calibrated. For instance, FIG. 4 represents three predefined posture states (Upright, Lying Left, and a Leaning Forward posture state) each associated with a region depicted as a cone. The space lying outside of these cones, sometimes referred to as hysteresis space, is not associated with any pre-defined posture state. In the above discussion, when a patient's detected posture vector falls within this space, the patient's posture state is described as being Unclassified. This classification may result in therapy remaining unchanged. Alternatively, this classification may cause the patient to receive a therapy associated with the Unclassified posture state (e.g., using "benign" parameter values). Thus, according to the approach described above, this space is homogeneous. That is, no matter where in the hysteresis space that a patient's detected posture vector falls, the same type of action will be taken.

According to yet another paradigm, hysteresis space may be filled with vectors that are captured "on-the-fly" in a dynamic manner. Each such vector represents a corresponding posture state, each of which may be associated with a set of one or more parameter values that may be used to control therapy. These vectors are collected over time rather than being calibrated during an automated or manual calibration procedure. After such vectors are captured, they may be used to control therapy delivery. That is, when a patient's detected posture vector is substantially the same as one of the vectors in hysteresis space describing one of the dynamically-captured posture states, the associated parameters are used to control therapy. In this manner, the hysteresis space is no longer homogeneous. Rather, it may be viewed as a virtually unlimited set of points (or vectors), each being associated with a different posture state and a corresponding therapy parameter set if desired. These therapy parameter values within hysteresis space may be used to deliver therapy to the patient as the patient transitions from one of the predetermined (calibrated) posture states to the next. For instance, as a patient transitions from the Upright to the Lying Left posture state of FIG. 4, an intermediate vector falling within the hysteresis space between the Upright and Lying Left cones may be associated with one or more therapy parameters. These parameter values may be used to transition therapy from levels associated with the Upright posture state to levels corresponding to the Lying Left posture. In this manner, therapy changes may occur in a more gradual, continuous fashion than if only a few predetermined calibrated posture states (e.g., Upright and Lying Left) are used to control therapy delivery during this transition. If desired, any number of vector/parameter associations may be created within hysteresis space to make transitions as gradual as desired.

As previously discussed, the vectors within hysteresis space may be acquired as the patient goes about daily life rather than being obtained during an automated or manual calibration procedure. For instance, the occurrence of a trigger event, such as the patient requesting a therapy adjustment, may prompt the capturing of the output of sensor 40. If the captured output represents a vector within hysteresis space, that vector may be recorded along with the therapy parameters to be associated with the vector. This record may be stored within a data structure similar to that shown in FIG. 9, or in a separate data structure. Thus, posture states, as described by associated vectors, may populate hysteresis space over time. Such posture states need not be part of any pre-identified set of posture states that is supported within the system at the time of device deployment, and need not be identified at device calibration time. Rather they are dynamically captured over time and used to populate at least part of the three-dimensional posture space.

As may be appreciated, the concept of forming associations between posture states and therapy parameters dynamically as the patient goes about daily life need not be used merely to populate hysteresis space, but may be extended to populate all of three-dimensional space in one embodiment. In other words, instead of associating some portions of three-dimensional space with predetermined identified posture states such as Upright, Lying Left, Lying Right, and Reclining that require some degree of calibration (either automated or manual), all of three-dimensional space may instead be populated with a set posture state associations that are acquired over time. Each such association pairs a posture state (e.g., as may be defined by a posture state vector) to at least one corresponding therapy parameter value. None of these posture states that are collected over time need be associated with a named position (such as "Upright") if desired. Moreover, none of the vectors that describe the posture states need be identified during any calibration procedure. Embodiments that populate just hysteresis space with such posture state/parameter associations, as well as embodiments that populate all of three-dimensional space with such associations, are discussed below in reference to the remaining figures.

Figure 15:
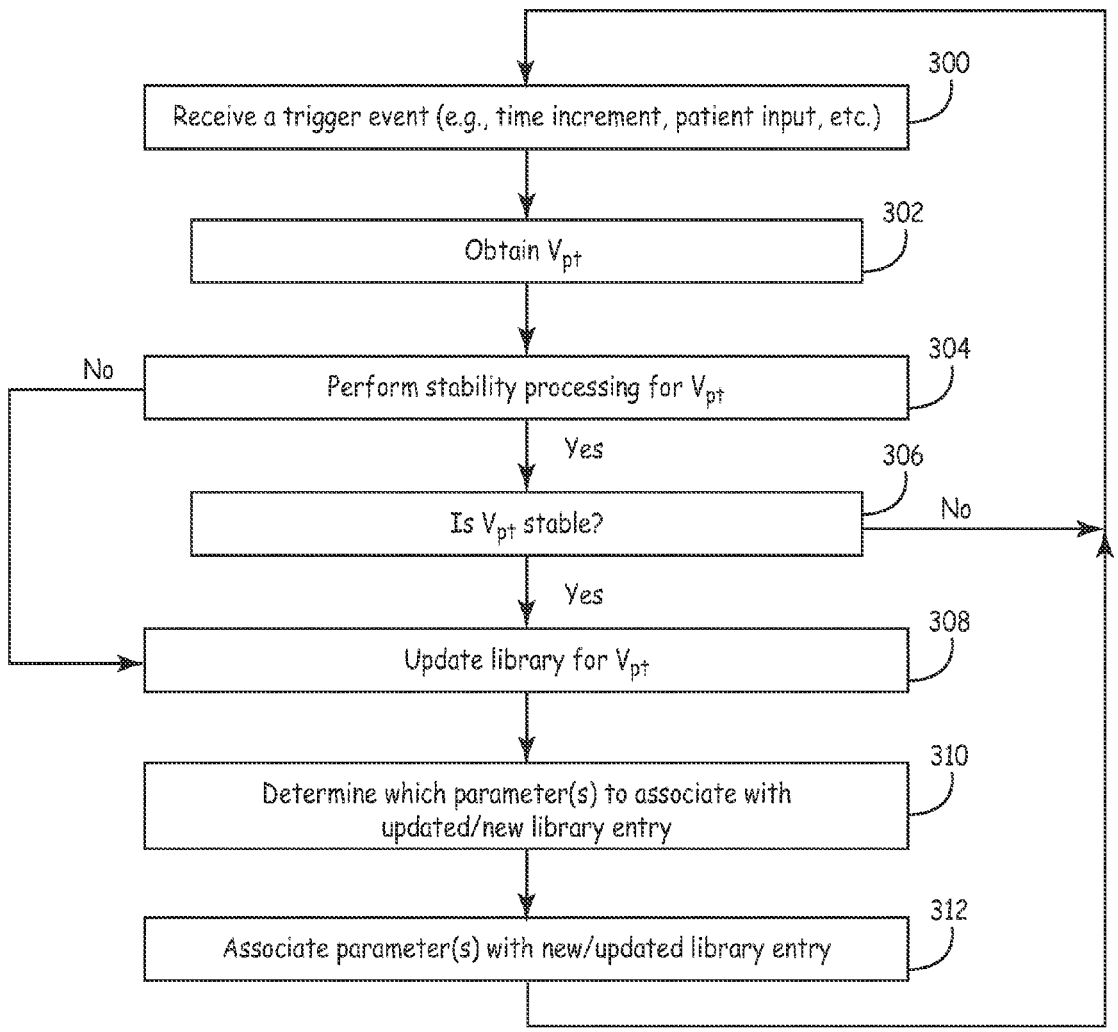
FIG. 15 is a flow diagram illustrating one example method of populating a library with vectors not associated with any predetermined posture state.

FIG. 15 is a flow diagram illustrating one example method of populating at least a portion of three-dimensional posture space with vectors that are not necessarily associated with any predetermined named posture state. Rather, each such vector represents an associated point in space and is associated with at least one therapy parameter value. As discussed above, such a method may be employed to add "filler points" to hysteresis space, which is the space that resides outside of a set of predetermined posture states. Alternatively, this type of process may be practiced to obtain all of the vectors contained within all of three-dimensional space in a manner to be discussed further below.

The method commences by receiving a trigger event (300). As was the case involving step 220 of FIG. 13, the trigger event may be, for instance, a request from a patient to adjust therapy. This trigger may instead involve the patient tapping on the device. Some other activity component detected by sensor 40 may be used as a trigger event, such as when the patient is moving in a particular direction. The trigger may instead be expiration of a timer, as may be the case if vectors are to be collected at regular periodic intervals. Such a trigger may be a specific time of day and/or day of the week. Some other parameter sensed by one of sensors 40 that is unrelated to posture state (e.g., heart rate, EEG, EMG, glucose level, etc) may provide the trigger event. Any other trigger event may be used in the alternative.

In response to the trigger event, the system acquires the patient's detected posture vector, $V_{pt}$, from sensor 40 (302). As discussed above, this vector is indicative of the patient's posture state at substantially the time that vector was acquired.

Next, it may be determined whether stability processing for this vector should be performed (304). Stability processing is performed to determine when the patient's posture state has settled into a stable target posture state. As an example, a patient may provide a therapy adjustment that is intended to correspond with a target posture state to which the patient is in the process of transitioning. Because the patient's posture state is changing, a vector captured at the moment the adjustment is entered may not necessarily represent the posture state that the patient intends to associate with the therapy adjustment. Stability processing must be used to locate a time, if any, when the output of sensor 40 is relatively unchanging, indicating the patient has finally achieved the target posture state. At that time, the vector associated with this stable posture state may be determined and associated with the therapy parameter adjustment.

The need to initiate stability processing may be determined based on the type of trigger event that is received. For example, if the trigger event involves a patient therapy adjustment, it may be desirable to initiate stability processing for reasons discussed above. That is, the patient's therapy adjustment may, or may not, correspond with the time period in which the patient settles into the final target posture state. Locating the point in time at which the patient's posture state is stable will allow the therapy parameters provided with the adjustment to more accurately be correlated with the intended posture state.

In other cases, it may be undesirable to initiate stability processing. As an example, if a sample vector is to be obtained upon expiration of a timer, or upon receipt of a predetermined sensor output (e.g., when the patient "taps" on the device to generate a particular acceleration vector), it may be unnecessary to perform stability processing. In these types of situations, it may be known that the detected posture vector being sensed at the time of the trigger event is the vector that is intended for capture, and thus there may be no need to impose the delay and expend the resources (e.g., power expended by the processing steps) to perform the stability check. In still other cases, stability processing may be performed any time a trigger event is received without regard to the type of event. In still other scenarios, stability processing may be performed only for trigger events that occur at certain times of days or days of the week. Thus, determining if and when to perform stability processing may be accomplished in many ways in various embodiments.

If it is determined that stability processing is to be performed in step 304, execution continues to step 306 where it is determined whether the detected posture vector $V_{pt}$ is stable. Such a check will involve locating a period of time following the trigger event, if any, when $V_{pt}$ stabilizes, and deriving a vector $V_{stable}$ that represents the stable value for the patient's detected posture vector that is occurring during this time period. Examples of performing stability processing are provided below.

If, in step 306, there is no time period when $V_{pt}$ is determined to be stable, processing returns to step 300 to wait for another trigger event. On the other hand, if a time period is detected when $V_{pt}$ is stable, the stable value for the patient's detected posture state as determined in step 304 is used to update a library of vector entries (308). This may involve creation of a new library entry, or updating an existing library entry, as will be described in detail below. Such a library entry may be similar to that shown in FIG. 9, and will involve the association of the posture state (e.g., as described by a vector) with at least one parameter. Unlike the example entries illustrated in FIG. 9, however, the updated/new library entry may not, at least initially, be associated with any named posture state. Rather the entry may represent any point in three-dimensional space that the patient occupied contemporaneously with the occurrence of the trigger event and that satisfied the stability requirements to prompt creating/updating of the library. Of course, if desired, the user may be provided an opportunity to name vectors as they are dynamically captured. This is discussed further below.

Next, the one or more parameter values that are to be associated with the detected posture vector are determined (310). For purposes of this discussion, such parameter(s) are described as controlling therapy delivery. However other types of parameters that control other aspects of the system may be associated with the vector instead of, or in addition to, therapy parameters if desired. For instance, parameters that control power consumption of the device, or other operational aspects, could be controlled based on posture state, if desired. The manner in which the parameter values are determined may depend on the type of trigger event that initiated capturing of the vector. If the trigger event involved a patient therapy adjustment, the therapy parameters specified by the patient may be associated with the vector. Similarly, if the trigger event involved patient tapping, the therapy parameters in use at the time that the tapping occurred may be associated with the vector since it may be safely assumed that the patient adjusted the parameters in accordance with his/her preferences before initiating the tapping to record the association. On the other hand, if the trigger event is not volitional, such as the expiration of a timer, or an output of a sensor that is not triggered by an act of the patient, some processing may be performed to determine which therapy parameters to associate with the new/updated library entry. Examples of this processing are set forth below.

Once therapy parameters are obtained, they may be associated with a posture state, which is described by a vector in this example (312). This may occur by storing the therapy parameters in the same library entry in which the vector was previously stored, or by using some other association mechanism known in the art (e.g., associating two different entries via pointers, etc.). Processing then returns to step 300 to await the receipt of another trigger event.

Returning to step 304, in one embodiment, it may be desirable to skip the stability processing for reasons discussed above. Processing therefore proceeds to step 308, as indicated by arrow 303. There, vector $V_{pt}$ may be used to create a new library entry or update an existing entry. The therapy parameters to be associated with the vector $V_{pt}$ are determined in step 310. An association between these parameters and the new/updated library entry is created in step 312. Processing then returns to step 300 to await another trigger event.

As previously described, the process of FIG. 15 may be used to obtain "filler points" within hysteresis space that are outside of the regions that have been associated with predetermined calibrated posture states. In this type of embodiment, when a trigger event results in the capture of a new posture vector $V_{pt}$, it may be desirable to first determine whether that vector lies within a space assigned to a predetermined named posture state (e.g., Upright). Only if the vector does not lie within such a space will the processing of FIG. 15 be performed. Such an embodiment allows the pre-existing posture states to take precedence in the control of the system. In a more general sense, however, the process of FIG. 15 may be used to dynamically populate all of three-dimensional space with associations between posture states and control parameters such that there is no longer a need for predetermined posture states, as is described further below.

Using these techniques, the dynamically-generated posture states may be employed to deliver therapy or control other aspects of the system based on the detected posture states of the patient. Specifically, processor 34 and/or a processor of a programmer 20 may receive from the sensor a signal indicative of a detected posture state of the patient. The processor may then determine if the detected posture state is represented by one of the dynamically-created associations between posture states and therapy or other parameters. If so, the corresponding parameter values may be used to control delivery of therapy to the patient and/or to control another aspect of the system.

Next, a more detailed discussion is provided concerning stability processing. As described above in reference to step 304, stability processing may be desired when a trigger event prompts the capturing of a detected posture vector. Such processing will be used to identify a time period, if any, when the patient's posture state is stable enough to meet the stability requirements of the system. In one embodiment, such requirements may be programmably selected by the manufacturer, clinician, and/or the patient.

In one embodiment, stability processing is performed in a manner that is similar to the processing described in reference to FIG. 11B. Such processing involves both a search window having a first predetermined search time and a stability window having a second predetermined stability time that is shorter than the search time.

Figure 16:
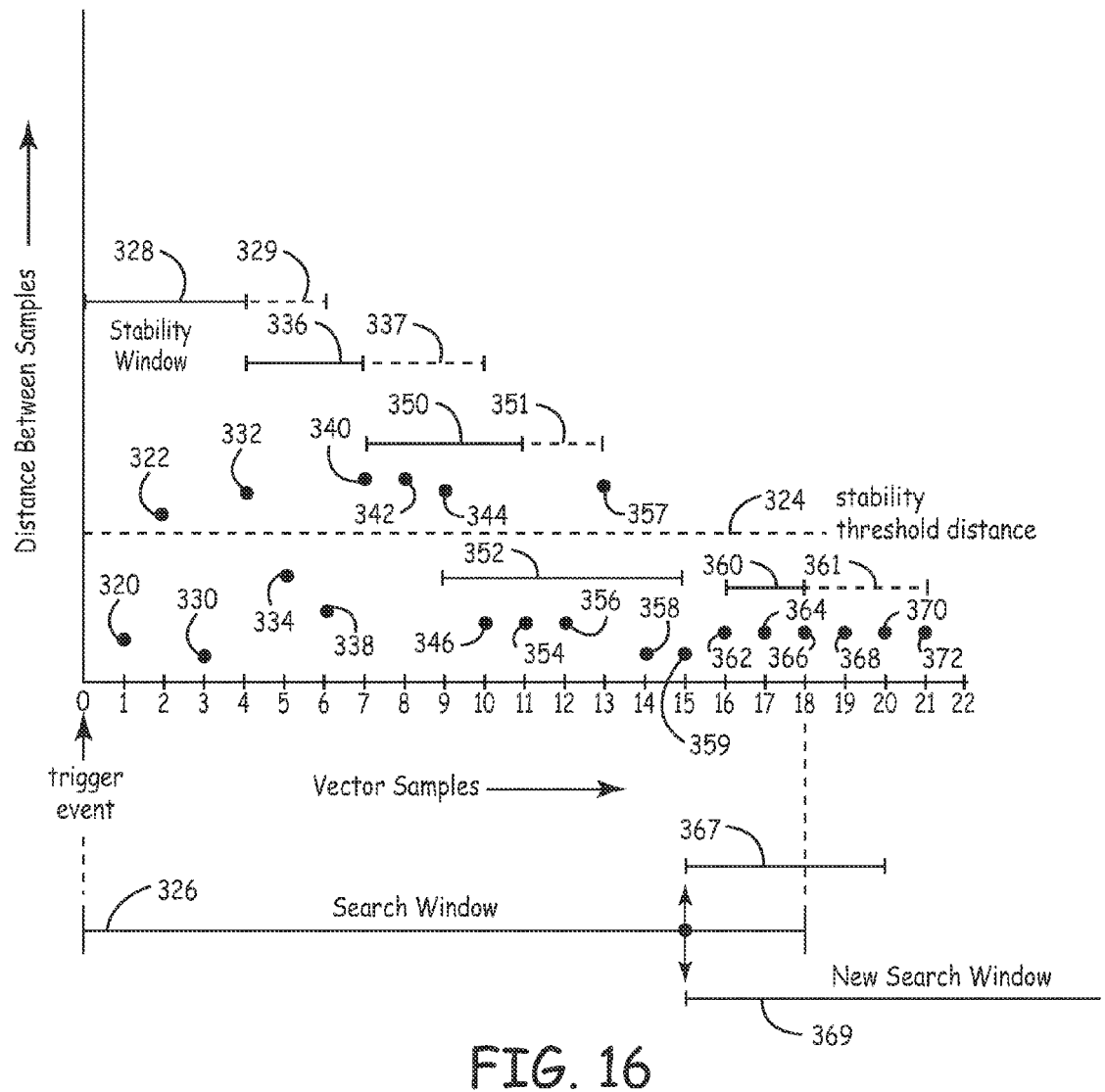
FIG. 16 is a conceptual diagram illustrating the use of a search window and stability window to evaluate stability of a detected posture state vector.

FIG. 16 is a conceptual diagram illustrating the use of a search window and stability window to evaluate stability of a patient's detected posture vector $V_{pt}$. The X axis of this diagram represents samples (designated samples 0, 1, 2, and so on) of the detected posture vector $V_{pt}$ that are collected at regular time increments. The Y axis represents distance between successive vector samples. In particular, point 320 represents a distance between sample 0 and sample 1, point 322 represents a distance between sample 1 and sample 2, and so on. This distance may be measured and described in terms of an angle, a Euclidean distance, a straight-line distance, a city-block distance, a Minkowski distance, using a trigonometric function, or using some other measure of the separation between successive samples of $V_{pt}$.

Dashed line 324 represents a stability threshold distance. Points lying below this dashed line represent successive samples that are close enough to one another to be deemed to have met the stability threshold distance requirements of the system. Points above this line represent successive samples that have not met this requirement. For instance, point 322 lies above this line, indicating that sample 2 may lie far enough away from sample 1 to indicate a shift may be occurring in the patient's posture state. In one embodiment, the stability threshold distance may be programmably selected by a manufacturer, clinician, patient, or by another means.

For purposes of this discussion, it will be assumed that a trigger event occurs at time 0, which corresponds with the capturing of detected posture vector sample 0. At this time, a search window 326 and a stability window 328 are started. The lengths of these two windows may be selected programmably in any of the ways mentioned above.

Next, the system determines whether, for the duration of the stability window, the samples within this window satisfy the stability requirements of the system. For illustration, it will be assumed that the stability requirement for this system dictates that M out of N of the most-recent samples lie not more than the threshold distance away from the preceding sample. For instance, assuming M and N are set to "3" and "4", respectively, not more than 3 out of the most-recent 4 samples may be more than the stability threshold distance from the preceding sample. In one embodiment, M and N may be programmably selected.

The example of FIG. 16 shows the distance between samples 0 and 1, as represented by point 320, is less than the threshold stability distance indicated by dashed line 324. However, sample 2 is more than the threshold distance away from sample 1, as indicated by point 322. Sample 3 is less than the sample distance away from sample 2, as indicated by point 330, but sample 4 is more than the threshold distance from sample 3, as indicated by point 332. The net result is that when sample 4 is received, 2 out of the most-recent 4 samples are farther away from the preceding sample than the stability threshold distance, thereby failing the stability requirements selected for the system. This failure to satisfy the stability requirement causes the stability window 328 to be re-started shortly after receipt of sample 4 and before that window would have otherwise expired, which would have occurred at the end of dashed segment 329. That is, if left to run until completion, stability window 328 would have continued until sometime shortly after receipt of sample 6.

In an alternative embodiment, it may be desirable to set "N" to be the total number of samples that will be collected within a stability window (e.g., six samples in the current illustration), with the stability window set to expire shortly after the last sample is obtained. In this embodiment, each stability window will run almost to completion before it is determined whether the stability requirement has been met by that window, and whether another stability window must be re-started.

Upon failure to meet the stability criterion within stability window 328, another stability window is started, as indicated by line 336. There are several ways to re-start this stability window. In one embodiment, the stability window can be re-started to exclude all of the samples that have previously been considered. In this type of scenario, stability window 336 could be re-started with sample 5 represented by point 334.

In another embodiment, one or more of the previously-considered samples may be swept into the next stability window 336, effectively allowing the current stability window to overlap in time with the previous stability window. For instance, the stability window may be re-started to include no more than a predetermined number of samples that fail the stability threshold distance requirement. The embodiment shown provides an illustration of this type of system, with the predetermined number being set to "one". That is, the next stability window "backs up" to the point where only one previous sample fails the stability threshold requirement. Thus, the next stability window 336 includes sample 4 represented by point 332, which is more than the stability threshold distance from sample 3.

In yet another type of embodiment, the next stability window may be re-started to include no more than a predetermined number of samples that fail the stability threshold distance requirement, and to further include all intervening or directly-preceding samples that don't fail the stability threshold distance requirement. In this type of scenario, stability window 336 could include not only sample 4 represented by distance point 332, but also sample 3 represented by distance point 330, since this directly-preceding sample passed the stability requirements.

Returning again to the example of FIG. 16, once stability window 336 is started, the system determines whether stability requirements are met in a manner similar to that described with respect to window 328. As was the case for window 328, only two of the first four samples within window 336 satisfy the stability criterion, with points 332 and 340 representing failing samples 4 and 7. As such, stability window 336 again is terminated before it is allowed to fully expire, which would otherwise have occurred as indicated by dashed portion 337. As a result, another stability window 350 is started. The vector samples included within this window again fail to satisfy the stability requirements, as indicated by points 340 through 346 and dashed portion 351 of the stability window 350.

During stability window 352, three of the first four vector samples 9 through 12 meet the stability criterion, as indicated by points 344, 346, 354 and 356. Therefore, stability window is not terminated after four samples, as were the previous three stability windows. Instead, a fifth sample 13 is collected. This sample does not satisfy the stability threshold distance requirements, as indicated by point 357. However, since three of the last four samples do meet the requirements, the stability window is not terminated. The next two samples 14 and 15 are acquired that meets the stability threshold distance requirements, as indicated by points 358 and 359. As each such sample is received, the requirements of the M-of-N filter are met such that the stability window is not terminated prematurely. Shortly thereafter, the stability window expires. As a result, a stable vector was located for the trigger event.

A stable value $V_{stable}$ may be derived from the samples 9-15 included within the stability window 352. Such a value may be derived by applying some selected function to all, or a predetermined subset of all, samples within the window. This function may be an average, a median, or any other desired function. For instance, $V_{stable}$ of the current example may be derived by averaging samples 9-15. In another embodiment, an adaptive algorithm such as that reflected by Equation 1 above may be used to generate this value. If desired, some weighting function may be employed, as by weighting samples collected later in the window more heavily than those collected earlier. If desired, $V_{stable}$ may be a running average or some other value that is computed as each sample is received. As yet another possibility, some subset of samples within the window may be selected to generate $V_{stable}$. For instance, a predetermined number of samples within the stability window that are all within some predetermined distance of one another may be used for this purpose, with vectors that are farther away being excluded.

Next, assume for example purposes that the samples included within stability window 352 had not satisfied the stability requirements. Rather, each stability window elapsed without the fulfillment of the stability requirements of the system. As a result, stability window 360 may be initiated. This window includes samples 16-19 represented by points 362-368, respectively. This stability window is interrupted before it expires by the expiration of the search window 326 at about the time sample 18 is collected. The premature expiration of stability window 360 is indicated by dashed portion 361. In the embodiment described in more detail below, the expiration of the search window 326 before expiration of stability window 360 will result in the detected posture vector being deemed unstable. Other embodiments are possible, however. In an alternative embodiment, any stability window that is started before expiration of the search window, such as stability window 360, may be allowed to run until completion even after the search window expires. In this alternative embodiment, $V_{pt}$ would be considered stable based on the vectors received for samples 16-21, represented by points 362-372. The embodiment that is selected for use is a matter of design choice, and may be based on history data.

The foregoing discussion has assumed that search window 326 will expire without interruption. However, in one embodiment, if another trigger event is received within search window 326, that search window and the stability window that is active at that time may be terminated and new search and stability windows started. For instance, FIG. 16 illustrates another trigger event occurring around the time sample 16 is received, prompting the initiation of search window 367 and stability window 369.

Figure 17:
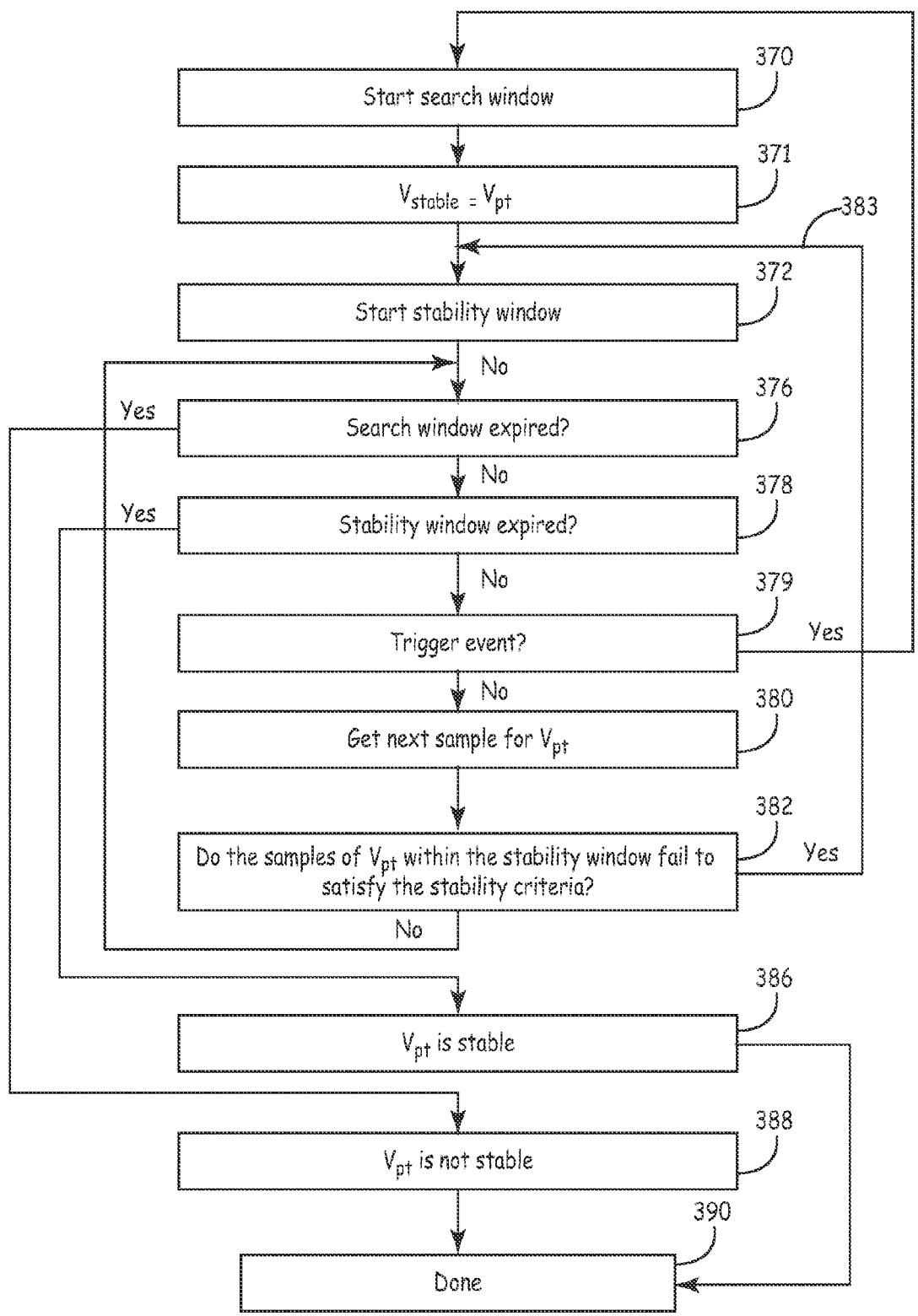
FIG. 17 is a flow diagram of one example method of determining posture state vector stability.

FIG. 17 is a flow diagram of one example method of determining vector stability in a manner similar to that described above with respect to FIG. 16. Upon initiation of the processing, which may be prompted by receiving a trigger event of a particular type, a search window is started (370).

Next, the value for $V_{stable}$, which is the value that will represent the patient's stabilized vector, may be initialized to the value of the first vector sample obtained when the trigger event occurred, $V_{pt}$ (371). This value may be updated during the processing steps of FIG. 17, as will be described below.

A stability window is started that may be shorter than the search window (372). The length of the stability window, as well as that of the search window, may be programmably selected. In one embodiment, the search window may be between 2 and 10 minutes long and a stability window may be between 1 and 5 minutes long. In one specific embodiment, the search window may be selected as being 7 minutes long while the stability window is 2 minutes long. In another embodiment wherein the search and stability windows are a same length, both windows are set to 3 minutes.

Next, it may be determined whether the search window has expired (376). If not, it may be determined whether the stability window has expired (378). If neither window has expired, it may be determined whether another trigger event has been received while stability processing for a previous trigger event is still ongoing (379). This may occur, for instance, if a patient provides two therapy adjustments that follow closely in time to one another such that the search and stability windows resulting from the first trigger event have not yet expired when the second trigger event is received. If this occurs, in one embodiment stability processing will start over by returning to step 370. As discussed above in regards to FIG. 16, this will involve restarting both the search and stability windows (370, 372), and re-initializing the value for $V_{stable}$.

If, in step 379, another trigger event has not been received, the next sample of the patient's detected posture vector, $V_{pt}$, may be obtained (380). It may then be determined whether the samples of $V_{pt}$ falling within the stability window fail to satisfy the stability criteria (382). As noted above, the stability criteria may involve one or more requirements, each of which be programmably selected. Whereas FIG. 16 illustrates a single requirement involving an M-of-N filter, multiple such requirements may be used to determine whether the vector samples are stable. This is described further in regards to FIGS. 18 and 19 below.

If the samples of $V_{pt}$ that fall within the current stability window have not failed the stability criteria, processing may return to step 376 to determine whether the search window expired. If so, according to one embodiment, $V_{pt}$ will not be considered stable (388), since the search window expired before it was detected that a stability window expired. Processing is then considered complete (390). If, however, the search window has not expired in step 376, it is determined whether the stability window has expired (378). If it has, the stability window has concluded without the samples within that window failing to meet the stability requirements, and the patient's detected posture state vector is considered stable (386). The stable value that will be employed for the detected posture vector may be determined in any number of ways, as discussed above in regards to FIG. 16. Further examples are provided in regards to FIG. 18 discussed below. Processing is then considered complete (390).

Returning to step 382, if the samples of $V_{pt}$ that fall within the current stability window fail to satisfy the stability criteria, processing returns to step 372 to restart the stability window. As previously described, this may involve sweeping one or more previously-considered samples into the next stability window. Processing then continues in the aforementioned manner.

As discussed above, determination of stability of the patient's posture state vector may be performed in step 382 of FIG. 17. Many different combinations of one or more requirements may be used in making this determination. Such requirements may be programmably selected by a manufacturer or in some embodiments, an end-user. Selection may be based on analysis of past data, for instance.

Figure 18:
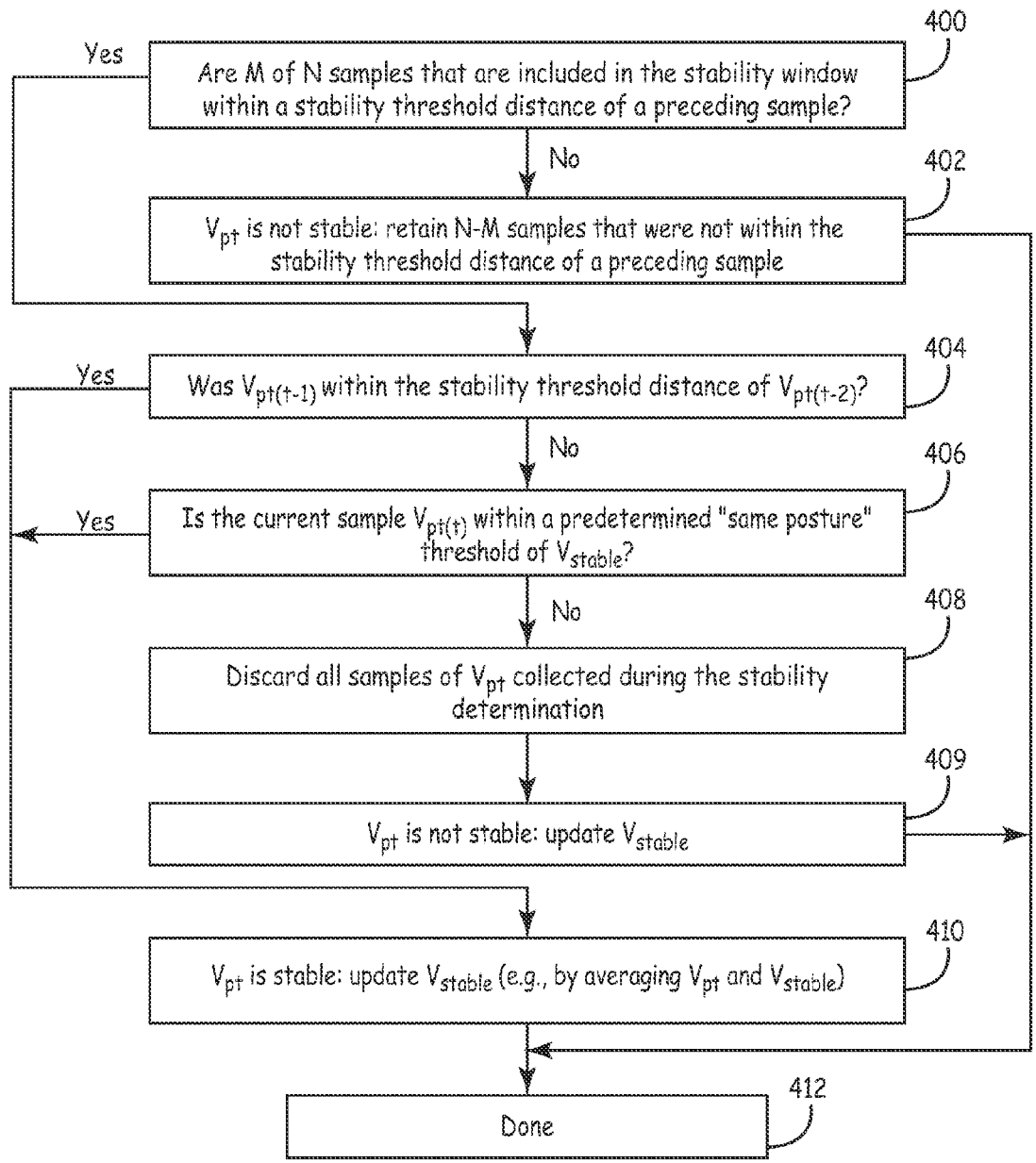
FIG. 18 provides one method of performing stability processing according to the current disclosure.

FIG. 18 provides one example set of requirements that may be used to determine stability. First, an M-of-N filter is used to determine overall stability of the samples within the stability window (400). As previously discussed, this involves determining whether M of N of the samples included in the stability window is within a stability threshold distance of a preceding sample. As discussed in relation to FIG. 16, this may involve iterative processing as each new group of N successive samples is acquired within the stability window. For instance, when a first group of N samples is available within the stability window (e.g., when the first four samples are available in a stability window of FIG. 16), it may be determined whether these samples meet the requirements of the filter. If so, the next group of N successive samples available within the window is considered, and so on. If all such successive groups of N successive samples within the stability window meet the M-of-N filter requirements, the vector is considered to be stable.

In another embodiment, N may be set to include the total number of samples that will be collected within a given stability window. For instance, returning to FIG. 16, if N is set to "six", which is the total number of samples collected within a given stability window, the determination as to whether the requirements of the M-of-N filter have been met will be made only once for each stability window, after the sixth and last sample is collected within that window.

Returning to FIG. 18, if the M-of-N filter requirement of step 400 is met, processing continues to step 404 and subsequent step 406. These two steps are designed to determine whether the most-recently-received of the current N samples (which will be referred to as sample $V_{pt(t)}$ and the immediately-preceding sample $V_{pt(t-1)}$) indicate the possible onset of a posture shift. If a change or shift of the patient's posture state is underway (e.g., the patient is preceding to move), the N current samples should not be considered indicative of a stable posture, even if the requirements of the M-of-N filter have been met in step 400. That is, while relative stability may have been detected early in the window, the possible on-set of a posture shift negates that early stability.

To detect a possible onset of a posture shift, step 404 determines whether the second-to-last of the N samples currently being considered, or sample $V_{pt(t-1)}$, is within the stability threshold distance of the preceding sample $V_{pt(t-2)}$. If so, the sample $V_{pt(t-1)}$ is not considered to be indicative of a late-breaking posture shift. Therefore, processing may proceed to step 410. There, $V_{pt}$ is considered stable, and an updated value is obtained for $V_{stable}$.

The updated value for $V_{stable}$ may be obtained, for instance, by averaging the current sample, $V_{pt(t)}$, and the existing value of $V_{stable}$. Alternatively, averaging may be performed for one or more selected samples included within the current N samples, or for one or more samples within the stability window as a whole. As yet another possibility, a median value may be obtained from one or more of the current N samples or one or more samples within the stability window as a whole. If desired, an adaptive algorithm such as described above in regards to Equation 1 may be used to acquire a value for $V_{stable}$. Processing is then considered complete (412), with the stable value for the posture vector being represented by $V_{stable}$.

Returning to step 404 of FIG. 18, if the stability check for sample $V_{pt(t-1)}$ fails because $V_{pt(t-2)}$ and $V_{pt(t-1)}$ are separated by more than the stability threshold distance, another check is made in step 406 to determine whether the detected change in $V_{pt(t-1)}$ is likely the result of a true posture shift, or instead may be attributable to an anomaly, such as noise within the system. This can be determined by considering the vector for the most-recent of the N samples, $V_{pt(t)}$. If $V_{pt(t)}$ is close to $V_{pt(t-1)}$, it is likely that the vector $V_{pt(t-1)}$ is not an anomaly and a bona fide posture shift may be underway, as indicated by the most recent of the N samples. On the other hand, if $V_{pt(t)}$ is relatively close to the other samples in the current stability window while being relatively far away from $V_{pt(t-1)}$, as may be reflected by comparing $V_{pt(t)}$ to the value of $V_{stable}$, it is likely $V_{pt(t-1)}$ is not indicative of a true posture shift but the result of noise or some other transient condition.

In accordance with the foregoing, if sample $V_{pt(t)}$ is within a predetermined "same posture" stability distance from $V_{stable}$ (406), it is likely the large distance between vectors $V_{pt(t-1)}$ and $V_{pt(t-2)}$ detected in step 404 is likely an anomaly such as noise, since $V_{pt(t)}$ indicates a return to the previously-established posture trend. Therefore, the posture vector may be considered stable despite the divergence of $V_{pt(t-1)}$. Processing therefore proceeds to step 410 where the vector is considered stable. A new value for $V_{stable}$ is determined in this step and processing is complete (412).

Returning to step 406, if the current sample of $V_{pt(t)}$ is not within a "same posture" stability distance of $V_{stable}$, $V_{pt(t)}$ may be indicative of an actual developing posture shift. Therefore, processing proceeds to step 408, where it may be desirable to discard all of the samples collected within the stability window, since such samples may reflect a completely different posture than that to which the patient is transitioning. Retaining such samples for use in the next stability window would therefore potentially hamper detection of any newly-developing trend. Alternatively, just the last two samples may be retained for inclusion in the next stability window. As discussed above, many options are possible.

Next, the value for $V_{stable}$ may be re-calculated (409). This may involve determining a new value from just the previous two samples $V_{pt(t-1)}$ and $V_{pt(t)}$, since these two samples likely involve the onset of a new posture. Alternatively, $V_{stable}$ may take the value of just one of these last two sample points, such as the earliest saved sample point (in this case, $V_{pt(t-1)}$). Either embodiment will allow a more accurate value for $V_{stable}$ to be developed more quickly during the next stability window. Processing then proceeds to step 412, wherein the stability determination is considered complete, with the patient's current posture state being considered in transition, such that samples will continue to be collected to locate a stable posture.

The above discussion concerning steps 404 and 406 may be considered further in reference to the vector samples collected during stability window 352 of FIG. 16. Assume the most-recent sample, or sample $V_{pt(t)}$, is sample 14. Therefore, sample 13 is sample $V_{pt(t-1)}$. A relatively large distance exists between samples 12 and 13. This relatively large distance will be detected by the stability check of step 404. In such a case, at least two scenarios may exist: sample 13 may be just an anomaly, such as the result of noise, in which case it is likely that the next sample 14 will return to a value that is much more aligned with the previous samples 10-12. Alternatively, sample 13 may be the result of a bona fide posture change which is occurring late in the stability window, in which case $V_{pt(t)}$ will likely be closer to $V_{pt(t-1)}$ than it will be to the other previous vectors collected earlier in the stability window, as is reflected by the value of $V_{stable}$. Comparing $V_{pt(t)}$ to the value of $V_{stable}$, as occurs in step 406, will distinguish between these two scenarios. In the case exemplified in FIG. 16, it appears that a true posture shift may indeed be occurring since sample 14 is relatively close to sample 13, as indicated by the fact that distance point 358 is below the stability threshold distance. In this case, it may be desirable to indicate postural instability, since a posture shift may be underway. This example highlights the benefit of coupling the checks of steps 404 and 406 of FIG. 18 with use of the M-of-N filter, since the M-of-N filter alone may not detect the onset of a posture shift.

The foregoing describes detecting a posture shift by determining that a single sample $V_{pt(t-1)}$ exceeds a stability threshold and a subsequent sample $V_{pt}$ is not within a predetermined distance of $V_{stable}$. This is just one example embodiment of posture shift detection. In another embodiment, posture shift detection may additionally or alternatively detect multiple sequential samples that exceed a stability threshold. For instance, if it is determined that $V_{pt(t-1)}$ exceeds the stability threshold, and if it is further determined that $V_{pt}$ also exceeds this threshold, a search may be initiated for the next sample that does not exceed the stability threshold. The next such sample that does not exceed the stability threshold may then be compared to $V_{stable}$ to determine whether a posture shift is occurring. In this manner, multiple samples that exceed the stability threshold may be encountered during posture shift detection, with the determination as to whether these samples represent noise or a posture shift being made based on the value of the first encountered sample that does not exceed the stability threshold.

To summarize, the process of FIG. 18 couples an overall stability requirement involving the M-of-N filter with a posture-shift detector. If either overall instability or onset of a posture shift is detected, instability will be determined. This improves system performance over what would be achieved by using the M-of-N filter alone, since the M-of-N filter will not necessarily identify an impending posture shift that involves only the last few samples within a stability window that is about to expire.

The foregoing provides an example of criteria that may be employed to detect posture state stability. Other criteria may be selected instead of, or in addition to, the use of an M-of-N filter and detection of onset of posture shift. As an example, a predetermined number S of sequential samples may be required to be within a predetermined distance of a preceding sample. Alternatively or additionally, the criteria may comprise a requirement that a predetermined percentage of the samples within a stability window falls within some predetermined distance of a median sample value, wherein the median sample value is obtained, for instance, by averaging the x-, y-, and z-axis components of each vector sample in the stability window. As yet another example, determination of onset of a posture shift may focus on the samples occurring within a starting or middle portion of the stability window, rather than the latter portion, as described above. Thus, many different combinations and permutations of stability criteria may be employed according to the current disclosure, and the methods set forth herein are only to be considered illustrative.

Returning to step 400, if M-of-N samples are not within a stability threshold distance of a preceding sample, processing continues to step 402. There, it may be determined which samples to retain for use in the next stability window. As discussed above in regards to FIG. 16, it may be desirable to retain some of the previously-considered samples for consideration in the next stability window. For example, this may be advantageous if the M-of-N stability check failed because of instability early in the window, but a trend is never-the-less beginning to be established later in the window. By saving the samples that are contributing to this developing trend, stability can be detected more quickly during the next stability window.

To further the foregoing objective, it may be desirable to retain for use in the next stability window the maximum number of most-recent samples that will result in only N-M samples failing to meet the stability threshold distance requirements, as well as any intervening or directly-preceding samples that do meet this requirement (402). For instance, consider the example of FIG. 16 that employs a filter having M and N set to "three" and "four" respectively. Imposing the foregoing rule on the system of FIG. 16, one sample (that is 4-3 samples) that does not meet the stability threshold distance will be retained for inclusion in a next stability window. Moreover, any intervening or directly-preceding samples that do meet the stability requirement are also retained. For instance, in this type of embodiment, stability window 336 will be restarted to include not only sample 4 represented by point 332, which fails the requirement, but also sample 3 represented by point 330, since this sample directly precedes sample 4 and does satisfy the stability requirements.

Of course, many different variations are possible when considering which samples to include within a next stability window. In the example specifically shown in FIG. 16, N-M vector samples that did not meet the stability threshold distance were included in the next stability window. However, the next stability window does not include those samples that did meet the requirements and that directly preceded the last failing sample. Thus, for instance, stability window 336 included failing sample 4 but did not include passing sample 3.

As yet another variation, the next stability window may include a predetermined number of the most-recent samples, or a predetermined number of samples selected in some other way. If desired, none of the samples need be retained for consideration in the next stability window, which may contain only samples that were not heretofore processed.

After samples are selected for inclusion in the next stability window (402), processing is complete (412) with $V_{pt}$ being considered unstable. Recall that this will result in the stability window being restarted so that stability processing is re-initiated, as indicated by arrow 383 of FIG. 17 which returns processing to step 372.

As is apparent from the foregoing, the processing performed because of instability detected in step 400 may be different from that performed when instability involves a potential late-breaking posture shift in step 404. In the former instance, it may be desirable to consider some of the previously-processed samples in the next stability window. In the latter instance involving an impending posture shift, it may be desirable to discard all of the samples collected within the stability window as discussed above in reference to step 408. This is true because in the latter instance, the samples that were previously considered may reflect a completely different posture than that to which the patient is transitioning.

As previously discussed, the specific process described in FIG. 18 may be employed to detect an overall stability in the patient's posture through use of a filter such as an M-of-N filter. Late-breaking posture changes may be distinguished from noise by comparing vector samples that are collected later within the stability window to each other and to $V_{stable}$, which is a vector value that represents all, or selected ones of, the vector samples collected during the stability window. In one embodiment, $V_{stable}$ is a running average that is updated as each sample is collected that satisfies the M-of-N filter requirements and the stability check for $V_{pt(t-1)}$, as is shown in FIG. 18.

Those skilled in the art will recognize that many variations of the methods shown in FIGS. 17 and 18 are possible within the scope of the present invention. For instance, the thresholds used within steps 400, 404, and 406 of FIG. 18 may all be the same threshold, or one or more may be different from one another. One or more of these thresholds may be selectable. As another example, if desired, one or more other stability requirements may be utilized instead of, or in addition to, those shown in FIG. 18, as previously described.

Next, a discussion of updating the library to include a newly-detected stable vector value is provided. Recall that the stable vector for $V_{pt}$ that is determined by stability processing, if any, will be reflected by the value of $V_{stable}$, which is derived in any of the ways discussed above in regards to FIGS. 16-18. This value may be stored within the library, either by creating a new library entry for this vector, or by instead updating an existing library entry to include this vector. The process of updating the library is reflected by step 308 of FIG. 15, and is described in more detail in the flow diagram of FIG. 19.

Figure 19:
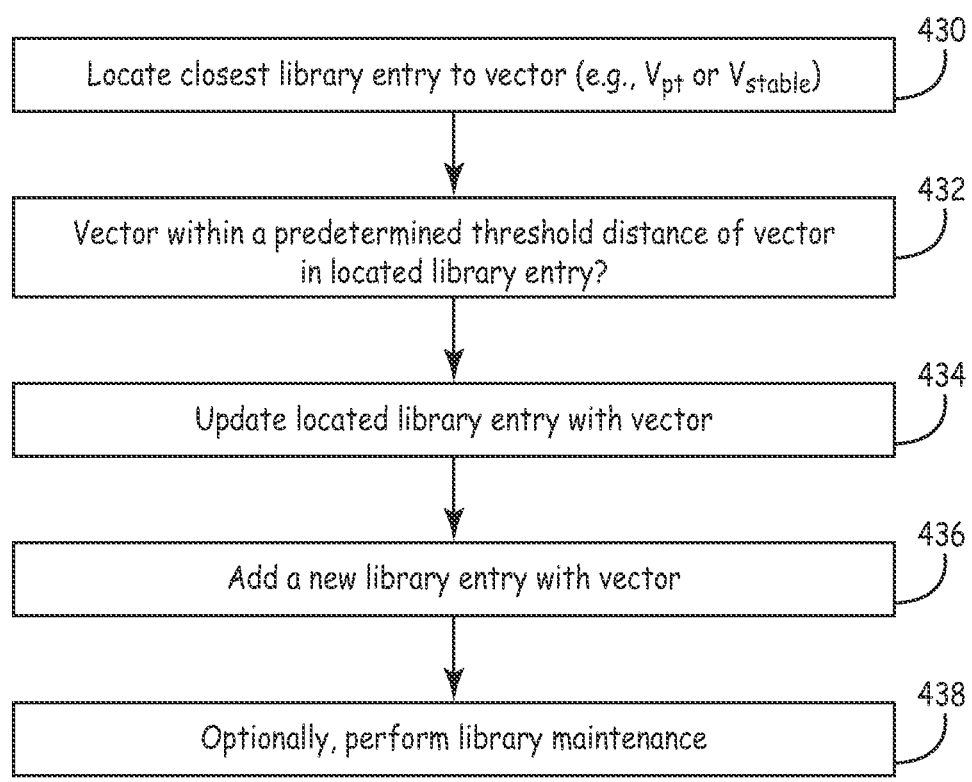
FIG. 19 is flow diagram of one method of updating a library to include a posture state vector.

FIG. 19 commences by locating the entry within the library that stores the vector which is closest to the value obtained for $V_{stable}$ (430). This determination may be made using any distance measurement known in the art, including those mentioned above. In particular, an angle, a Euclidean distance, a straight-line distance, a city-block distance, a Minkowski distance, a trigonometric function, or some other measure of the separation between $V_{stable}$ and the vector of the library entries may be used to make this identification. If desired, the value for most recent-sample of $V_{pt}$ or some other sample could be used instead of $V_{stable}$ to make this identification.

Once the library entry storing the closest vector has been identified, it is determined whether the vector under consideration (e.g., $V_{pt}$ or $V_{stable}$) is within a distance of the located vector that does not exceed a predetermined threshold distance (432). This threshold distance, which may the "same posture" threshold distance employed in step 406 of FIG. 18 or may be some other threshold value. This value may be programmable, and may be selected based on the desired size of the library and the availability of storage space, with the threshold being inversely proportional to the number of allowed entries in the library. For instance, if the posture threshold distance is selected to be relatively small, the library may grow in size to be quite large, which may not be desirable if there are limited storage resources in the system.

If the vector under consideration is within the posture threshold distance of the closest vector within the library, that closest library entry is updated with the value of the vector (434). In one case, this involves merely overwriting the previously-stored vector. In another embodiment, this may involve storing the current vector along with some predetermined number of previous vectors stored for this entry. This latter embodiment may be useful, for instance, if a vector history is being retained for analyzing system performance. Alternatively, an adaptive mechanism such as shown in regards to Equation 1 above may be used to combine the value of the current vector (e.g., $V_{pt}$ or $V_{stable}$) with the value previously stored within the library entry. According to this latter approach, the new posture state that will be represented by the updated library entry is a blending of both the most-recently detected posture state and the posture state previously represented by that library entry.

Returning to step 432, if the current vector is not within the posture threshold distance of the closest vector within the library, a new library entry is created to store this vector (436). Optionally, library maintenance may be performed (438) to determine whether creation of the new library causes the library to grow to a size that exceeds a maximum allowable library size. If such a library size threshold is exceeded, a purge function may be initiated to eliminate one or more library entries, such as those entries that haven't been used to deliver therapy within a predetermined recent time period. Again, such size limits and time periods may be programmably selected in one embodiment to allow the library size to be dynamically adjusted as system resources and/or demands on those resources change.

Thus, FIG. 19 provides a mechanism wherein processor 34 and/or a processor of a programmer are adapted to receive from sensor 40 a signal indicative of a detected posture state of the patient. The processor is adapted to determine whether the detected posture state is represented by one of the stored associations contained within the library. This may involve determining whether the detected posture state is within a threshold distance of a posture state represented by one of the associations (e.g., as by determining a distance between a detected vector and a vector of the association.) If the detected posture state is represented by one of the stored associations, the processor may update the one of the stored associations based on the detected posture state. This may involve updating a library entry based on a vector that represents the detected posture state, as shown in step 434. If such an association does not already exist, however, a new association between the detected posture state and a corresponding therapy parameter value may be created, as shown in step 436.

It will be appreciated that the method of FIG. 19 may, but need not, be practiced with stability processing. If stability processing is used, a value for $V_{stable}$ will be available, as shown in step 304 of FIG. 15. If stability processing is not used, as may arise because of a trigger event such as timer expiration wherein stability processing may not be necessary or desired, the value $V_{pt}$ may be used instead of $V_{stable}$ to update the library, as previously described.

It will be recognized that many alternative embodiments exist to determine whether to update a library entry according to the current disclosure. As one example, the library may track, for each entry, when that entry was last used to control therapy delivery for the patient. Based on this information, it may be determined whether a library entry that is closest to a patient's current posture state was used relatively recently (e.g., within some predetermined time period) to control therapy delivery. If so, it may be desirable to only replace that entry if the new vector is within a second threshold distance that is smaller than the threshold distance that would otherwise be used to make this determination. That is, since the located entry may be a frequently-used entry, it may be desirable to overwrite this entry with new data only if the new vector is "very close" to the located vector, as determined by a small threshold distance. If the new vector is not determined to be "very close" to the existing vector, the new vector may be used to create an additional entry. Such operation may result in the formation of a "cluster" of related entries in areas of three dimensional space that are frequently occupied by the patient, possibly leading to better titration of therapy when a patient is occupying, or close to occupying, a favorite frequently-occupied posture state.

As another alternative embodiment, the time of day or day of the week may be used to select the threshold distance employed to determine whether to update an existing library entry or create a new entry. For instance, it may be known that when the patient is at work, the patient enters multiple related posture states that although similar, could beneficially be associated with different therapy parameters. Thus, during times and/or days when the patient is at work, it may be desirable to utilize a smaller threshold distance to determine when a new library entry will be created. This may result in generation of multiple closely-spaced library entries which can beneficially be used to deliver more finely-titrated therapy to the patient while the patient is working. A larger threshold distance may be used at times/day when the patient is not working so that library space is not unnecessarily utilized to store additional entries associated with the patient's leisure activities.

Other physiological signals indicative of status of the patient may be used to select a threshold distance, if desired. For instance, signals indicative of a patient's heart rate, EEG, ECG, respiration rate, an activity level of the patient, a chemical aspect of the patient's blood, and/or any other aspect of the patient's physical condition may be employed alone, or in conjunction with one or more other signals, to select a threshold distance for use in determining whether a new library entry will be created. As one example, it may be desirable to allow more closely-spaced library entries to be created when the patient is known to be exercising, as indicating by elevated heart rate, respiration rate, and/or activity level. This may optimize therapy delivery during exercise when the patient may be entering a large number of distinct yet related posture states that should each be associated with different therapy parameters.

Other system-related aspects may affect selection of threshold distance in addition to, or instead of, physiological parameters such as those set forth above. For instance, in embodiments wherein the size of the library is user selectable, the library size will be inversely proportional to the threshold distance. A smaller library may be used with a larger threshold distance so that fewer library entries will be created for a given set of detected vectors.

Battery characteristics may likewise affect this determination. For instance, if the implantable device includes a prime cell battery that is nearing the end of its useful life, it may be desirable to increase the threshold distance so that fewer library entries are maintained, reducing the amount of energy consumed for maintaining the library, searching library entries, and so on.

Similarly, detection of any of the foregoing conditions, including system status, patient physiologic signals, and/or user-provided signals may be employed to enter a mode wherein newly-acquired vectors are always used to update existing library entries such that no new library entries are created. This may be useful when the library is determined to be full.

Conversely, any of the aforementioned conditions may be used alone or in conjunction with one another to cause the system to enter a mode wherein all newly-received vectors result in creation of a new library entry. For instance, the time of day and/or day of week may be used to trigger a mode wherein all newly-acquired vectors are used to create new entries.

As another example, in a system that utilizes device flip-detection to determine when an implantable device has potentially become repositioned, or "flipped", within the surgical pocket, an indication that a device flip has likely occurred may prompt all newly-received vectors to result in creation of new entries. This will allow the library to be re-populated as quickly as possible with vectors that correspond to the device's new orientation. Such detection may even result in marking all entries that were created prior to flip detection as obsolete so that those entries will not be used for therapy delivery, since they do not correspond to current device orientation.

In the foregoing manner, a library is automatically populated to include new vectors that represent positions the patient is assuming over time. These vectors need not be associated with any predetermined posture states, but can be any position that the patient is assuming that meets the selectable requirements of stability discussed above. In one embodiment, this mechanism may be used to populate only a portion of posture space (e.g., hysteresis space). In another embodiment, the entire three-dimensional posture space may be populated in this manner if desired. This will be described further below.

Next, a mechanism for determining which parameters should be associated with the new/updated library entry is provided. This type of processing occurs in step 310 of FIG. 15 and is described in more detail in FIG. 20.

Figure 20:
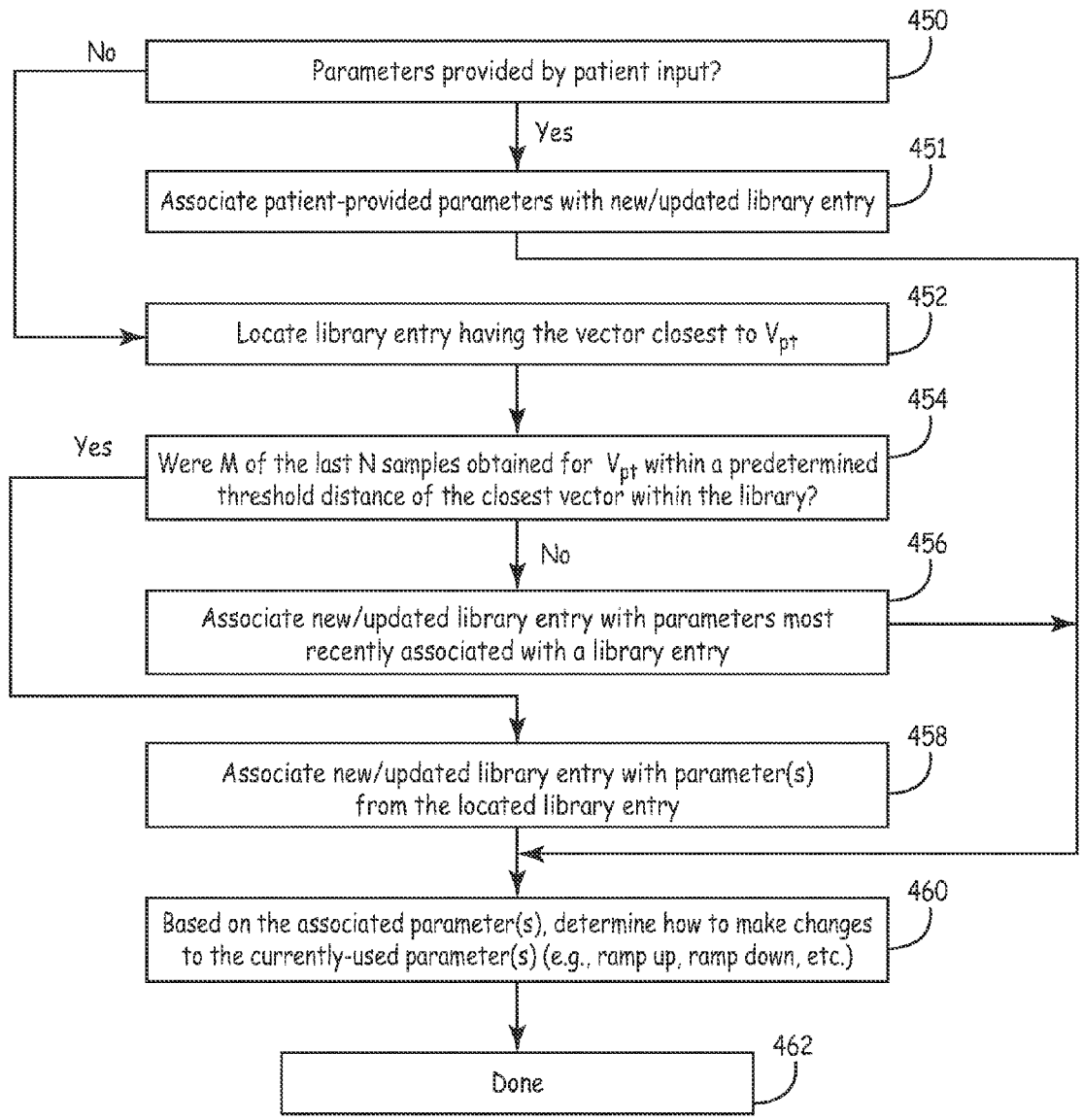
FIG. 20 is a flow diagram illustrating one method for determining parameters to associate with a posture state vector value.

FIG. 20 is a flow diagram illustrating one method for determining parameters to associate with a vector value that is entered into the library according to any of the above-described mechanisms. Such a method may be performed to associate therapy parameters (e.g., stimulation parameters, drug delivery parameters, etc.) with a vector. However the disclosure is not so limited. Any operational parameters that may be usefully controlled by association with a posture state may be identified and stored within the library in addition to, or instead of, therapy parameters.

According to the method of FIG. 20, if a trigger event that prompted capturing of the vector involved patient input (450), the parameter values specified by the patient are associated with the new/updated library entry storing the current vector (451). However, if there were no parameters provided via patient input, as may be the case if the trigger event involved expiration of a time period, some other mechanism is needed to identify the associated parameters. In this type of scenario, the library entry that stores the vector that is closest to the current vector (that is, the "closest" library entry) is identified (452).

Next, it is determined whether M of the last N obtained vector samples are within a predetermined threshold distance of the vector in this closest library entry (454). The values selected for "M", "N", and the threshold distance may, but need not, have any relationship to values used during stability processing. As was the case described above, values for "M", "N", and the threshold distance may be programmable using any of the mechanisms heretofore described.

As may be appreciated, the determination of step 454 requires a buffer or some other storage facility be maintained to store at least N of the last vector samples for the patient's posture. Such vector samples may be available already if stability processing was performed. However, if stability processing was not performed (e.g., stability processing was by-passed), such samples will never-the-less need to be retained for parameter identification according to step 454.

If M of the last N vector samples were not within the predetermined threshold distance of the vector within the closest library entry, the same parameters most-recently associated with a library entry are associated with the new/updated library entry (456). In this case, because the current vector has not presented a stable value that is close to any other existing library entry, it is better to use a temporal relationship to determine the associated parameters that will be associated with the newly-created/updated library entry. In an alternative embodiment, the parameters last used to deliver therapy to the patient could be associated with this library entry.

On the other hand, if M of the last N vector samples were within the predetermined threshold distance of the closest library vector, the parameters from the located library entry are associated with new/updated library entry (458). This association is made in this instance since the current vector is thought to be sufficiently similar to the vector of the located entry to warrant associating the same parameters to the new/updated library entry.

In one embodiment, not only are the parameters obtained from the closest library entry associated with the new/updated library entry, but they may also be used to control current operation of the IMD 12. Since these parameters are not necessarily the same parameters that are currently being used to deliver therapy to the patient, a modification to therapy delivery may result. To prevent this change from causing discomfort to the patient, it may be desirable to identify the type of change that will occur (e.g., an increase or decrease in the parameter value) and then select a change-control parameter to control how the change will be made (460). Such a change parameter may include a ramp-up or ramp-down parameter that controls a rate at which change of a therapy parameter will be performed. In one embodiment, the value of this parameter may be determined by comparing a current parameter value to the new target parameter value to determine a net difference between the two. If this difference is to be spanned within a number of incremental adjustments, it may be determined how much change is to be made with each adjustment. In another embodiment, the rate of ramp-up or ramp-down may be clinician-, patient-, and/or manufacturer-selected.

In one embodiment, vectors obtained using the mechanisms shown in FIGS. 15-21 may be assigned names by a user such that these vectors become part of the named posture set supported by the system. For instance, when a trigger event occurs, such as receipt of patient input, it may be determined if the detected posture vector will result in creation of a new library entry. If so, the user may be prompted to provide a designation for the vector, which may be some name the patient associates with the corresponding posture state. Such a name may be provided via any of the user input mechanisms supported by the system, including a touch-sensitive input capability, a key pad, a speech-recognition mechanism or other sound-recognition capability, or any other input mechanism that may be used for this purpose. The assigned name may be indicative of a type of activity (e.g., Swimming, Running, Biking etc.) described by both an activity component and a vector, or may be solely related to a posture described by a vector without reference to an activity component (Leaning Forward, etc.). If desired, in one embodiment, the user may decline to name a posture state, or may disable this feature entirely so that the user is not prompted for a designation.

In another embodiment, it is the user that actively determines when to name a posture state by making a designation contemporaneously with the trigger event, such as by selecting a feature on a drop down menu at the time a new therapy parameter is provided. This will cause the system to prompt the user for the posture state designation in any of the aforementioned ways. In this embodiment, the user is not burdened unnecessarily with automatically-generated prompts to enter a user name, but rather dictates when such information will be solicited.

In the foregoing manner, the set of named posture states that is recognized by the system may initially be populated with a limited predetermined posture state set that is available during an initial calibration procedure, such as described above. Thereafter, this initial posture state set may grow as the patient chooses to name additional postures states that are assumed as the patient goes about daily life. This named set may thereafter be selected for display on one or more summary posture state screens such as those shown in FIGS. 6A, 6B, 8B, and 8C.

Figure 21:
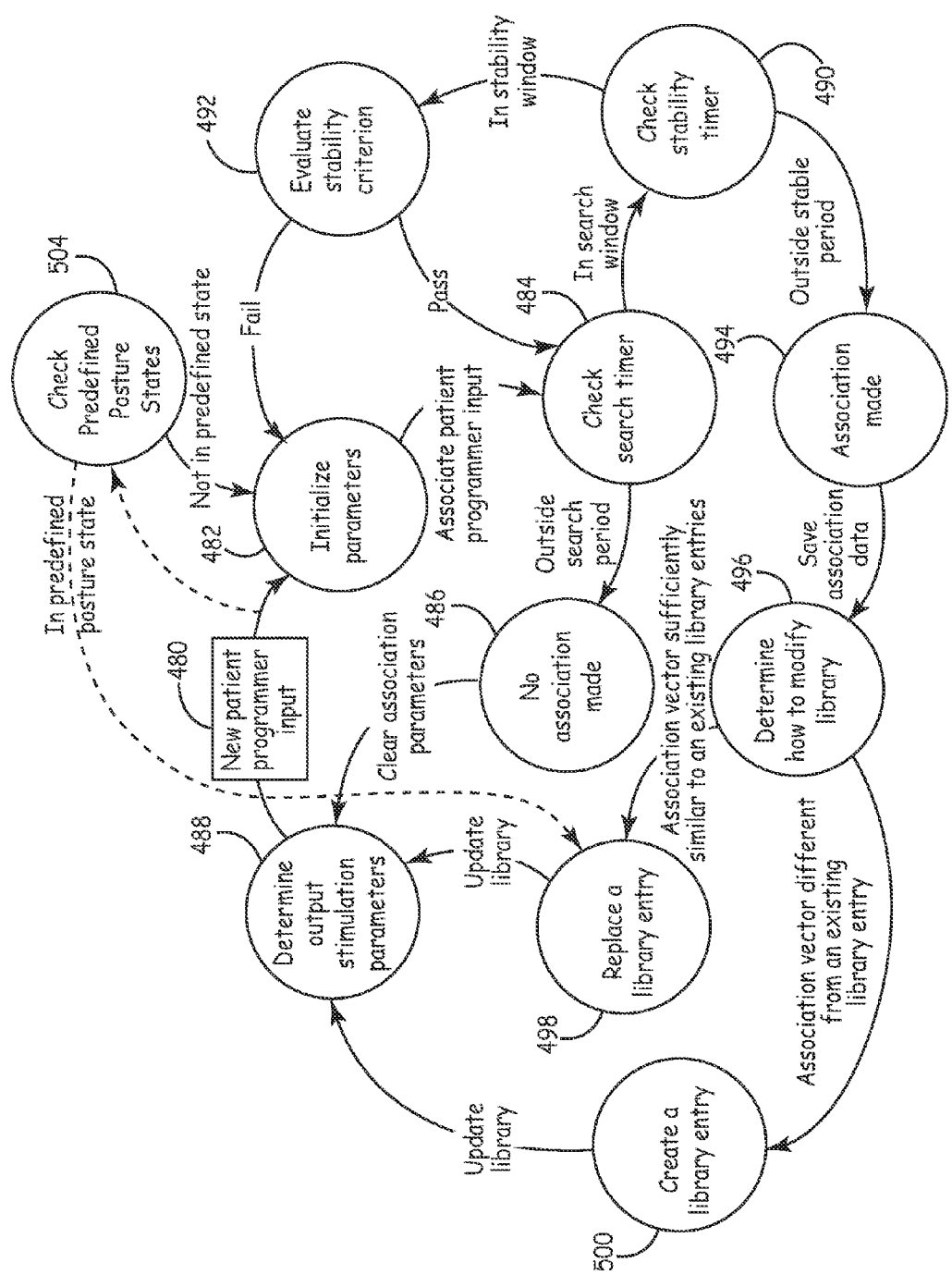
FIG. 21 is a state diagram that illustrates one for adding posture state vectors to a library according to methods discussed above.

FIG. 21 provides a state diagram that illustrates one embodiment of a method for adding vectors to a library according to methods discussed above. In block 480, new patient programmer input is provided, as received from a patient programmer. As discussed above, this is one type of trigger event that will prompt stability processing. As such, state 482 is entered to initialize parameters for performing stability processing. Such parameters may include initial values for the search and stability windows, the initial value for $V_{stable}$, and so on. Once these values are initialized, a state 484 for checking a search timer may be entered. Such a timer may be used to determine whether a search window has expired.

If such a timer has expired, no association will be made between the current vector and provided parameters, as indicated by state 486. In this case, state 488 is entered wherein it is determined if/how to modify parameters being used to control IMD 12. This may, for instance, involve modifying current therapy parameters being used to deliver therapy to a patient. As discussed previously, this may involve determining a ramp-up or ramp-down parameter, a time over which the change will occur, and so on. Thus, it is appreciated that even though patient input did not result in creation of a new library entry, it will never-the-less result in current parameters being adjusted to control the therapy. Once in state 488, additional patient programmer input may be received, as indicated by block 480.

Returning to state 484, if the search timer has not expired, a state 490 is entered to check a timer to determine whether a stability window has expired. If not, and the current time is within a currently-running stability window, a transition occurs to a state 492 wherein the stability criterion is evaluated. As previous described, such stability criterion may be programmably selected, and may involve not only an overall stability determination (e.g., use of an M-of-N filter), but also stability criterion to evaluate changes detected later in a stability window (e.g., comparing late-detected vectors to each other and/or to a value representative of all, or at least multiple ones, of the vectors sampled within the current stability period.)

If the stability evaluation fails such that it is likely the vector is not yet stable, a transition occurs to state 482 to re-initialize some, or all, of the parameters used for stability processing. For example, this may involve re-setting or re-acquiring a value for $V_{stable}$, restarting the stability window, disregarding some, or all of the previously collected samples, and so on. Once in state 482, processing may proceed as previously described.

Returning to state 492, if the stability evaluation passes, transition occurs to state 484 to re-check the search timer and continue as described above. Assuming a transition again occurs to state 490 to check the stability timer, and assuming that the stability timer has now expired, state 494 is entered wherein an association is made between the current stable vector and parameters provided by the patient input. State 496 then determines how to modify a library of vectors to include the vector and associated parameters. In particular, if the vector is sufficiently similar to an existing library entry, the vector contained in the existing library entry is replaced with the new vector or a vector derived in some way from the new vector, as is shown in state 498. Associated parameters may also be stored within this entry. However, if the vector is sufficiently different from an existing library entry, a new library entry is created, as represented by state 500. In either case, state 488 is entered wherein it is determined how to modify parameters being used to control IMD 12. This may, for instance, involve modifying current therapy parameters being used to deliver therapy to a patient. As discussed previously, this may involve determining a ramp-up or ramp-down parameter, a time over which the change will occur, and so on.

As discussed above, the mechanism to automatically associate any detected vector with a parameter set, as described in relation to FIGS. 15-21, may be used to populate an entire library. In this case, the library may be considered a set of "areas" (e.g., cones) in three-dimensional space, each having a location determined by a corresponding vector. The size of each such area may be determined, for instance, by the threshold distance used to determine whether to update an existing library entry or create a new library entry for a given vector. For instance, this threshold distance is employed in one embodiment in step 432 of FIG. 19. When this distance is increased, the total number of entries in the library is reduced, as discussed above.

As discussed, the techniques of FIGS. 15-21 may be used to populate just some of three-dimensional posture space, such as hysteresis space. In such an embodiment, when a new vector is acquired, it may be determined whether this vector lies within space already associated with an existing named posture state definition (e.g., a cone associated with Upright, Lying Left, Lying Right, Reclining, etc.). If so, that vector may be processed according to techniques described above in reference to the defined posture states, such as using adaptive mechanisms similar to that exemplified by Equation 1. Otherwise, if the vector lies outside of the predetermined posture state definitions (e.g., in hysteresis space), that vector may be used to create a new library entry or update an existing library entry that is not associated with one of the predefined posture states.

This type of processing is depicted by optional state 504 of FIG. 21 as follows. When patient programmer input is received as indicated by block 480, processing may transition to state 504, where it is determined whether the vector lies within an area that has been allocated to a predetermined posture state definition. If not, a transition to state 482 occurs so that processing may continue to determine whether the vector should result in a new library entry that is not associated with a predefined posture state. However, if the vector does lie within the area already defined to be included in a predetermined posture state, processing transitions to state 498 wherein the existing library entry for the predetermined posture state may be updated if all filter criteria are met for the newly-receive vector. Processing continues to state 488 where the parameters that are currently in use may be adjusted, and the process may then be repeated.

It may be appreciated that in an embodiment that includes processing for predefined posture states, such as shown by optional state 504 of FIG. 21, the predefined posture states (e.g., the posture state for Upright) will continue to be adjusted based on receipt of new vector samples. This may result in migration of the area associated with the predetermined posture states into a region populated by vectors that are not associated with any of the predefined posture states. For example, because of adaption of the Upright posture vector, the cone associated with the Upright posture state may migrate into an area that overlaps with vectors stored in other library entries. In this case, some mechanism may be employed to determine which library entry is to control operation within the overlapping region in space. For instance, it may be desirable to allow the predetermined posture states to take precedence. Alternatively, the library entries associated with vectors that were not predefined may take precedence when a conflict occurs. In one instance, the entry having the "safest" parameter values (e.g., lower amplitude stimulation values, smallest drug bolus values, etc.) may take precedence. Many other mechanisms exist for determining which entry will govern operation of the IMD 12 in an embodiment wherein two entries may overlap in three-dimensional space.

According to another aspect of the disclosure, once a sufficient number of associations between posture states and corresponding parameters have been created as the patient goes about daily life, processing may be performed to group entries having similar parameter values and locations into posture state regions. In one embodiment, this grouping occurs only for those vectors that are not associated with predetermined posture states. According to this approach, library entries are searched to locate a group of relatively closely-spaced vectors that have therapy parameter values (e.g., stimulation amplitudes) that are within some predetermined threshold of one another. That is, library entries are identified that are similar both spatially and based on the associated therapy parameters. The spatial region represented by the library entries is considered a posture state region that may be handled in a uniform manner for purposes of controlling therapy.

According to one method, when a patient assumes a pose that is classified within an existing posture state region (e.g., the detected posture vector lies within the region), therapy may be delivered according to one or more parameter values that have been associated with the posture state region. Grouping the library entries into posture state regions may substantially reduce the processing that is required to provide posture-responsive therapy. For instance, instead of searching through many individual library entries to determine which library entry best represents a patient's posture state, the search may instead compare a patient's current posture state to a more limited set of posture state regions to determine the appropriate therapy. This may save a significant amount of processing time, and may further conserve power, extending battery life of an implanted device.

Creating the posture state regions may be accomplished using a number of available clustering techniques known in the art, including hierarchical (e.g., agglomerative) clustering, partitional clustering (e.g., K-means, locality-sensitive), spectral clustering, and other techniques familiar to those skilled in the art. Neural networks (e.g. Kohonen self-organized networks) may be used to facilitate clustering in one embodiment.

Clustering may be performed in batch mode, meaning all data points (e.g., library entries) are processed together to produce a set of clusters. Alternatively, a more sequential approach may be taken wherein some library entries may be processed to form one or more clusters at one point in time and later additional processing may be performed to create additional clusters. The processing to perform the clusters may be performed by IMD 12, or some or all of the processing may be performed by an external device such as programmer 20 or some other external device (e.g., one or more data processing systems) after the library entries have been uploaded to the external device via telemetry communication, for example. If external processing is utilized, the resulting clusters may be downloaded to IMD 12 for use in classifying a patient's posture state.

After posture state regions are created using clustering techniques, the posture state regions may be represented as additional entries within the library, or they may be stored within another data structure. In either case, the clusters may be used to classify a patient's posture state in a more efficient manner than if all of the individual library entries are used for this purpose.

The following discussion provides a simplistic conceptual view of some example steps which may be used to perform clustering for the library entries. The way such steps are implemented will depend on the clustering technique(s) that are selected for use, whether sequential versus batch mode processing is used, and so on.

Library entries may be grouped into posture state regions in a number of different ways. In one embodiment, processing may commence by randomly selecting a library entry. A search may be performed to identify other library entries having vectors that are within some predetermined distance of the vector within the selected entry. This distance determination may be made using angles, trigonometric functions, and/or using any other type of functions, as discussed above. For the identified library entries, it may then be determined which entries are associated with therapy parameter value(s) that are similar to those associated with the initially-selected library entry. The newly-identified library entries that are both spatially similar to the selected entry and that have similar parameter values are retained and processed in a manner similar to that performed for the initially-selected entry. That is, for each additionally-identified library entry, a search is performed to identify further library entries that have not yet been identified, that are spatially similar and that have similar parameter values. Processing may continue until no further library entries meeting the requirements can be identified.

While the foregoing example describes the determination of spatial similarity and parameter similarity as being performed in two discrete steps, these determinations may be collapsed into a single step in one embodiment. In this case, each data item associated with a library entry (e.g., a posture state vector and one or more therapy parameter values) may be normalized and represented as a single unitless value. This process may be accomplished using various normalization techniques known in the art. These unitless values may be used to group library entries in an optimal way according to a selected optimization technique.

In this manner, an "area" in three-dimensional space represented by multiple similar library entries may be automatically identified as a posture state region. In one embodiment, a posture state region includes only dynamically-created posture states as described in reference to FIGS. 15-20 above, to the exclusion of regions associated with the predetermined posture state definitions. In another embodiment, the predefined named posture states may also be considered when deriving the posture state regions. That is, in an alternative embodiment, the posture state regions may group together not only similar ones of the dynamically-created posture state/ parameter associations but also any similar one of the predetermined posture state definitions.

When library entries are grouped into posture state regions using mechanisms similar to those described above or any other mechanism known in the art for this purpose, two aspects associated with the region must be determined. A spatial description of the region must be derived and the therapy parameters to be associated with that region must be determined A spatial description of the posture state region may be automatically derived using clustering techniques, including but not limited to those set forth herein. As one very simplistic example technique, the spatial description is derived by first approximating a central vector to represent the other vectors in the group. The x-, y-, and z-axis components of the central vector may be derived as some function of the respective x-, y-, and z-axis components of each constituent vector contained within the posture state region, for instance. The central vector may be obtained as an average, weighted average, median, or based on some other function of the vectors that are contained in the group.

Next, a description of a geographic region in space relative to this central vector is derived, wherein that geographic region approximates the posture state region. As a most simple example, a description of a cone may be derived that has as its central axis the central vector (i.e., the cone is symmetrically-disposed about the central vector.) The angle between the central axis and the edge of the cone may be determined, for example, by identifying the vectors at the "edges" of the posture state region, determining a distance between the edge vectors and the central vector (e.g., using a cosine, a sine, an angle, a straight-line distance, etc.) and then selecting the cone angle as some function of the determined distances.

Various optimization techniques may be utilized to obtain the cone angle. For instance, the angle may be selected such that all of the edge vectors that reside at the edge of the posture state region will be within the cone. In one embodiment, optimization is performed to maximize the number of edge vectors included within the cone while minimizing the area contained within the cone that is not part of the original posture state region. Many approximation techniques are possible.

In one embodiment, if the cone approximation technique described in the foregoing paragraph "fails" such that any cone that may be derived will contain more than some predetermined amount of space that was not within the original posture state region, then it may be determined that a single cone is not a good approximation of the original posture state region. In this case, the posture state region may be divided into sub-regions. That is, processing may be performed to identify sub-regions of space within the original posture state region that are heavily populated with library entries. In a manner similar to that described above, a central vector is determined for each sub-region, and cone-fitting processing is performed to find a cone that approximates the sub-region. As discussed above, this may require identifying a cone that includes at least some predetermined number or percentage of vectors contained within the sub-region, and which also does not contain more than some predetermined amount of space that lies outside of the sub-region. In this manner, one or more vectors and corresponding cones may be derived to approximate the original posture state region.

While the foregoing describes using central vectors and cones to approximate a posture state region, other relationships may be used for this purpose. For instance, a toroid surrounding a vector may be used to approximate a posture state region if that spatial relationship of the library entries warrants use of this type of relationship. Alternatively, logical relationships may be used for this purpose. As an example, a "slice" in three-dimensional space described by the intersection (logical "AND") of two overlapping cones may be used to approximate a posture state region. Many variations are possible. In one embodiment, a limited set of template relationships (e.g., cone, toroid, etc.) are available for selection when automatically deriving descriptions for the posture state regions. The template that best approximates the shape of the region may be selected, and the size of the template is adjusted to match the region.

After a description of a posture state region has been developed, the therapy to be associated with the posture state region may be identified. The therapy parameter(s) for a posture state region may be derived as an average, a median, a weighted average, or using some other function applied to the therapy parameter values of the library entries included in the posture state region. In one embodiment, a weighted average may be used for determining a therapy parameter value to associate with a posture state region. For instance, the library entries that are "centrally located" within a posture state region as compared to the other library entries may be identified using techniques described above. The parameter values associated with these centrally-located entries may be accorded the largest weighting factor. A next-highest weighting may be assigned to a next tier of library entries that border the centrally-located entries, and so on. The library entries located at the "edges" of the posture state region may receive the smallest weighting factor. The assigned weighting factors may then be used to determine therapy parameter values using a weighted average or a similar weighting function.

As stated previously, the specific way in which the posture state region descriptions are obtained, as well as the format and details concerning the description, will depend upon the clustering technique(s) selected for use in processing the library entries. However, the conceptualized view of the process will remain the same: the library entries are groups according to spatial and parameter similarities that are described by the resulting posture region description.

In one embodiment, a user may be allowed to name posture state regions. For instance, a user may choose to enter a mode that displays yet-unnamed posture state regions. Such a display may include for reference purposes one or more vectors associated with previously-named posture states as well as the region in space that is eligible to receive a new name. The user may be prompted to provide the name for the posture state region. Such a name may be provided via any of the user input mechanisms supported by the system, including a touch-sensitive input capability, a key pad, a speech-recognition mechanism or other sound-recognition capability, or any other input mechanism that may be used for this purpose. If desired, in one embodiment, the user may decline to name a posture state region, instead "skipping ahead" to a different posture state region that is to be named.

The descriptions for the posture state regions as well as the associated therapy values may be stored in the library with the other library entries, or may be stored in a separate data structure. If posture state regions are stored within the library, a library entry for a posture state region may replace all of the entries for all of the vectors that are included within the posture state region. In this way, the size of the library can be managed by periodically grouping multiple vectors into posture state regions.

The posture state region descriptions may take precedence when determining the appropriate therapy to be delivered to a patient as the patient assumes a new posture state. That is, when a patient assumes a new posture state, it may be determined whether the patient's detected posture vector lies within one of the posture state regions. If so, therapy may be delivered to the patient according to the parameters associated with that posture state region. Only if the patient's current posture state cannot be classified using this abbreviated search will a complete search of the library of vector/parameter associations be performed to identify therapy parameter values for use in delivering therapy.

In a different embodiment that uses both posture state regions as well as a predetermined set of posture state definitions (e.g., Upright, etc.) to classify the patient's posture state, the patient's posture state may initially be classified using a three-step process. First the predetermined set of posture state definitions may be used to classify the patient's posture state. If no classification results such that the patient's posture state lies outside of all posture state definitions, it may be determined whether the patient's posture state falls within one of the posture state regions. If the posture state likewise falls outside of all posture state regions, a complete search of the library may be performed to identify a vector/parameter association for use in delivering therapy. In this manner, abbreviated searches are used to classify the posture state as efficiently as possible, and a complete search of the library is initiated only if the first two searches fail to make a classification.

In the foregoing manner, the posture state regions (and, if desired, the predefined posture state definitions) may generally be searched more quickly than the entire library. This may allow posture state classification to complete more quickly and with less power expenditure in an embodiment that combines all of these techniques.

After posture state region descriptions are automatically created, trigger events such as patient therapy adjustments or time/day trigger events may continue to cause the capture of additional posture state vectors for the patient. If a newly-captured vector is stable, and if it lies within an existing posture state region, the therapy parameters associated with the vector may be used to update the therapy parameters associated with the posture state region in which the vector lies. Updating of the therapy parameters for an existing posture state region may be accomplished using any of the adaptive or other parameter determination techniques described herein.

If a new stable vector is received that lies outside of the existing posture state regions, it may be determined whether a new entry is to be created or an exiting entry is to be updated within the library for a new posture state as described by the vector. This may be accomplished using techniques similar to those set forth in FIG. 19.

In one embodiment, the posture state regions may be periodically updated to take into account any vectors not yet included within a posture state region. For instance, this may involve creating new posture state regions based on clusters of vector/parameter associations, or expanding the borders of existing posture state regions to include clusters of vector/parameter associations having similar therapy parameters.

In yet another embodiment wherein descriptions of posture state regions are maintained in parallel with vector/parameter associations (i.e., vector/parameter associations are not necessarily deleted from the library when a corresponding posture state region description is created) posture state regions may be re-derived completely "from scratch" periodically based on a then-current set of vector/parameter associations as stored within the library entries. Thus, it may be appreciated that many embodiments are possible within the scope of the current disclosure to create and maintain posture state regions.

Figure 22:
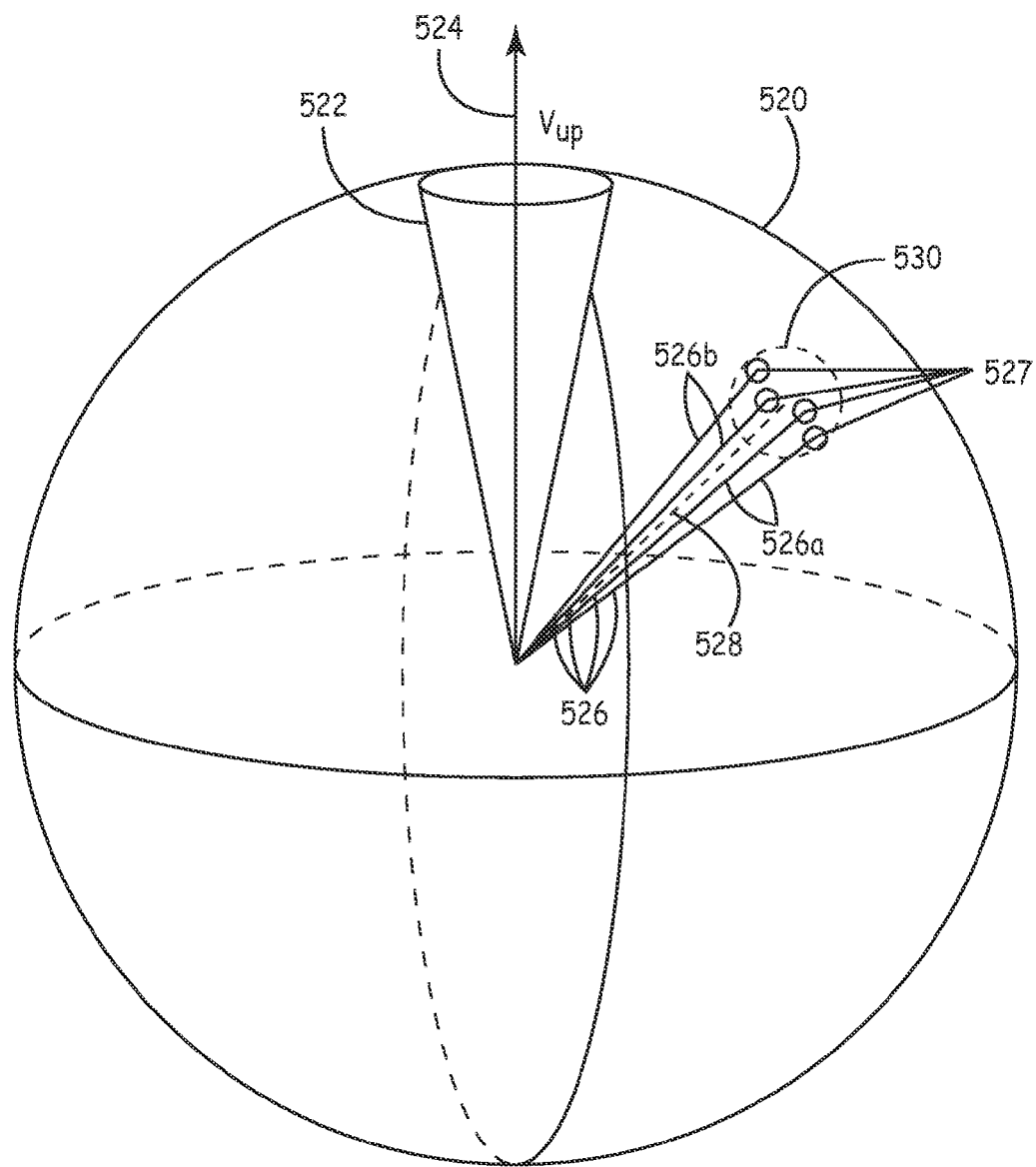
FIG. 22 is a diagram representing the grouping of library entries into posture regions.

FIG. 22 is a diagram representing the grouping of library entries into posture regions. Sphere 520 represents all of three-dimensional posture space. Some or all of this space may be populated with vectors that are not associated with predetermined posture states. In one embodiment, this three-dimensional space may also contain vectors associated with predetermined posture states, such as vector $V_{Up}$ 524 and associated cone 522 used to define the Upright posture state.

In the illustrated example, four additional vectors 526 have been defined in hysteresis space, each of which will be assumed to be associated with a respective library entry. Each of these four vectors may be visualized as a respective cone, each having a cone size that is determined by the threshold distance between two adjacent library entries, as discussed above. In the current case, the size of each cone is represented by the cone bases 527.

Assuming the four library entries associated with vectors 526 meet the selected criteria for spatial similarity as well as parameter-value similarity, these library entries may be used to form a description of a posture region. Cone-fitting or other region-fitting steps may be taken to derive an approximation of a spatial region that most closely "fits" the four cones represented by the cone bases 527. Such region-fitting steps may first derive a central vector 528 (shown dashed), which may be obtained by averaging x-, y-, and z-axis component values of each of the four vectors 526. For instance, the four x-axis components may be averaged, the four y-axis components may be averaged, and the four z-axis components may be averaged to obtain x-, y-, and z-axis components of the central vector 528.

Once central vector 528 is derived, selected rules may be applied to determine how the region will be approximated. For instance, the rules may be used to derive an angle for a cone that approximates the region. As a particular example, a rule may be used to limit the number of vectors that are excluded from the resulting approximation. Another rule may limit the space within the resulting approximation that is outside of any of the four cones 527. In the current example, the resulting approximation is a cone having a base 530 (shown dashed) that includes each of the cones represented by bases 527.

In some cases, it may not be possible to obtain a single approximation for a posture region that satisfies the rules that are in place for obtaining the approximation. In that type of scenario, the posture region represented by bases 527 may be divided into sub-regions. For instance, vectors 526a could be included in a first sub-region and vectors 526b may be included in a second sub-region, and the region-fitting process may be repeated for each of the sub-regions.

Once the approximation 530 for the posture region is derived, one or more therapy parameters may be derived for the resulting posture region or sub-regions. These may be obtained by applying an average, weighted average, median, or other function to the respective values of the library entries in the posture region or sub-regions, as described above.

As previously discussed, in one embodiment, a user interface feature may allow a user to assign a name to a posture state region description. For instance, this feature may provide an illustration of the resulting unnamed posture region description (which may be similar to the display shown in FIG. 22). The display may include at least one vector that is associated with a predetermined posture state, such as vector $V_{Up}$ 524. This will provide the user with a frame of reference for the location of the new posture region description. The user may then specify a name for the posture region description in any of the ways previously described.

Figure 23:
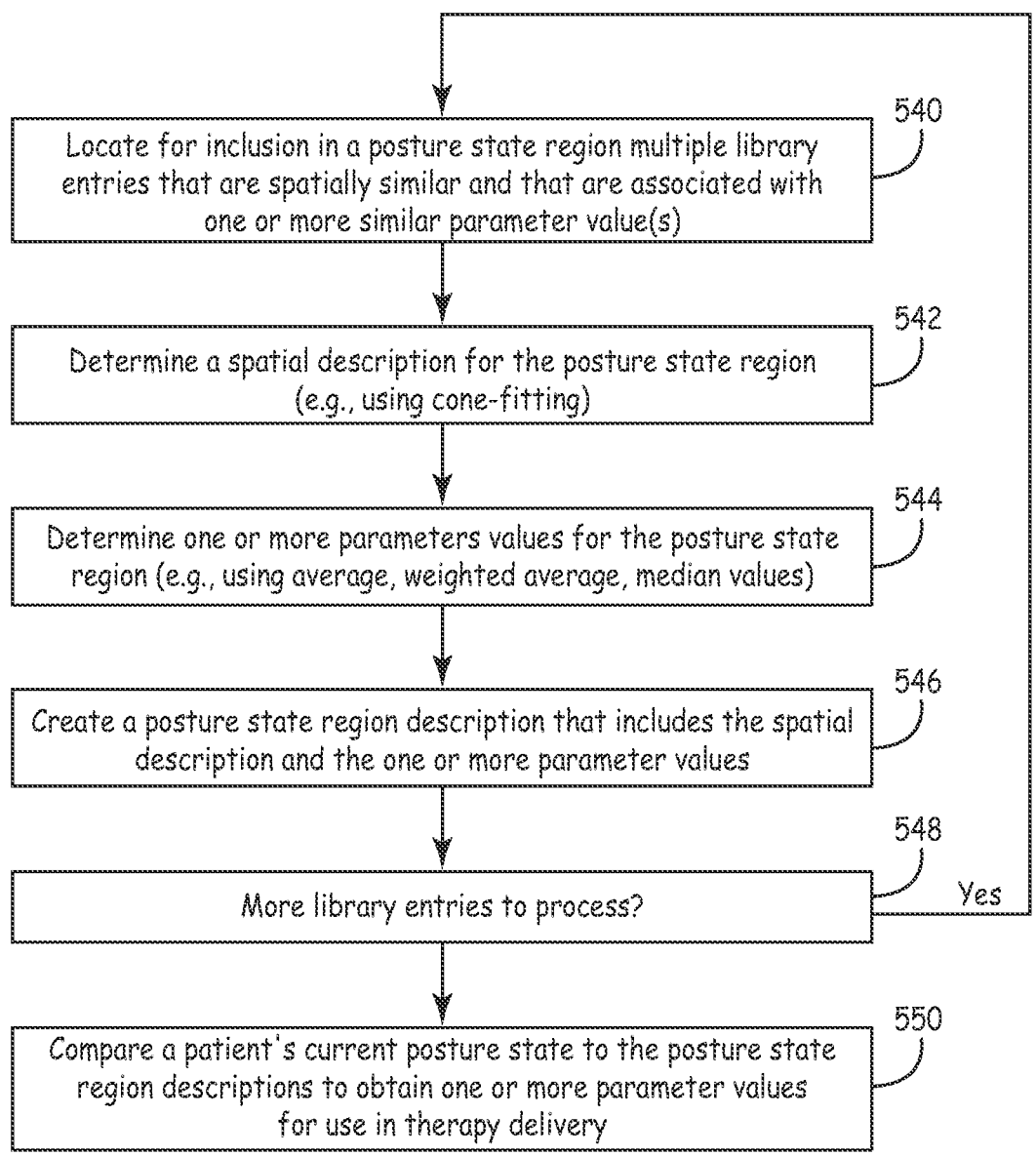
FIG. 23 is a flow diagram summarizing an automated process of creating posture region descriptions.

FIG. 23 is a flow diagram summarizing an automated process of creating posture region descriptions. Such a process may be performed by processor 34 of IMD 12 and/or a processor of programmer 20, for instance.

First, multiple library entries that are spatially similar and that are associated with one or more similar parameter value(s) may be located (540). A spatial description of an approximation of the posture state region may be derived (e.g., using cone-fitting techniques, 542). One or more parameters values may be determined for the posture state region (544). For instance an average, weighted average, median, or some other function may be applied to the parameter values of the library entries in the posture state region to obtain these values. A posture state region description that includes the spatial description and the one or more parameter values may be created (546). The posture region description may be stored within a memory of IMD 12 and/or a memory of an external device such as programmer 20, if desired. If more library entries are to be processed (548), execution returns to step 540 to repeat the steps so that more posture region descriptions may potentially be created. Thereafter, the one or more created posture state region descriptions may be compared to a patient's current posture state to obtain one or more parameter values for use in therapy delivery (550).

As may be appreciated, the process of grouping library entries into posture state regions is, in some ways, analogous to the initial creation of posture state definitions. In the case of posture state definitions, a region in space is being allocated to a same posture state by selecting a vector (e.g., $V_{Up}$ and a tolerance (e.g., a cone, toroid, etc.) This selection will typically be performed during a calibration procedure with an eye towards the future, making assumptions about what posture states the patient will likely occupy. That is, the definitions may be created without the use of data that reflects actual posture states of the patient, particularly when estimated vectors are used for this purpose as discussed above. These definitions may, but need not be, updated later using actual data according to the adaptive techniques described herein.

The creation of posture state regions, like posture state definitions, is seeking to include an area of three-dimensional space into a same posture state classification. However, in this case, the generation of the area description uses actual patient data (e.g., actual vectors and parameter values) obtained during daily life, versus information that may be provided or estimated during a calibration session.

The use of posture state definitions may be selected over posture state regions in a system that does not have processing capabilities, storage space and/or energy resources needed to develop a posture state library and perform the subsequent analysis to group collected vectors into regions. However, use of posture state regions may provide better therapy titration in some cases, since control over the therapy is based on actual patient data collected over time. A compromise approach may utilize posture state definitions followed by some of the adaptive techniques described herein, possibly incorporating use of therapy regions into the hysteresis space.

It will be appreciated that the various techniques described herein may be used alone or in any combination. As one example, when a device is first deployed, the estimation techniques described above may be used to select estimated vectors that are then associated with posture state definitions and therapy parameter values. These initial definitions may be used to deliver therapy to a patient when therapy is first initiated (e.g., after implant). Thereafter, vector adaptation techniques may be applied to capture actual vectors and modify the vectors associated with the posture state definitions to more closely match actual posture states.

In addition to, or instead of, employing the vector adaptation techniques to adapt the vectors to more closely match those associated with actual posture states, associations between posture states and parameters may be dynamically created over time (e.g., by creating library entries). Such dynamically-created associations may supplement or replace those original posture state definitions, as exemplified in FIGS. 15-21. In one embodiment, as the library entries are created, those library entries will take priority over the predefined posture state definitions. In this manner, the area in three-dimensional space that had originally been associated with the posture state definitions may be slowly "eroded", being replaced by the library entries for posture states that are not part of any predetermined posture state set. Eventually, all of three-dimensional space may be occupied by the vectors contained within the library entries. In this manner, the predetermined posture state definitions may be used to provide a "starting point" for therapy delivery when an IMD 12 is first deployed. However, thereafter a more specific library of control points (e.g., vectors) may be developed based on the patient's daily life. As previously discussed, these dynamically-created associations need not be part of any predetermined posture state set, but may represent any points in three-dimensional space that correspond with a posture state the patient occupied at least once.

After the library of such associations is created, the library entries may be grouped into posture state regions as described herein. Such posture state regions may be more efficiently searched and managed than the library of discrete vectors, and may conserve both storage space and power resources.

In the foregoing manner, original posture state definitions that may be associated with estimated vectors may be replaced over time with a library of dynamically-captured posture states. That library, in turn, may be automatically processed to form posture state regions that can more concisely and efficiently represent the collection of vectors contained within the library.

While the above discussion provides examples of using the various mechanisms disclosed herein in combination, these techniques may be used alone as well. For instance, in an embodiment that does not require use of accurate posture vectors for therapy delivery, originally-estimated posture vectors can be used indefinitely. Such a practice may be preferred in a system wherein power savings is critical such that it is undesirable to continue vector refinement as the patient goes about daily life. Thus, the estimation techniques described herein may be practiced alone, if desired.

Conversely, the original posture vectors used to create posture state vector definitions may be obtained entirely, or in part, by manual methods such as those described in reference to FIGS. 6A and 6B. For instance, the original posture state definitions may be created by requesting that the patient assume various posture states so that the output of sensor 40 may be captured while the patient occupies each posture. In this case, the automated calibration and vector estimation techniques are not needed. However, adaptation mechanisms may never-the-less be employed so that the posture state definitions are modified over time to more closely reflect the patient's posture state or adapt to a patient's changing conditions. Such an embodiment that uses adaptation techniques without vector-estimation mechanisms may be practiced by clinicians who may have more time to spend with a patient during an initial programming session and who desire more accuracy in the initial definitions.

As another example, library entries that associate posture states with parameters may be employed to populate all of three dimensional space using mechanisms described in reference to FIGS. 15-21 such that no predetermined posture state definitions need be employed, even initially. In such embodiments, both the vector estimation and subsequent adaptation techniques such as those shown in FIGS. 7-13 may be eliminated, and the mechanisms used to build a library of entries in three-dimensional space may be used alone. In this case, the resulting library may, but need not, be processed to develop corresponding posture state regions.

In a similar embodiment, some of three dimensional space may remain allocated to predefined posture states, such as the Upright and Lying Down posture states, with the remainder of three-dimensional space being occupied by vectors associated with library entries that need not be associated with predefined posture states. In this manner, both vectors associated with, and those not associated with, predetermined named posture states may be used together within the same system. In this latter embodiment, the adaptive techniques described herein in relation to the predetermined posture states may be employed to update vectors associated with the predetermined posture states, whereas the techniques described in relation to FIGS. 15-21, including derivation of posture state regions, may be employed to update and maintain vectors that are not associated with predetermined posture states.

Yet other disclosed techniques may be used alone or with any one or more of the other mechanisms disclosed herein. Such techniques include manipulation of avatars to match a patient's posture state, with the resulting posture state representation being used to populate a user interface that reflects posture states supported by the system. Use of this type of avatar may be usefully incorporated in any system that defined posture states according to any of the one or more mechanisms described herein. Yet another such disclosed mechanism includes flip-detection used to trigger some action within the system, such as the updating of one or more posture state definitions or the re-populating of some or all of a library of vectors. Again, such flip detection mechanisms may be usefully employed in any system that provides posture state classification, with or without the use of other techniques disclosed herein.

Other variations, permutations, and combinations of the above-described techniques are possible. While the above described methods are discussed primarily in regards to vectors that are indicative of a patient's posture, it will be appreciated that such mechanisms may equally be applicable to vectors associated with velocity, acceleration, or some other aspect of a patient's posture state. Thus, any vector detectable by sensor 40 may be processed using techniques described herein. Moreover, while the current disclosure describes vectors as being used as an indication of direction in three-dimensional space, any other parameter that provides a directional component and that may be used to identify a posture state may be used instead of a vector within the scope of the current disclosure. Likewise, as previously discussed, while therapy parameters are primarily described as being those associated with the vectors, any operating parameter may be associated with a vector if such association may be usefully employed to control and adapt operation of IMD 12 based on an output of sensor 40. Example parameters include those that control power consumption of the system, signal sampling and processing by one or more sensors of the system, communication with other devices, and so on.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry. When processing is required, as to obtain the estimated posture vectors and/or to update the posture vectors based on signals obtained from sensor 40, the processing may be performed entirely within IMD 12, entirely within programmer 20, or with the aid of both devices. For instance, signals from sensor may be transferred to programmer 20 and thereafter used by programmer 20 to obtain the estimated posture vectors and/or update such vectors. Alternatively, some or all of these steps may be performed by processor 34 of IMD 12. In this regard, one aspect of the disclosure relates to a system comprising processing means for obtaining at least one indication of a posture state of a patient, for determining whether the at least one posture state is stable, and for creating an association between each stable posture state and a corresponding therapy parameter value. The system further includes memory means for storing the association between each stable posture state and a corresponding therapy parameter value. The processing means and/or the memory means may reside within IMD 12 and/or programmer 20.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to cause one or more processors to support one or more aspects of the functionality described in this disclosure. The computer-readable medium may reside within IMD 12 and/or programmer 20. Likewise, a processor that executes these instructions may reside within IMD 12 and/or programmer 20. The computer-readable medium may likewise store various control parameters and functions described herein, such as values of a used to weight vectors, the various functions used to filter samples and to perform the weighting.

According to the foregoing, one aspect of the disclosure relates to an article of manufacture comprising a computer-readable medium storing executable instructions to cause a processor to obtain a parameter indicative of a posture state, and determine whether the parameter indicates a patient is in a stable posture state. If the patient is in a stable posture state, instructions cause the processor to create an association between the posture state and at least one therapy parameter value used to control delivery of therapy to the patient.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Those skilled in the art will recognize that other modifications may be made to the systems, methods, and techniques described herein. For instance, some of the steps of the methods may be implemented in hardware such as posture state module 41. In many cases, steps may be re-ordered, and some steps may be eliminated. Thus, the description of the embodiments is merely exemplary, with the scope of the invention to be defined by the Claims that follow.

What is claimed is:

1. A method comprising:
   detecting an adjustment to a parameter of electrical stimulation therapy delivered to a patient;
   providing, via a sensor, output indicative of a posture state of the patient;
   determining, via a processor, whether stability processing is to be performed;
   if stability processing is to be performed, associating the detected adjustment with the posture state when the posture state does not change within a period of time subsequent to the detected adjustment; and
   if stability processing is not to be performed, associating the detected adjustment with the posture state before the period of time expires.

2. The method of claim 1, wherein determining whether stability processing is to be performed comprises determining, based on user input, whether stability processing is to be performed.

3. The method of claim 1, further comprising:
   receiving user input; and
   wherein determining whether stability processing is to be performed comprises determining whether stability processing is to be performed based on a type of the user input.

4. The method of claim 1, further comprising receiving a trigger event; and
   wherein determining whether stability processing is to be performed comprises determining whether stability processing is to be performed based on a type of the trigger event.

5. The method of claim 1, wherein if stability processing is not to be performed, associating the detected adjustment with the posture state comprises associating the detected adjustment with the posture state at a time determined based on user input.

6. The method of claim 5, wherein the user input comprises tapping input.

7. The method of claim 1, wherein if stability processing is not to be performed, associating the detected adjustment with the posture state before the period of time expires comprises associating the detected adjustment with the posture state without regard to whether the posture state changes prior to associating the detected adjustment with the posture state.

8. The method of claim 1, wherein if stability processing is to be performed, associating the detected adjustment with the posture state via the processor when the posture state does not change within a period of time subsequent to the detected adjustment comprises associating the detected adjustment with the posture state if the posture state is indicated within a first period of time following the detection of the adjustment and if the posture state does not change during a second period of time following the posture state being indicated.

9. The method of claim 1, further comprising:
subsequently detecting the posture state; and
delivering, via a therapy module, therapy to the patient according to the detected adjustment associated with the posture state.

10. The method of claim 1, wherein associating the detected adjustment with the posture state before the period of time expires comprises associating a change in an amplitude with the posture state before the period of time expires.

11. The method of claim 1, wherein associating the detected adjustment with the posture state before the period of time expires comprises associating a change in an amplitude with the posture state at the time a user input is received.

12. The method of claim 1, wherein determining whether stability processing is to be performed for the posture state comprises determining whether stability processing is to be performed for the posture state based on at least one of time of day or day of week.

13. A medical device, comprising:
a sensor configured to provide output indicative of a posture state of a patient; and
a processor configured to:
receive the output of the sensor indicative of a posture state of the patient;
detect an adjustment to a parameter of electrical stimulation therapy delivered to the patient,
determine whether stability processing is to be performed,
if stability processing is to be performed, associate the detected adjustment with the posture state when the posture state does not change within a period of time subsequent to the detected adjustment, and
if stability processing is not to be performed, associate the detected adjustment with the posture state before the period of time expires.

14. The medical device of claim 13, wherein the processor is configured to determine whether stability processing is to be performed based on user input.

15. The medical device of claim 13, wherein the processor is configured to determine whether stability processing is to be performed based on a type of user input.

16. The medical device of claim 13, wherein the processor is further configured to receive a trigger event, and to determine whether stability processing is to be performed based on a type of the trigger event.

17. The medical device of claim 13, wherein the processor is configured to, if stability processing is not to be performed, associate the detected adjustment with the posture state at a time determined based on user input.

18. The medical device of claim 17, wherein the user input comprises tapping input.

19. The medical device of claim 13, wherein the processor is configured to, if stability processing is not to be performed, associate the detected adjustment with the posture state without regard to whether the posture state changed prior to associating the detected adjustment with the posture state.

20. The medical device of claim 13, wherein the processor is configured to, if stability processing is to be performed, associate the detected adjustment with the posture state if the posture state is indicated within a first period of time following the detection of the adjustment and if the posture state does not change during a second period of time following the indication of the posture state.

21. The medical device of claim 13, wherein the processor is configured to subsequently detect the posture state and control delivery of the electrical stimulation therapy to the patient according to the detected adjustment associated with the posture state.

22. The medical device of claim 13, wherein the processor is configured to, if stability processing is not to be performed, associate a change in an amplitude of the electrical stimulation therapy delivered to the patient with the posture state before the period of time expires.

23. The medical device of claim 13, wherein the processor is configured to, if stability processing is not to be performed, associate a change in an amplitude with the posture state at a time a user input is received.

24. The medical device of claim 13, wherein the processor is configured to determine whether stability processing is to be performed for the posture state based on at least one of time of day or day of week.

25. The medical device of claim 13, where at least one of the sensor and the processor are configured to be implantable.

26. A medical system, comprising:
a sensor configured to provide an output indicative of a posture state of a patient; and
a processor configured to:
receive an output from the sensor indicative of a posture state of the patient;
detect an adjustment to a parameter of electrical stimulation therapy delivered to the patient,
determine whether stability processing is to be performed for the posture state,
if stability processing is to be performed, associate the detected adjustment with the posture state when the posture state does not change within a period of time subsequent to the detected adjustment, and
if stability processing is not to be performed, associate the detected adjustment with the posture state before the period of time expires.

27. The medical system of claim 26, wherein the processor is configured to determine whether stability processing is to be performed based on user input.

28. The medical system of claim 26, further comprising a programmer that comprises the processor.

29. The medical system of claim 26, further comprising an implantable medical device that comprises the processor.

30. The medical system of claim 26, wherein the processor is configured to, if stability processing is not to be performed, associate a change in an amplitude of the electrical stimulation therapy delivered to the patient with the posture state before the period of time expires.

31. A non-transitory computer-readable storage medium storing instructions to cause a programmable processor to:
detect an adjustment to a parameter of electrical stimulation therapy delivered to a patient;
receive an output of a sensor that is indicative of a posture state of the patient;
determine whether stability processing is to be performed for the posture state;

if stability processing is to be performed, associate the detected adjustment with the posture state when the posture state does not change within a period of time subsequent to the detected adjustment; and if stability processing is not to be performed, associate the detected adjustment with the posture state before the period of time expires.

32. A system, comprising:

means for detecting an adjustment to a parameter of electrical stimulation therapy delivered to a patient;

means for providing a signal indicative of a posture state of the patient;

means for determining whether stability processing is to be performed for the posture state;

if stability processing is to be performed, means for associating the detected adjustment with the posture state when the posture state does not change within a period of time subsequent to the detected adjustment; and if stability processing is not to be performed, means for associating the detected adjustment with the posture state before the period of time expires.

* * * * *